(12) United States Patent
Sharpe

(10) Patent No.: US 10,681,909 B2
(45) Date of Patent: Jun. 16, 2020

(54) HERBICIDAL TRIAZOLES

(71) Applicant: FMC Corporation, Philadelphia, PA (US)

(72) Inventor: Paula Louise Sharpe, Middletown, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/506,047

(22) PCT Filed: Aug. 27, 2015

(86) PCT No.: PCT/US2015/047105
§ 371 (c)(1),
(2) Date: Feb. 23, 2017

(87) PCT Pub. No.: WO2016/033285
PCT Pub. Date: Mar. 3, 2016

(65) Prior Publication Data
US 2017/0354149 A1 Dec. 14, 2017

Related U.S. Application Data

(60) Provisional application No. 62/043,942, filed on Aug. 29, 2014.

(51) Int. Cl.
*A01N 43/653* (2006.01)
*C07D 249/08* (2006.01)
*C07D 401/06* (2006.01)

(52) U.S. Cl.
CPC ......... *A01N 43/653* (2013.01); *C07D 249/08* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 4,217,129 A * | 8/1980 | Shephard | A01N 43/50 504/180 |
| 5,869,509 A | 2/1999 | Romine et al. | |
| 5,892,048 A | 4/1999 | Kishimoto et al. | |
| 6,265,426 B1 | 7/2001 | Alanine et al. | |
| 6,362,342 B1 | 3/2002 | Qi et al. | |
| 6,413,992 B1 | 7/2002 | Tisdell et al. | |
| 8,968,708 B2 | 3/2015 | Tachdjian et al. | |
| 2009/0163545 A1 | 6/2009 | Goldfarb | |
| 2009/0306397 A1 | 12/2009 | Bruns et al. | |
| 2009/0318438 A1 | 12/2009 | Chen et al. | |
| 2011/0002866 A1 | 1/2011 | Lubit et al. | |
| 2013/0040950 A1 | 2/2013 | Short et al. | |
| 2013/0225583 A1 | 8/2013 | Shipps et al. | |
| 2015/0152077 A1 | 6/2015 | Wang et al. | |
| 2015/0284343 A1 | 10/2015 | Campbell et al. | |
| 2015/0315178 A1 | 11/2015 | Lawrence et al. | |
| 2016/0068509 A1 | 3/2016 | Stevenson et al. | |

FOREIGN PATENT DOCUMENTS

| | | |
|---|---|---|
| CN | 1188764 A | 7/1998 |
| JP | 10007657 A | 1/1998 |
| JP | 2005/008583 A | 1/2005 |
| JP | 2005/194250 A | 7/2005 |
| WO | 1998/04135 A1 | 2/1998 |
| WO | 1999/02507 A1 | 1/1999 |
| WO | 1999/02518 A1 | 1/1999 |
| WO | 2000/64895 A1 | 11/2000 |
| WO | 2003/053917 A1 | 7/2003 |
| WO | 2008/064317 A1 | 5/2008 |
| WO | 2013/049591 A2 | 4/2013 |
| WO | 2014/070983 A1 | 5/2014 |
| WO | 2014/145986 A1 | 9/2014 |

OTHER PUBLICATIONS

Patani, G. A; LaVoie, E. J. "Bioisosterisnn: A rational approach in drug design" Chem. Rev. 1996, 96, 3147-3176.*

Toxnet Toxicology Data Network, "Oleic Acid", 2008, no pagination. https://toxnet.nlm.nih.gov/cgi-bin/sis/search/a?dbs+hsdb:@term+@DOCNO+1240.*

Romine, et al., "3-[(5-Chloro-2-hydroxyphenyl)methyl]-5-[4-(trifluoromethyl)phenyl]-1,3,4-oxadiazol-2(3H)-one, BMS-191011: Opener of large-conductance Ca2+-activated potassium (maxi-K) channels, identification, solubility, and SAR", J. Med. Chem., vol. 50, nb. 3, (2007), p. 528-542.

Peltason et al., "Exploration of structure-activity relationship determinants in analogue series", J. Med. Chem., vol. 52, nb. 10, (2009), p. 3212-3224.

XP055220379, Theodoridis, et al., "Herbicidal 1-(2,4-dihalo-5-phenoxyphenyl)-4-difluoromethyl-4,5-dihydro-3-methyl-1,2,4-triazolin-5(1H)-one Derivatives—Synthesis and Chemistry of Agrochemicals IV—ACS Symposium Series (ACS Publications)", Synthesis and Chemistry of Agrochemicals III, Jul. 23, 2009.

* cited by examiner

*Primary Examiner* — Erin E Hirt
(74) *Attorney, Agent, or Firm* — Reed A Coats

(57) ABSTRACT

Disclosed are compounds of Formula 1, including all stereoisomers, N-oxides, and salts thereof,

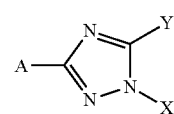

wherein
 A, X and Y are as defined in the disclosure.

Also disclosed are compositions containing the compounds of Formula 1 and methods for controlling undesired vegetation comprising contacting the undesired vegetation or its environment with an effective amount of a compound or a composition of the invention.

15 Claims, No Drawings

HERBICIDAL TRIAZOLES

FIELD OF THE INVENTION

This invention relates to certain triazoles, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all stereoisomers), N-oxides, and salts thereof, agricultural compositions containing them and their use as herbicides:

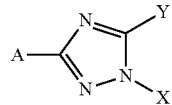

wherein
X is $R^1$ and Y is -$Q^1$-$J^1$; or
X is -$Q^2$-$J^2$ and Y is $R^2$;
$R^1$ is $C_1$-$C_4$ alkyl, $C_1$-$C_4$ haloalkyl, $C_2$-$C_4$ alkenyl, $C_2$-$C_4$ alkynyl, $C_1$-$C_4$ hydroxyalkyl or $C_3$-$C_6$ cycloalkyl;
$Q^1$ is C($R^4$)($R^5$), O, S or N$R^6$;
$R^2$ is halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, S(O)$_n$$R^3$, $C_2$-$C_4$ alkylthioalkyl, $C_2$-$C_4$ alkylsulfonylalkyl, $C_1$-$C_4$ alkylamino, $C_2$-$C_4$ dialkylamino or $C_3$-$C_6$ cycloalkyl;
$Q^2$ is C($R^{4'}$)($R^{5'}$);
each $J^1$ and $J^2$ is independently phenyl substituted with 1 $R^7$ and optionally substituted with up to 2 $R^8$; or a 6-membered aromatic heterocyclic ring substituted with 1 $R^7$ and optionally substituted with up to 2 $R^8$ on carbon ring members; or a 5-membered aromatic heterocyclic ring substituted with 1 $R^9$ on carbon ring members and $R^{11}$ on nitrogen ring members and optionally substituted with 1 $R^{10}$ on carbon ring members;
A is phenyl substituted with up to 4 $R^{16}$; or a 5- or 6-membered aromatic heterocyclic ring substituted with up to 3 $R^{16}$ on carbon ring members and $R^{17}$ on nitrogen ring members;
$R^3$ is independently $C_1$-$C_4$ alkyl or $C_1$-$C_4$ haloalkyl;

each $R^4$ and $R^{4'}$ is independently H, F, Cl, Br, cyano, $C_1$-$C_4$ alkyl, $C_1$-$C_4$ haloalkyl or $CO_2R^{13}$;
each $R^5$ and $R^{5'}$ is independently H, F, $C_1$-$C_4$ alkyl, OH or $OR^{13}$; or
$R^4$ and $R^5$ or $R^{4'}$ and $R^{5'}$ are taken together with the carbon to which they are attached to form C(=O), C(=NOR$^{13}$) or C(=N—N(R$^{14}$)(R$^{15}$));
$R^6$ is H, $C_1$-$C_4$ alkyl or $C_1$-$C_4$ haloalkyl;
$R^7$ is SF$_5$, $C_1$-$C_4$ haloalkyl, $C_1$-$C_4$ alkoxy, $C_1$-$C_4$ haloalkoxy or S(O)$_p$R$^{18}$;
each $R^8$ is independently halogen, cyano, $C_1$-$C_4$ alkyl, $C_1$-$C_4$ haloalkyl, $C_1$-$C_4$ alkoxy, $C_1$-$C_4$ haloalkoxy or S(O)$_p$R$^{19}$; or
$R^7$ and $R^8$ are taken together to form a 5-membered carbocyclic ring containing ring members selected from up to two O atoms or up to two S atoms, and optionally substituted on carbon atom ring members with up to five halogen atoms;
$R^9$ is SF$_5$, $C_1$-$C_4$ haloalkyl, $C_1$-$C_4$ haloalkoxy or S(O)$_p$R$^{18}$, which is at the position meta to the connection of the ring to the remainder of Formula 1;
$R^{10}$ is halogen, cyano, $C_1$-$C_4$ alkyl, $C_1$-$C_4$ haloalkyl, $C_1$-$C_4$ alkoxy, $C_1$-$C_4$ haloalkoxy or S(O)$_p$R$^{19}$;
$R^{11}$ is $C_1$-$C_4$ alkyl or $C_1$-$C_4$ haloalkyl;
each $R^{13}$ is independently $C_1$-$C_4$ alkyl;
$R^{14}$ is $C_1$-$C_4$ alkyl or $C_1$-$C_4$ haloalkyl;
$R^{15}$ is $C_1$-$C_4$ alkyl or $C_1$-$C_4$ haloalkyl;
each $R^{16}$ is independently H, halogen, cyano, nitro, SF$_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy or S(O)$_p$R$^{20}$;
each $R^{17}$ is independently H, $C_1$-$C_4$ alkyl or $C_1$-$C_4$ haloalkyl;
each $R^{18}$ is independently $C_1$-$C_4$ alkyl or $C_1$-$C_4$ haloalkyl;
each $R^{19}$ is independently $C_1$-$C_4$ alkyl or $C_1$-$C_4$ haloalkyl;
$R^{20}$ is $C_1$-$C_4$ alkyl or $C_1$-$C_4$ haloalkyl;
n is 0 or 1; and
each p is independently 0, 1 or 2;
provided when $R^1$ is ethyl and $Q^1$ is CH$_2$, then $J^1$ is other than 3-trifluoromethyl-1H-pyrazol-1-yl.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating reagent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating reagents include the variety of carbon-bound substituent radicals specified for $R^1$ and $Q^2$.

In the above recitations, the term "alkyl", used either alone or in compound words such as "alkylthioalkyl" or "haloalkyl" includes straight-chain or branched alkyl, such as methyl, ethyl, n-propyl, i-propyl or the different butyl isomers. "Alkenyl" includes straight-chain or branched alkenes such as ethenyl, 1-propenyl, 2-propenyl and the different butenyl isomers. "Alkenyl" also includes polyenes such as 1,2-propadienyl. "Alkynyl" includes straight-chain or branched alkynes such as ethynyl, 1-propynyl, 2-propynyl and the different butynyl isomers.

"Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HCCCH_2O$ and $CH_3CCCH_2O$. Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$ and $CH_3CH_2SCH_2CH_2$. "Alkylamino" and "dialkylamino" are defined analogously to the above examples.

"Cycloalkyl" includes, for example, cyclopropyl, cyclobutyl, cyclopentyl and cyclohexyl. The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy" is defined analogously to the term "haloalkyl". Examples of "haloalkoxy" include $CF_3O-$, $CCl_3CH_2O-$, $HCF_2CH_2CH_2O-$ and $CF_3CH_2O-$.

"Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3OC(=O)-$, $CH_3CH_2OC(=O)-$, $CH_3CH_2CH_2OC(=O)-$, $(CH_3)_2CHOC(=O)-$ and the different butoxy- or pentoxycarbonyl isomers.

The total number of carbon atoms in a substituent group is indicated by the "$C_i$-$C_j$" prefix where i and j are numbers from 1 to 6. For example, $C_1$-$C_4$ haloalkoxy designates halomethoxy through halobutoxy; $C_2$ alkoxyalkyl designates $CH_3OCH_2-$; $C_3$ alkoxyalkyl designates, for example, $CH_3CH(OCH_3)-$, $CH_3OCH_2CH_2-$ or $CH_3CH_2OCH_2-$; and $C_4$ alkoxyalkyl designates the various isomers of an alkyl group substituted with an alkoxy group containing a total of four carbon atoms, examples including $CH_3CH_2CH_2OCH_2-$ and $CH_3CH_2OCH_2CH_2-$.

When a fully unsaturated carbocyclic ring satisfies Hückel's rule, then said ring is also called an "aromatic ring".

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring".

"Aromatic" indicates that each of the ring atoms is essentially in the same plane and has a p-orbital perpendicular to the ring plane, and that $(4n+2)\pi$ electrons, where n is a positive integer, are associated with the ring to comply with Hückel's rule.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As noted above, A can be (among others) phenyl optionally substituted with one or more substituents selected from a group of substituents as defined in the Summary of the Invention. An example of phenyl optionally substituted with one to four substituents is the ring illustrated as U-1 in Exhibit 1, wherein $R^v$ is $R^{16}$ as defined in the Summary of the Invention for A and r is an integer (from 0 to 4).

As noted above, A can be (among others) 5- or 6-membered aromatic heterocyclic ring, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for A (i.e. $R^{16}$ or $R^{17}$) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

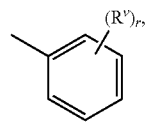
U-1

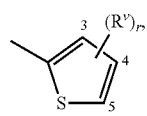
U-2

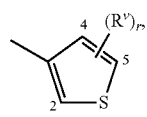
U-3

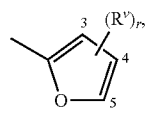
U-4

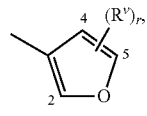
U-5

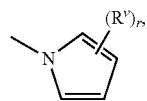
U-6

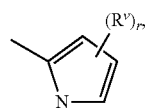
U-7

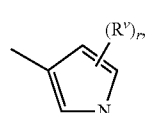
U-8

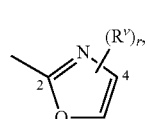
U-9

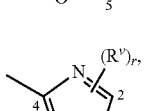
U-10

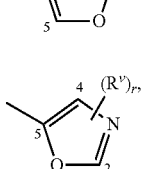
U-11

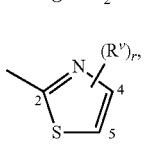
U-12

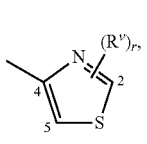
U-13

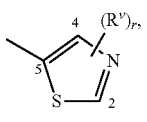
U-14

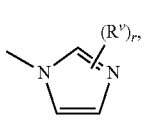
U-15

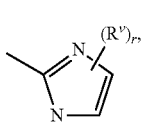
U-16

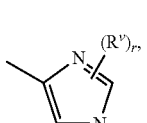
U-17

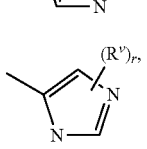
U-18

-continued
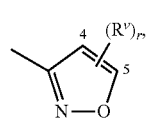
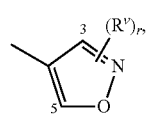
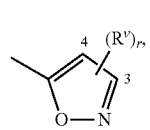
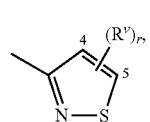
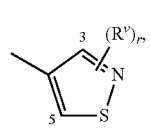
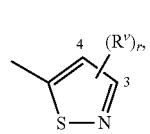
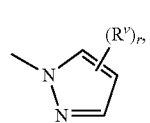
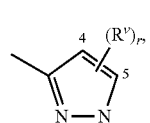
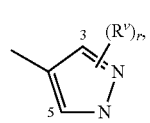
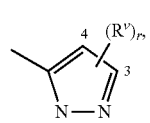
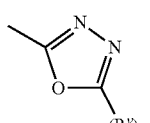
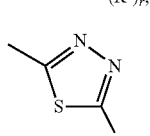
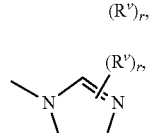
U-19
U-20
U-21
U-22
U-23
U-24
U-25
U-26
U-27
U-28
U-29
U-30
U-31
-continued
U-32
U-33
U-34
U-35
U-36
U-37
U-38
U-39
U-40
U-41
U-42
U-43

U-44 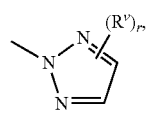

U-45 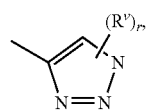

U-46 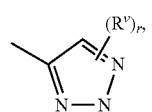

U-47 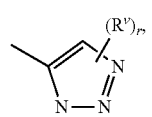

U-48 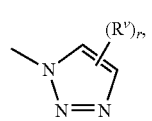

U-49 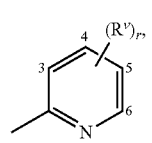

U-50 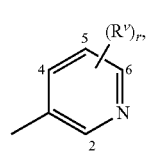

U-51 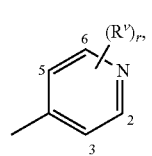

U-52 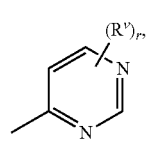

U-53 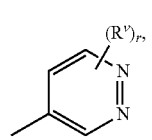

U-54 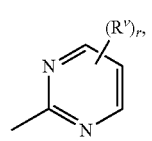

U-55 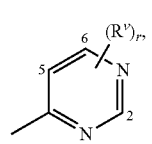

U-56 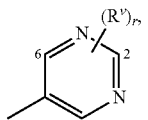

U-57 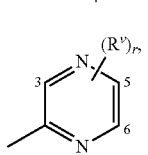

U-58 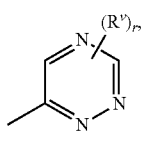

U-59 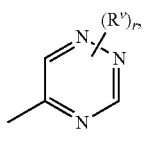

U-60 and U-61 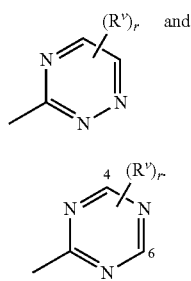

Although $R^v$ groups are shown in the structures U-1 through U-61, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and noncrystalline forms of the compounds they represent. Noncrystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 (including all stereoisomers), N-oxides, and salts thereof, agricultural compositions containing them and their use as herbicides as described in the Summary of the Invention.

Embodiment 1a

A compound of Embodiment 1 wherein X is $R^1$ and Y is $-Q^1-J^1$.

Embodiment 1b

A compound of Embodiment 1 wherein X is $-Q^2-J^2$ and Y is $R^2$.

Embodiment 2

A compound of Embodiment 1 wherein $R^1$ is $C_1$-$C_4$ alkyl, $C_1$-$C_4$ haloalkyl, $C_2$-$C_4$ alkenyl or $C_2$-$C_4$ alkynyl.

Embodiment 3

A compound of Embodiment 2 wherein $R^1$ is $C_1$-$C_4$ alkyl or $C_1$-$C_4$ haloalkyl.

Embodiment 4

A compound of Embodiment 3 wherein $R^1$ is $C_1$-$C_4$ alkyl.

Embodiment 5

A compound of Embodiment 4 wherein $R^1$ is propyl, ethyl or methyl.

Embodiment 6

A compound of Embodiment 5 wherein $R^1$ is propyl.

Embodiment 7

A compound of any one of Embodiments 1 through 6 wherein $Q^1$ is $C(R^4)(R^5)$ or O.

Embodiment 8

A compound of Embodiment 7 wherein $Q^1$ is $C(R^4)(R^5)$.

Embodiment 9

A compound of Embodiment 7 wherein $Q^1$ is O.

Embodiment 10

A compound of any one of Embodiments 1 through 6 wherein $Q^1$ is $NR^6$.

Embodiment 11

A compound of any one of Embodiments 1 through 8 wherein $R^4$ is H, F or $C_1$-$C_4$ alkyl.

Embodiment 11a

A compound of Embodiment 11 wherein $R^4$ is H.

Embodiment 12

A compound of any one of Embodiments 1 through 8 wherein $R^5$ is H, F, $C_1$-$C_4$ alkyl or OH.

Embodiment 12a

A compound of Embodiment 12 wherein $R^5$ is H or OH.

Embodiment 13

A compound of Embodiment 12 wherein $R^5$ is H.

Embodiment 14

A compound of any one of Embodiments 1 through 8 wherein $R^4$ and $R^5$ are taken together with the carbon to which they are attached to form $C(=O)$, $C(=NOR^{13})$ or $C(=N-N(R^{14})(R^{15}))$;

Embodiment 15

A compound of Embodiment 1 wherein $R^6$ is H or $C_1$-$C_4$ alkyl.

Embodiment 16

A compound of Embodiment 15 wherein $R^6$ is $CH_3$.

Embodiment 17

A compound of Embodiment 15 wherein $R^6$ is H.

Embodiment 18

A compound of Embodiment 1 wherein $R^2$ is $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_4$ alkylthioalkyl or $C_3$-$C_6$ cycloalkyl.

Embodiment 19

A compound of Embodiment 18 wherein $R^2$ is $C_1$-$C_4$ alkoxy, $C_1$-$C_4$ haloalkoxy, $C_2$-$C_4$ alkoxyalkyl, $C_1$-$C_4$ alkyl or $C_1$-$C_4$ haloalkyl.

Embodiment 20

A compound of Embodiment 19 wherein $R^2$ is $C_1$-$C_4$ alkoxy or $C_1$-$C_4$ alkyl.

Embodiment 21

A compound of Embodiment 20 wherein $R^2$ is $C_1$-$C_4$ alkoxy.

Embodiment 22

A compound of Embodiment 20 wherein $R^2$ is $C_1$-$C_4$ alkyl.

Embodiment 23

A compound of Embodiment 21 wherein $R^2$ is ethoxy or methoxy.

Embodiment 24

A compound of Embodiment 23 wherein $R^2$ is ethoxy.

Embodiment 25

A compound of Embodiment 22 wherein $R^2$ is ethyl or propyl.

Embodiment 26

A compound of Embodiment 25 wherein $R^2$ is propyl.

Embodiment 27

A compound of Embodiment 1 or any one of Embodiments 18 through 26 wherein $Q^2$ is $C(R^{4'})(R^{5'})$.

Embodiment 27a

A compound of Embodiment 27 wherein $R^{4'}$ is independently H, F, Cl, Br, $C_1$-$C_4$ alkyl or $CO_2R^{13}$.

Embodiment 27b

A compound of Embodiment 27a wherein $R^{4'}$ is independently H, F, Cl, $C_1$-$C_4$ alkyl.

Embodiment 27c

A compound of Embodiment 27b wherein $R^{4'}$ is independently H, F, Cl, $CH_3$ or $CH_2CH_3$.

Embodiment 27d

A compound of Embodiment 27c wherein $R^{4'}$ is independently H, F, $CH_3$ or $CH_2CH_3$.

Embodiment 27e

A compound of Embodiment 27d wherein $R^{4'}$ is independently H, F or $CH_3$.

Embodiment 28

A compound of Embodiment 27 wherein $R^{4'}$ is H.

Embodiment 28a

A compound of Embodiment 27 wherein $R^{5'}$ is H, F, $CH_3$, $CH_2CH_3$, OH or $OR^{13}$.

Embodiment 28b

A compound of Embodiment 28a wherein $R^{5'}$ is H, F, $CH_3$ or $CH_2CH_3$ or $OR^{13}$.

Embodiment 28c

A compound of Embodiment 28b wherein $R^{5'}$ is H, F, $CH_3$ or $CH_2CH_3$.

Embodiment 28d

A compound of Embodiment 28c wherein $R^{5'}$ is H, F or $CH_3$.

Embodiment 29

A compound of Embodiment 27 wherein $R^{5'}$ is H or OH.

Embodiment 30

A compound of Embodiment 29 wherein $R^{5'}$ is H.

Embodiment 31

A compound of Embodiment 27 wherein $R^{4'}$ and $R^{5'}$ are taken together with the carbon to which they are attached to form C(=O), C(=NOR$^{13}$) or C(=N—N(R$^{14}$)(R$^{15}$)).

Embodiment 32

A compound of any one of Embodiments 1 through 31 wherein each $J^1$ or $J^2$ is independently selected from

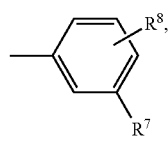
J-1

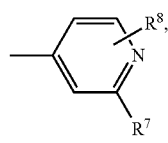
J-2

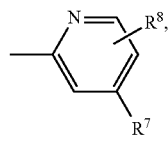
J-3

-continued

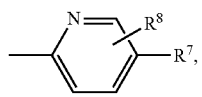
J-4

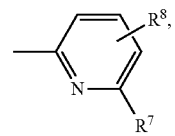
J-5

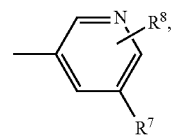
J-6

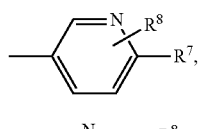
J-7

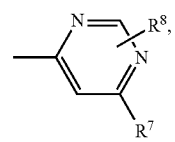
J-8

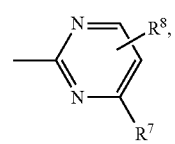
J-9

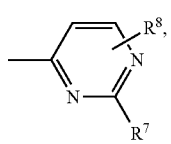
J-10

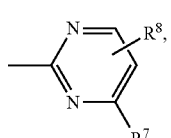
J-11

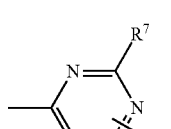
J-12

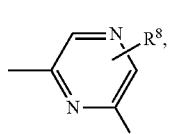
J-13

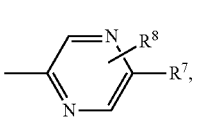
J-14

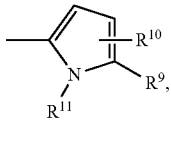
J-15

-continued

J-16 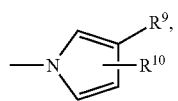

J-17 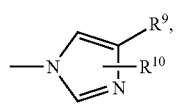

J-18 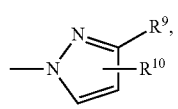

J-19 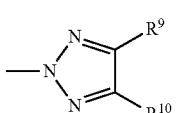

J-20 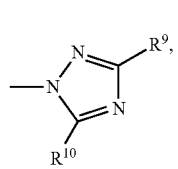

J-21 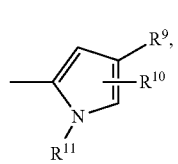

J-22 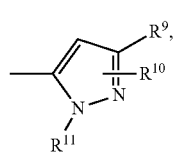

J-23 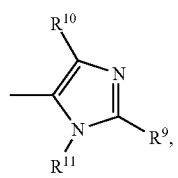

J-24 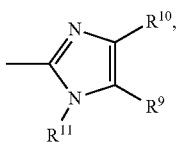

J-25 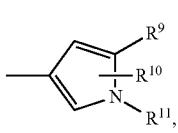

J-26 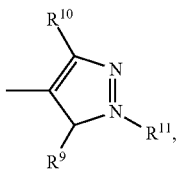

-continued

J-27 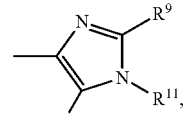

J-28 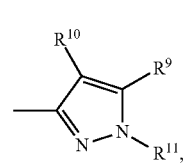

J-29 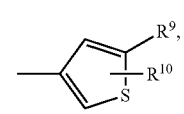

J-30 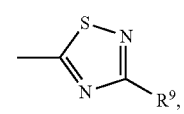

J-31 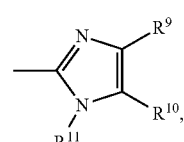

J-32 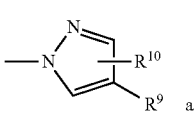 and

J-33 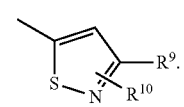

Embodiment 33

A compound of Embodiment 32 wherein each $J^1$ or $J^2$ is selected from J-1 through J-14 (i.e. phenyl or a 6-membered heteroaromatic ring).

Embodiment 34

A compound of Embodiment 32 wherein $J^1$ or $J^2$ is selected from J-15 through J-33 (i.e. a 5-membered heteroaromatic ring).

Embodiment 35

A compound of Embodiment 33 wherein $J^1$ or $J^2$ is selected from J-1 and J-2.

Embodiment 36

A compound of Embodiment 35 wherein $J^1$ or $J^2$ is J-1.

Embodiment 37

A compound of Embodiment 35 wherein $J^1$ or $J^2$ is J-2.

Embodiment 38

A compound of Embodiment 36 wherein $J^1$ is J-1.

Embodiment 39

A compound of Embodiment 38 wherein $J^1$ is J-1 and $R^7$ is $CF_3$.

Embodiment 40

A compound of Embodiment 37 wherein $J^1$ is J-2.

Embodiment 41

A compound of Embodiment 40 wherein $J^1$ is J-2 and $R^7$ is $CF_3$.

Embodiment 42

A compound of Embodiment 36 wherein $J^2$ is J-1.

Embodiment 43

A compound of Embodiment 42 wherein $J^2$ is J-1 and $R^7$ is $CF_3$.

Embodiment 44

A compound of Embodiment 37 wherein $J^2$ is J-2.

Embodiment 45

A compound of Embodiment 44 wherein $J^2$ is J-2 and $R^7$ is $CF_3$.

Embodiment 45A

A compound of Formula 1 wherein each $J^1$ and $J^2$ is independently a 6-membered aromatic heterocyclic ring substituted with 1 $R^7$ and optionally substituted with up to 2 $R^8$ on carbon ring members; or a 5-membered aromatic heterocyclic ring substituted with 1 $R^9$ on carbon ring members and $R^{11}$ on nitrogen ring members and optionally substituted with 1 $R^{10}$ on carbon ring members.

Embodiment 45B

A compound of Embodiment 45A wherein $J^1$ is a 6-membered aromatic heterocyclic ring substituted with 1 $R^7$ and optionally substituted with up to 2 $R^8$ on carbon ring members; or a 5-membered aromatic heterocyclic ring substituted with 1 $R^9$ on carbon ring members and $R^{11}$ on nitrogen ring members and optionally substituted with 1 $R^{10}$ on carbon ring members.

Embodiment 45C

A compound of Embodiment 45B wherein $J^1$ is a 6-membered aromatic heterocyclic ring substituted with 1 $R^7$ and optionally substituted with up to 2 $R^8$ on carbon ring members.

Embodiment 45D

A compound of Embodiment 45A wherein $J^2$ is a 6-membered aromatic heterocyclic ring substituted with 1 $R^7$ and optionally substituted with up to 2 $R^8$ on carbon ring members; or a 5-membered aromatic heterocyclic ring substituted with 1 $R^9$ on carbon ring members and $R^{11}$ on nitrogen ring members and optionally substituted with 1 $R^{10}$ on carbon ring members.

Embodiment 45E

A compound of Embodiment 45D wherein $J^2$ is a 6-membered aromatic heterocyclic ring substituted with 1 $R^7$ and optionally substituted with up to 2 $R^8$ on carbon ring members.

Embodiment 45F

A compound of Embodiment 45D wherein $J^2$ is a 5-membered aromatic heterocyclic ring substituted with 1 $R^9$ on carbon ring members and $R^{11}$ on nitrogen ring members and optionally substituted with 1 $R^{10}$ on carbon ring members.

Embodiment 45G

A compound of any one of Embodiments 1 through 31 wherein each $J^1$ or $J^2$ is independently selected from

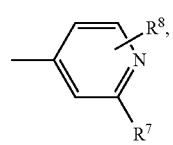

J-2

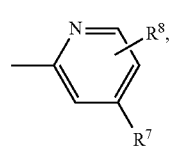

J-3

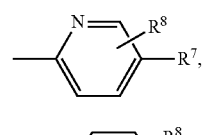

J-4

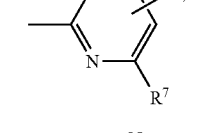

J-5

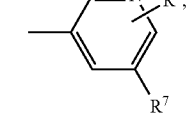

J-6

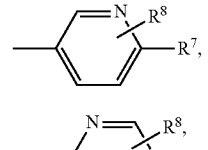

J-7

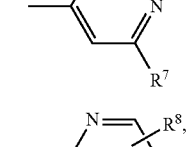

J-8

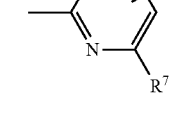

J-9

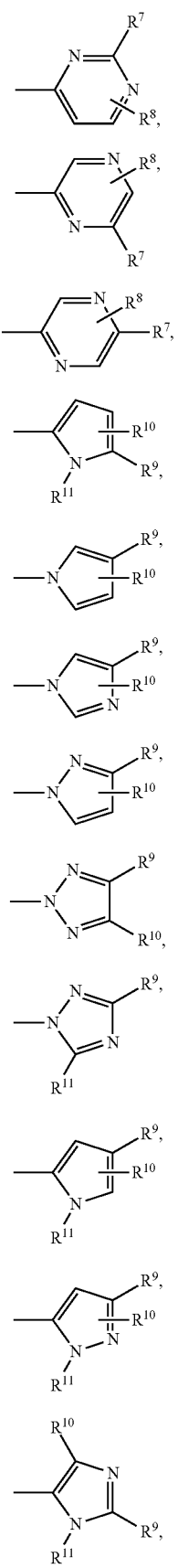
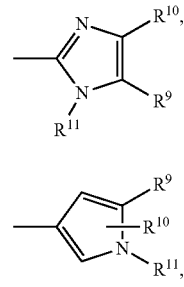
Embodiment 45H
A compound of Embodiment 45G wherein each $J^1$ or $J^2$ is selected from J-2 through J-14 (i.e. 6-membered heteroaromatic ring).

Embodiment 45I

A compound of Embodiment 45G wherein $J^1$ or $J^2$ is selected from J-15 through J-33 (i.e. a 5-membered heteroaromatic ring).

Embodiment 45J

A compound of Embodiment 45G wherein $J^1$ or $J^2$ is selected from J-2, J-3, J-4, J-5, J-6, J-7, J-9, J-12, J-17, J-18, J-20, J-22, J-26, J-29 and J-30.

Embodiment 45K

A compound of Embodiment 45J wherein $J^1$ or $J^2$ is selected from J-2, J-12, J-17, J-18, J-20 and J-22.

Embodiment 45L

A compound of Embodiment 45J wherein $J^1$ or $J^2$ is selected from J-2, J-20 and J-22.

Embodiment 45M

A compound of Embodiment 45J wherein $J^1$ or $J^2$ is J-2.

Embodiment 45N

A compound of Embodiment 45J wherein $J^1$ or $J^2$ is J-22.

Embodiment 45O

A compound of Embodiment 45J wherein $J^1$ is J-2 and $R^7$ is $CF_3$.

Embodiment 45P

A compound of Embodiment 45J wherein $J^2$ is J-2.

Embodiment 45Q

A compound of Embodiment 45J wherein $J^2$ is J-2 and $R^7$ is $CF_3$.

Embodiment 45R

A compound of Formula 1 or any one of Embodiments 1 through 45Q wherein A is a 5- or 6-membered aromatic heterocyclic ring substituted with up to 3 $R^{16}$ on carbon ring members and $R^{17}$ on nitrogen ring members.

Embodiment 45S

A compound of 45R wherein A is a 6-membered aromatic heterocyclic ring substituted with up to 3 $R^{16}$ on carbon ring members and $R^{17}$ on nitrogen ring members.

Embodiment 45T

A compound of Embodiment 45R wherein A is a 5-membered aromatic heterocyclic ring substituted with up to 3 $R^{16}$ on carbon ring members and $R^{17}$ on nitrogen ring members.

Embodiment 45U

A compound of Embodiment 45T where A is other than a substituted 1H-pyrazol-5-yl moiety.

Embodiment 46

A compound of any one of Embodiments 1 through 45 wherein A is phenyl substituted with up to 3 $R^{16}$.

Embodiment 47

A compound of Embodiments 46 wherein A is phenyl substituted with up to 2 $R^{16}$.

Embodiment 48

A compound of Embodiments 47 wherein A is phenyl substituted with 1 $R^{16}$.

Embodiment 49

A compound of Embodiment 48 wherein the $R^{16}$ is at the position para to the connection of the phenyl ring to the remainder of Formula 1.

Embodiment 50

A compound of any one of Embodiments 38, 40, 42 and 44 wherein $R^7$ is $SF_5$, $C_1$-$C_4$ haloalkyl, $C_1$-$C_4$ alkoxy or $C_1$-$C_4$ haloalkoxy.

Embodiment 51

A compound of Embodiment 50 wherein $R^7$ is $C_1$-$C_4$ haloalkyl, $C_1$-$C_4$ alkoxy or $C_1$-$C_4$ haloalkoxy.

Embodiment 52

A compound of Embodiment 51 wherein $R^7$ is $C_1$-$C_4$ haloalkyl.

Embodiment 53

A compound of Embodiment 52 wherein $R^7$ is $CF_3$.

Embodiment 54

A compound of Embodiment 51 wherein $R^7$ is $C_1$-$C_4$ alkoxy.

Embodiment 55

A compound of Embodiment 51 wherein $R^7$ is $C_1$-$C_4$ haloalkoxy.

Embodiment 56

A compound of any one of Embodiments 1 through 55 wherein each $R^8$ is independently halogen or $C_1$-$C_4$ haloalkyl.

Embodiment 57

A compound of Embodiment 56 wherein each $R^8$ is independently F, Cl or $CF_3$.

Embodiment 58

A compound of Embodiment 57 wherein each $R^8$ is F.

Embodiment 59

A compound of any one of Embodiments 1 through 58 wherein each $R^{13}$ is independently $CH_3$.

Embodiment 60

A compound of Embodiment 47 wherein each $R^{16}$ is independently halogen, cyano, $SF_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl or $C_2$-$C_4$ alkynyl.

Embodiment 60a

A compound of Embodiment 60 wherein each $R^{16}$ is independently halogen or $C_1$-$C_4$ haloalkyl.

Embodiment 60b

A compound of Embodiment 60a wherein each $R^{16}$ is independently halogen.

Embodiment 61

A compound of Embodiment 48 wherein $R^{16}$ is halogen, cyano, $SF_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl or $C_2$-$C_4$ alkynyl.

Embodiment 61a

A compound of Embodiment 61 wherein $R^{16}$ is $C_1$-$C_4$ haloalkyl or halogen.

Embodiment 62

A compound of Embodiment 61a wherein $R^{16}$ is $CF_3$ or F.

Embodiment 63

A compound of Embodiment 62 wherein the $R^{16}$ is at the position para to the connection of the phenyl ring to the remainder of Formula 1.

Embodiment 64

A compound of Formula 1 that is other than 4-[[3-[3,5-bis(trifluoromethyl)phenyl]-1-methyl-1H-1,2,4-triazol-5-yl]thio]-6-chloro-2-(methylthio)-pyrimidine (CAS #1508257-65-5).

Embodiment 65

A compound of Formula 1 provided that when A is phenyl substituted with 1 $R^{16}$, X is $R^1$ and Y is -$Q^1$-$J^1$, $R^1$ is ethyl, and $Q^1$ is $CH_2$; then $J^1$ is other than 3-trifluoromethyl-1H-pyrazol-1yl.

Embodiments of this invention, including Embodiments 1-65 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-65 above as well as any other embodiments described herein, and any combination thereof, pertain to the compositions and methods of the present invention.

Combinations of Embodiments 1-65 are illustrated by:

Embodiment AB

A compound of the Summary of the Invention wherein $J^1$ or $J^2$ is independently selected from

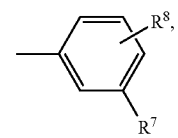
J-1

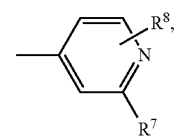
J-2

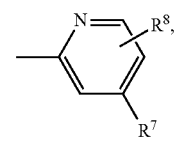
J-3

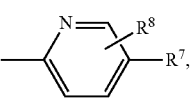
J-4

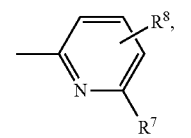
J-5

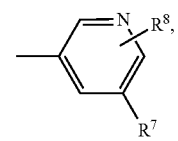
J-6

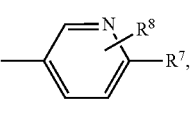
J-7

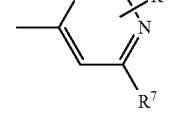
J-8

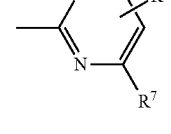
J-9

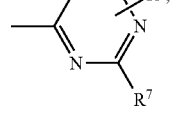
J-10

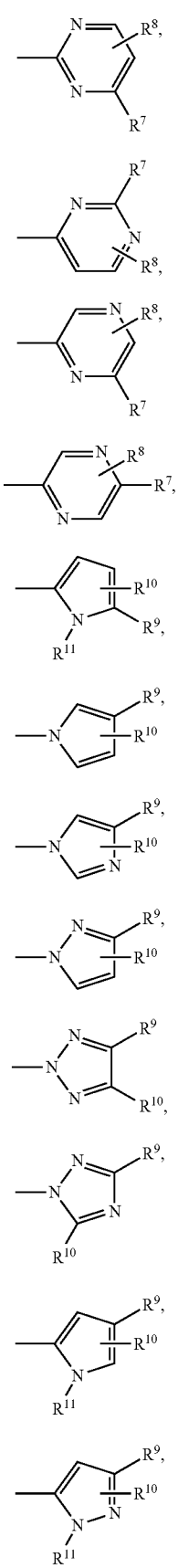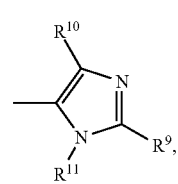

Embodiment AB1
A compound of the Summary of the Invention wherein $J^1$ or $J^2$ is independently selected from
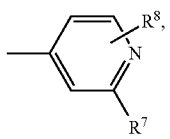  J-2
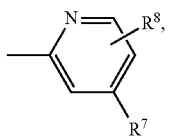  J-3
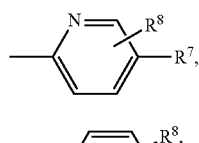  J-4
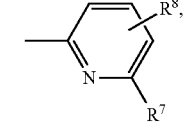  J-5
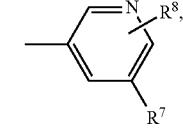  J-6
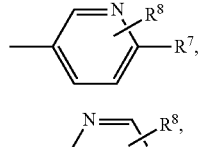  J-7
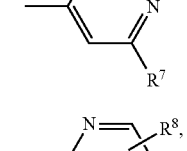  J-8
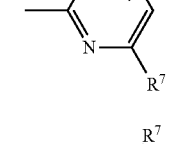  J-9
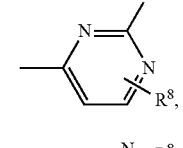  J-12
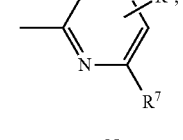  J-13
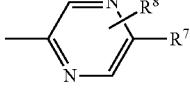  J-14
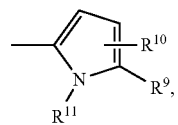  J-15
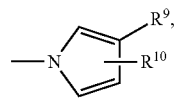  J-16
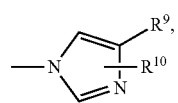  J-17
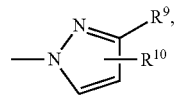  J-18
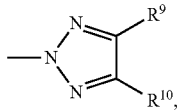  J-19
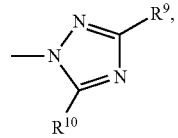  J-20
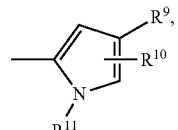  J-21
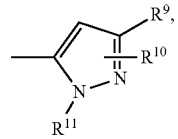  J-22
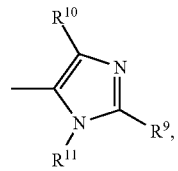  J-23
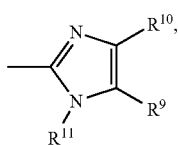  J-24
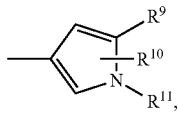  J-25

-continued

J-26 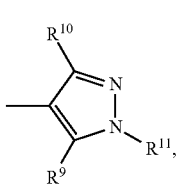

J-27 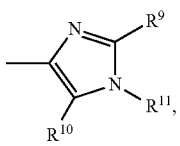

J-28 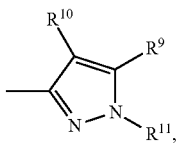

J-29 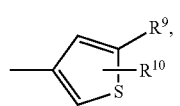

J-30 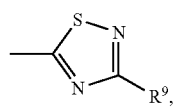

J-31 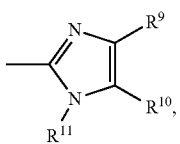

J-32 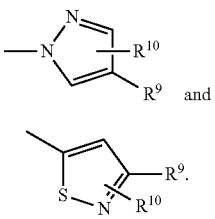

and

J-33

Embodiment 1A

A compound of Embodiment AB wherein
X is $R^1$ and Y is -$Q^1$-$J^1$;
$R^1$ is $C_1$-$C_4$ alkyl, $C_1$-$C_4$ haloalkyl, $C_2$-$C_4$ alkenyl or $C_2$-$C_4$ alkynyl;
$Q^1$ is $C(R^4)(R^5)$ or O;
$R^4$ is H;
$R^5$ is H or OH;
$J^1$ is selected from J-1 and J-2;
$R^7$ is $SF_5$, $C_1$-$C_4$ haloalkyl, $C_1$-$C_4$ alkoxy or $C_1$-$C_4$ haloalkoxy;
A is phenyl substituted with up to 2 $R^{16}$; and
each $R^{16}$ is independently $C_1$-$C_4$ haloalkyl or halogen.

Embodiment 1A1

A compound of Embodiment AB, AB1 or 1A wherein
X is $R^1$ and Y is -$Q^1$-$J^1$;
$R^1$ is $C_1$-$C_4$ alkyl, $C_1$-$C_4$ haloalkyl, $C_2$-$C_4$ alkenyl or $C_2$-$C_4$ alkynyl;
$Q^1$ is $C(R^4)(R^5)$ or O;
$R^4$ is H;
$R^5$ is H or OH;
$R^7$ is $SF_5$, $C_1$-$C_4$ haloalkyl, $C_1$-$C_4$ alkoxy or $C_1$-$C_4$ haloalkoxy;
A is phenyl substituted with up to 2 $R^{16}$; and
each $R^{16}$ is independently $C_1$-$C_4$ haloalkyl or halogen.

Embodiment 1B

A compound of Embodiment 1A wherein
$R^1$ is $C_1$-$C_4$ alkyl or $C_1$-$C_4$ haloalkyl;
$Q^1$ is $C(R^4)(R^5)$;
$R^5$ is H;
$J^1$ is J-1;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 1C

A compound of Embodiment 1A wherein
$R^1$ is $C_1$-$C_4$ alkyl or $C_1$-$C_4$ haloalkyl;
$Q^1$ is $C(R^4)(R^5)$;
$R^5$ is H;
$J^1$ is J-2;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 1D

A compound of Embodiment 1A wherein
$R^1$ is $C_1$-$C_4$ alkyl or $C_1$-$C_4$ haloalkyl;
$Q^1$ is O;
$J^1$ is selected from J-1 and J-2;
$R^7$ is $C_1$-$C_4$ haloalkyl, $C_1$-$C_4$ alkoxy or $C_1$-$C_4$ haloalkoxy;
A is phenyl substituted with up to 2 $R^{16}$; and
each $R^{16}$ is independently $C_1$-$C_4$ haloalkyl or halogen.

Embodiment 1E

A compound of Embodiment 1D wherein
$R^1$ is propyl, ethyl or methyl;
$J^1$ is J-1;
$R^7$ is $CF_3$;
A is phenyl substituted with 1 $R^{16}$; and
$R^{16}$ is $CF_3$ or F.

Embodiment 1F

A compound of Embodiment 1D wherein
$R^1$ is propyl, ethyl or methyl;
$J^1$ is J-2;
$R^7$ is $CF_3$;
A is phenyl substituted with 1 $R^{16}$; and
$R^{16}$ is $CF_3$ or F.

Embodiment 1G

A compound of any one of Embodiments 1B, 1C, 1E and 1F wherein $R^{16}$ is at the position para to the connection of the phenyl ring to the remainder of Formula 1.

Embodiment 2A

A compound of Embodiment AB wherein
X is -$Q^2$-$J^2$ and Y is $R^2$;
$R^2$ is $C_1$-$C_4$ alkoxy or $C_1$-$C_4$ alkyl;
$Q^2$ is $C(R^{4'})(R^{5'})$;
$R^{4'}$ is H;
$R^{5'}$ is H;
$J^2$ is selected from J-1 and J-2;
$R^7$ is $SF_5$, $C_1$-$C_4$ haloalkyl, $C_1$-$C_4$ alkoxy or $C_1$-$C_4$ haloalkoxy;
A is phenyl substituted with up to 2 $R^{16}$; and
each $R^{16}$ is independently $C_1$-$C_4$ haloalkyl or halogen.

Embodiment 2A1

A compound of Embodiment AB, AB1 or 2A wherein
X is -$Q^2$-$J^2$ and Y is $R^2$;
$R^2$ is $C_1$-$C_4$ alkoxy or $C_1$-$C_4$ alkyl;
$Q^2$ is $C(R^{4'})(R^{5'})$;
$R^{4'}$ is H;
$R^{5'}$ is H;
$R^7$ is $SF_5$, $C_1$-$C_4$ haloalkyl, $C_1$-$C_4$ alkoxy or $C_1$-$C_4$ haloalkoxy;
A is phenyl substituted with up to 2 $R^{16}$; and
each $R^{16}$ is independently $C_1$-$C_4$ haloalkyl or halogen.

Embodiment 2B

A compound of Embodiment 2A wherein
$R^2$ is $C_1$-$C_4$ alkoxy;
$J^2$ is J-1;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 2B1

A compound of Embodiment 2A wherein
$R^2$ is $C_1$-$C_4$ alkoxy;
$J^2$ is selected from J-2, J-12, J-17, J-18, J-20 and J-22;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 2C

A compound of Embodiment 2A or 2B1 wherein
$R^2$ is $C_1$-$C_4$ alkoxy;
$J^2$ is J-2;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 2D

A compound of Embodiment 2A wherein
$R^2$ is $C_1$-$C_4$ alkyl;
$J^2$ is J-1;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 2E

A compound of Embodiment 2A wherein
$R^2$ is $C_1$-$C_4$ alkyl;
$J^2$ is J-2;
$R^7$ is $C_1$-$C_4$ haloalkyl, $C_1$-$C_4$ alkoxy or $C_1$-$C_4$ haloalkoxy;
A is phenyl substituted with 1 $R^{16}$; and
$R^{16}$ is $CF_3$ or F.

Embodiment 2F

A compound of any one of Embodiments 2B, 2C, 2D and 2E wherein $R^{16}$ is at the position para to the connection of the phenyl ring to the remainder of Formula 1.

Specific embodiments include compounds of Formula 1 selected from the group consisting of:
4-[[5-ethyl-3-[4-(trifluoromethyl)phenyl]-1H-1,2,4-triazol-1-yl]methyl]-2-(trifluoromethyl)pyridine (Compound 1);
4-[[3-(4-fluorophenyl)-5-propyl-1H-1,2,4-triazol-1-yl] methyl]-2-(trifluoromethyl)pyridine (Compound 6);
4-[[5-ethoxy-3-(4-fluorophenyl)-1H-1,2,4-triazol-1-yl] methyl]-2-(trifluoromethyl)pyridine (Compound 8);
4-[[3-(4-fluorophenyl)-1-propyl-1H-1,2,4-triazol-5-yl] methyl]-2-(trifluoromethyl)pyridine (Compound 17); and
4-[[3-(4-fluorophenyl)-5-methoxy-1H-1,2,4-triazol-1-yl] methyl]-2-(trifluoromethyl)pyridine (Compound 9).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione.

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methyl sulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

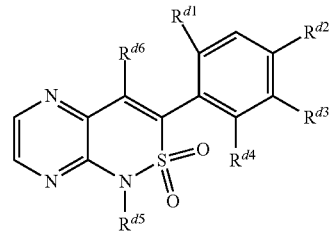

A

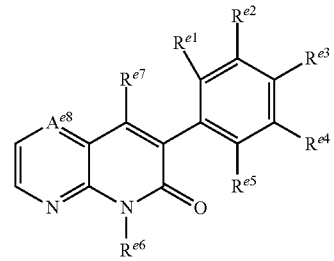

B wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied pre-emergence or early post-emergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7, 8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl) methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660).

The compounds of Formula 1 can be prepared by general methods known in the art of synthetic organic chemistry. One or more of the following methods and variations as described in Schemes 1-12 can be used to prepare the compounds of Formula 1. The definitions of A, $R^1$, $Q^1$, $J^1$, $R^2$, $Q^2$, $J^2$, B, LG, $R^a$ in the compounds of Formulae 1-24 below are as defined above in the Summary of the Invention unless otherwise noted. Compounds of Formulae 1a-1h and 4a-4b are various subsets of the compounds of Formula 1 and 4, and all substituents for Formulae 1a-1h and 4a-4b are as defined above for Formula 1 and 4 unless otherwise noted.

As shown in Scheme 1, a compound of Formula 1a (i.e. a compound of Formula 1 wherein X is $R^1$, Y is -$Q^1$-$J^1$ and $Q^1$ is carbonyl) can be prepared by oxidation of a compound of Formula 1b (i.e. a compound of Formula 1 wherein X is $R^1$, Y is -$Q^1$-$J^1$ and $Q^1$ is CH(OH)) using a wide variety of reagents with the general methods well known to one skilled in the art. Examples of these methods are described in the following references and those cited therein; *Tetrahedron* 2013, 69, 5568-5972; *Eur. J. Org. Chem.* 2014, 781-787 and Burke, S. D., Ed. *Handbook of Reagents for Organic Synthesis, Oxidizing and Reducing Agents*; John Wiley & Sons, Chichester, UK, 1999. The simplest procedure uses commercially available activated manganese dioxide ($MnO_2$) in refluxing toluene under an oxygen or nitrogen atmosphere. The amount of activated manganese dioxide can range from sub-stoichiometric to excess.

Scheme 1

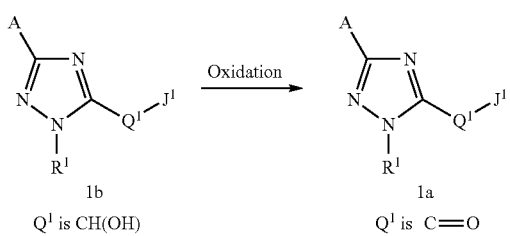

As shown in Scheme 2, a compound of Formula 1c (i. e. a compound of Formula 1 wherein X is $R^1$, Y is $Q^1$-$J^1$ and $Q^1$ is $CH_2$) can be prepared by reduction of a compound of Formula 1b using a wide variety of reagents with the general methods well known to one skilled in the art. Examples of these methods are described in the following references and those cited therein; *Tetrahedron Lett.* 2001, 42, 831-833. Particularly useful method is using hydrogen iodide generated from hypophosphorous acid ($H_3PO_2$) and iodine in preferably acetic acid as solvent at a temperature ranging from 40° C. to reflux.

Scheme 2

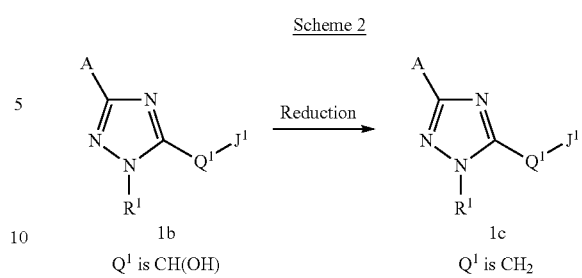

As shown in Scheme 3, a compound of Formula 1b or 1a can be prepared by the addition of an organic lithium or magnesium reagent of Formula 2 to a carbonyl containing compound of Formula 3 at a temperature ranging from −78° C. to room temperature in a solvent such as tetrahydrofuran. The compound of Formula 2 is either commercially available or can be prepared by methods known in the art.

Scheme 3

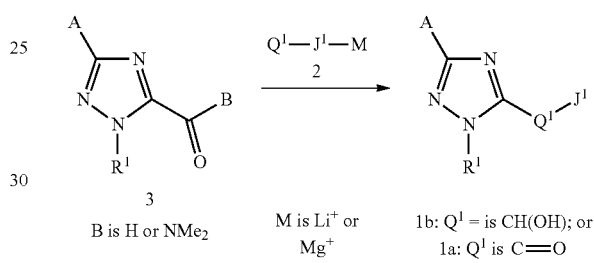

As shown in Scheme 4, compounds of Formulae 1e-1g (i.e. a compound of Formula 1 wherein X is $R^1$, Y is -$Q^1$-$J^1$; and $Q^1$ is O for 1e; is S for 1f; and $Q^1$ is $NR^6$ for 1g) can be prepared by the reaction of a compound of Formula 4 with an oxygen, sulfur or nitrogen nucleophile of Formula 5 (i.e. an alcohol, a thiol or an amine) in the presence of a base such as sodium hydride, cesium carbonate or potassium tert-butoxide in a solvent such as dimethyl sulfoxide, N,N-dimethylformamide, tetrahydrofuran or acetonitrile at a temperature ranging from ambient to reflux.

Scheme 4

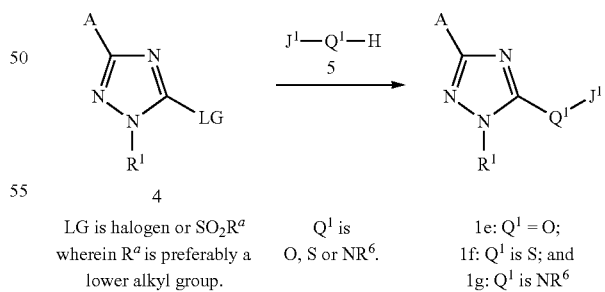

As shown in Scheme 5, a compound of Formula 4a (a subset of Formula 4 wherein LG is $SO_2R^a$) can be prepared from a compound of Formula 6 using the general methods well known to one skilled in the art. For example, a thioalkyl of Formula 6 can be oxidized to the corresponding sulfonyl of Formula 4a using a wide variety of reagents such as 3-chloroperoxybenzoic acid (MCPBA) or potassium peroxymonosulfate (e.g., Oxone®). Typically, these oxidations are performed in solvents such as dichloromethane (for MCPBA) or acetone and water (for Oxone®) at a temperature ranging from 0° C. to ambient temperature. For a comprehensive overview of the methodologies available to oxidize sulfides, see Larock, R. C., *Comprehensive Organic Transformations: A Guide to Functional Group Preparations*, 2nd Ed., Wiley-VCH, New York, 1999 and references cited therein.

Scheme 5

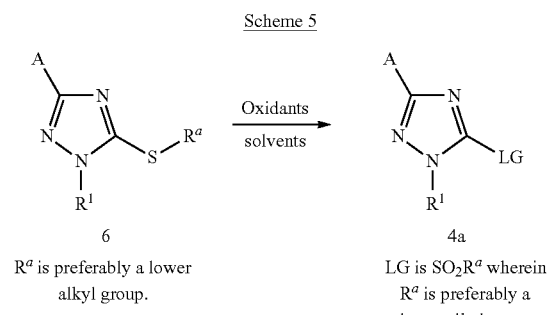

A compound of Formula 6 can be prepared using the reaction sequence described in *Aust. J. Chem.* 1997, 50, 911 as shown in Scheme 6. The reaction sequence starts with the condensation of an aldehyde of Formula 7 with a 2-alkyl-3-thiosemicarbazide of Formula 8, followed by alkylation with alkyl halide (wherein the alkyl is $R^a$) to yield the intermediate of Formula 9. Ring closure of intermediate of the compound Formula 9 with iron (III) chloride in acetic acid and water affords the compound of Formula 6.

Scheme 6

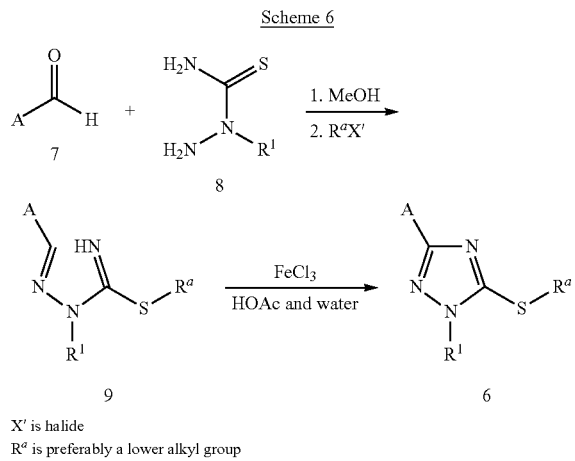

As shown in Scheme 7, a compound of Formulae 3, 6, 4b and 10 can be prepared by treating a compound of Formula 11 with organo lithium reagents such as n-butyllithium at a temperature of −78° C. and quenched with a variety of electrophiles such as N,N-dimethylformamide, alkyl formate, N,N-dialkylcarbamoyl chlorides, dialkyl disulfides, halogenating agents or $CO_2$.

Scheme 7

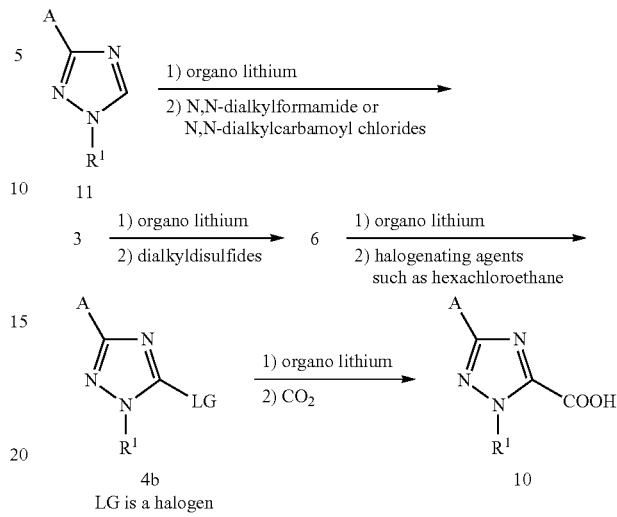

A 1,3-disubstituted 1,2,4-triazole of Formula 11 is either commercially available or can be prepared by the reaction sequence described in the literature, for example, see WO2010/074588 or as shown in Scheme 8. A compound of Formula 13 (i.e. a commercially available benzamide or heteroaromatic amide), refluxed in N,N-dimethylformamide dimethylacetal (DMF-DMA), is then treated with hydrazine monohydrate and heated to reflux in acetic acid to provide 5-substituted 1,2,4-triazole. The 5-substituted 1,2,4-triazole is then alkylated predominantly on N1 with bases such as potassium carbonate, triethylamine, sodium hydride or sodium hydroxide and various alkylating reagents (i.e. $R^1X$), preferably an alkyl iodide in solvents such as N,N-dimethylformamide, dimethylsulfoxide or tetrahydrofuran to prepare a compound of Formula 11, at a temperature ranging from ambient temperature to the reflux temperature of the solvent. Other methods for the preparation of the compound of Formula 11 can be found in *Science of Synthesis*, Georg Thieme Verlag New York, Category 2: Hetarenes and Related Ring Systems, Volume 13; Five-Membered Hetarenes with Three or More Heteroatoms, Product Class 14: 1,2,4-Triazoles by A. D. M. Curtis, 2004, 603-640 and *J. Org. Chem.* 2011, 76, 1177-1179.

Scheme 8

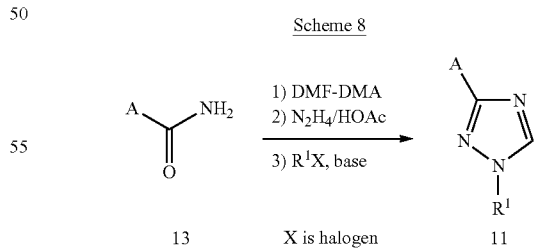

As shown in Scheme 9, a compound of Formula 1h (i.e. a compound of Formula 1 wherein X is $-Q^2-J^2$ and Y is $R^2$) can be prepared by nucleophilic substitution by heating a compound of Formula 14 in a suitable solvent such as acetonitrile, tetrahydrofuran or N,N-dimethylformamide in the presence of a base such as potassium carbonate or cesium carbonate, with a compound of Formula 15. The reaction is typically conducted at a temperature ranging from room temperature to 110° C.

Scheme 9

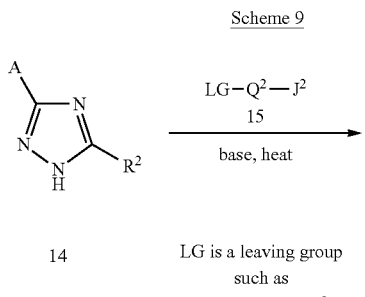

14  LG is a leaving group such as halogen or SO₂Rᵃ.  1h

As shown in Scheme 10, a compound of Formula 14 can be prepared by the method described in *J. Am. Chem. Soc.* 2009, 131, 15080-15801. An amidine of Formula 16 is combined with a phenyl or heteroaromatic nitrile of Formula 17 and heated at 120° C., open to the air in a suitable solvent such as dimethylsulfoxide, N,N-dimethylacetamide or N,N-dimethylformamide in the presence of a base such as potassium carbonate or cesium carbonate and a catalytic amount of copper (I) bromide to afford a compound of Formula 14. Other methods for the preparation of a compound of Formula 14 can be found in *Science of Synthesis*, Georg Thieme Verlag New York, Category 2: Hetarenes and Related Ring Systems, Volume 13-Five-Membered Hetarenes with Three or More Heteroatoms, Product Class 14: 1,2,4-Triazoles by A. D. M. Curtis, 2004 pp. 603-640.

Scheme 10

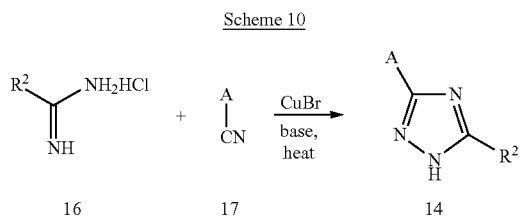

16      17      14

As shown in Scheme 11, a compound of Formula 1h can alternatively be prepared by the reaction of a 1,2,4-triazole derivative of Formula 18 wherein LG is a leaving group such as SO₂R (wherein R is alkyl, haloalkyl, phenyl or p-tolyl), with a wide range of carbon, nitrogen, oxygen and sulfur nucleophiles including cyanide, amines, alcohols and thiols optionally in the presence of a base and a solvent. Typical bases including sodium hydride, cesium carbonate, potassium carbonate or potassium tert-butoxide can be employed. Solvents suitable for this substitution reaction are dimethylsulfoxide, N,N-dimethylformamide, tetrahydrofuran and acetonitrile. Reaction temperature ranges from ambient temperature to the reflux temperature of the solvent.

Scheme 11

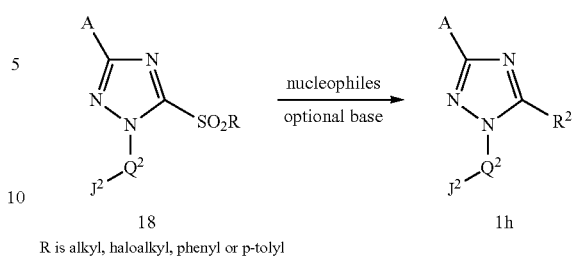

18  1h

R is alkyl, haloalkyl, phenyl or p-tolyl

A compound of Formula 18 can be prepared by the reaction sequence shown below in Scheme 12. A compound of Formula 19 (i.e. a 4H-1,2,4-triazole-3-thiol), is commercially available or can be prepared using the methods known in the art. The compound of Formula 19 is alkylated on the thiol atom at 3-position using an alkylating reagent (i.e. R-LG wherein LG is a leaving group such as halogen or sulfonyl) in a suitable solvent such as dimethylsulfoxide, N,N-dimethylformamide at room temperature to afford intermediate 20. The Intermediate of Formula 20 is then N-alkylated to give the compound of Formula 21 using the methods described in Scheme 9. The compound of Formula 21 can be oxidized to the compound of Formula 18 using a wide variety of reagents such as 3-chloroperoxybenzoic acid (MCPBA) or potassium peroxymonosulfate such as Oxone®. Typically, these oxidations are performed in solvents such as dichloromethane (for MCPBA) or acetone and water (for Oxone®) at a temperature ranging from 0° C. to the room temperature. For a comprehensive overview of the methodologies available to oxidize sulfides, see Larock, R. C., *Comprehensive Organic Transformations: A Guide to Functional Group Preparations*, 2nd Ed., Wiley-VCH, New York, 1999; and references cited therein.

Scheme 12

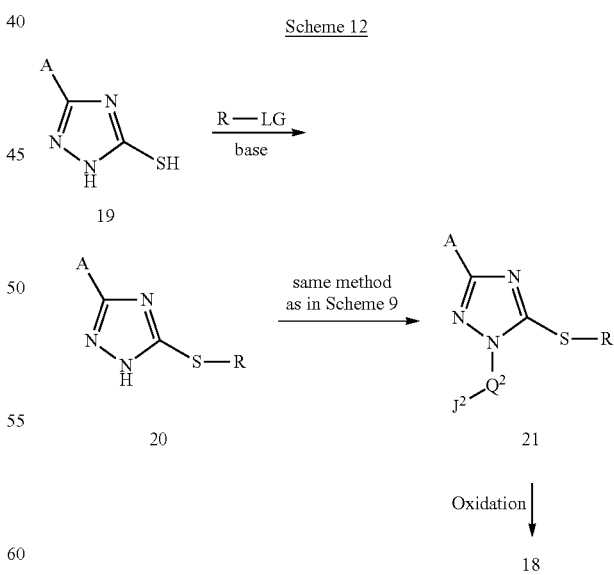

LG is a leaving group such as halogen or SO₂Rᵃ; and R is alkyl, haloalkyl, phenyl or p-tolyl Compounds of Formula 19, can be prepared by the literature methods described in *J. Med. Chem.* 1994, 37, 125-132 and as shown in Scheme 13 below. An aroyl chloride of Formula 22 can be added to a thiosemicarbazide of Formula 23 in the presence of a base such as pyridine or triethylamine to form the acylated thiosemicarbazide of Formula 24. The thiosemicarbazides of Formula 24 can be cyclized with a base such as potassium carbonate, triethylamine, sodium hydride or an aqueous hydroxide base to form the compound of Formula 19. The synthetic procedure outlined in Scheme 13 is described in Steps A and B of Synthesis Example 6.

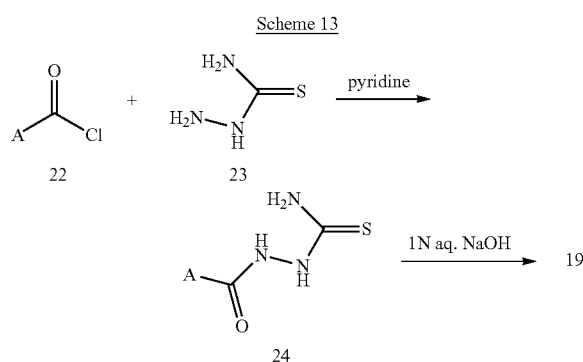

The skilled artisan will appreciate that a compound of Formula 19 can exist in a variety of tautomeric forms, such as a compound of Formulae 19A, 19B and 19C.

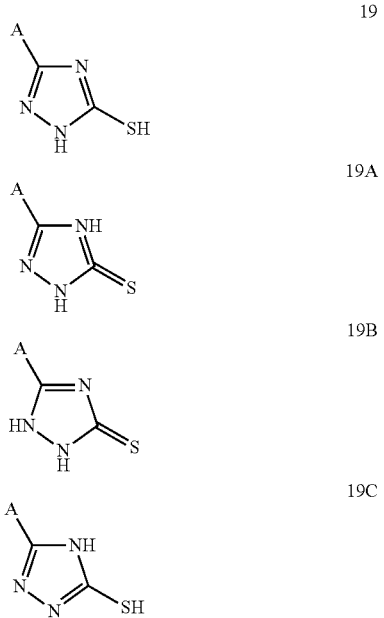

The specific tautomer drawn may not be the lowest energy tautomer present based on many factors including such as the value of variable "A", and the physical form (i.e. solid or dissolved in solution).

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ unless otherwise noted; "s" means singlet, "d" means doublet, "t" means triplet, "q" means quartet, "bs" means broad singlet and "m" means multiplet. Mass spectra are reported as the molecular weight of the highest isotopic abundance parent ion (M+1) formed by addition of $H^+$ (molecular weight of 1) to the molecule, or (M−1) formed by the loss of $H^+$ (molecular weight of 1) from the molecule, observed by using liquid chromatography coupled to a mass spectrometer (LCMS) using either atmospheric pressure chemical ionization ($AP^+$) or electrospray ionization ($ES^+$ or $ES^-$).

Synthesis Example 1

Preparation of 4-[[5-ethyl-3-[4-(trifluoromethyl)phenyl]-1H-1,2,4-triazol-1-yl]methyl]-2-(trifluoromethyl)pyridine (Compound 1)

Step A: Preparation of 2-trifluoromethyl-pyridin-4-yl methylbromide

A solution of 2-trifluoromethyl-pyridin-4-yl methanol (0.5 g, 2.8 mmol) in 14.0 mL of dichloromethane was stirred under a nitrogen atmosphere and cooled to a temperature below 10° C. using an ice-water bath. Phosphorous tribromide (0.76 g, 2.8 mmol) was added and the reaction mixture was stirred at ambient temperature for 16 h. After the reaction was completed, the mixture was poured into an ice-water and saturated sodium bicarbonate aqueous solution. The aqueous layer was separated and extracted three times with dichloromethane. The combined organic layers were washed with brine, dried over MgSO$_4$, filtered and concentrated to give the title compound (0.39 g).

$^1$H NMR δ 8.71 (d, 1H), 7.71 (s, 1H), 7.52 (d, 1H), 4.46 (s, 2H).

Step B: Preparation of 3-ethyl-5-[4-(trifluoromethyl)phenyl]-1H-1,2,4-triazole To a solution of propionamidine hydrochloride (1.90 g, 17.5 mmol) and α,α,α-trifluoro-p-tolunitrile (2.0 g, 11.7 mmoles) in 30 mL of dimethylsulfoxide was added cesium carbonate (11.4 g, 34.9 mmol) and copper(I) bromide (0.3 g, 1.05 mmol) and the mixture was stirred and heated at 120° C. for 16 h, open to the air. After the reaction was completed, the reaction mixture was cooled and diluted with water, quenched with saturated aqueous sodium bicarbonate solution and extracted with ethyl acetate. The aqueous layer was separated and extracted twice with ethyl acetate. The combined ethyl acetate layers were washed with saturated EDTA aqueous solution and brine, dried over MgSO$_4$ and concentrated to give 1.69 g of crude solid. The crude solid was dissolved in diethyl ether. A white solid was filtered off as by-product, 177 mg of intermediate 4-trifluoromethyl benzamide. The filtrate was concentrated and the residue was purified by a 40 gram silica gel column eluting with a gradient of 10%, 25%, 50% ethyl acetate in hexanes to give the title compound as a solid (0.57 g).

$^1$H NMR δ 8.20 (d, 2H), 7.69 (d, 2H), 2.90 (q, 2H), 1.42 (t, 3H).

Step C: Preparation of 4-[[5-ethyl-3-[4-(trifluoromethyl)phenyl]-1H-1,2,4-triazol-1-yl]methyl]-2-(trifluoromethyl)pyridine To a solution of 3-ethyl-5-[4-(trifluoromethyl)phenyl]-1H-1,2,4-triazole (i.e. the product of Step B) (0.21 g, 0.88 mmol) and 2-(trifluoromethyl-pyridin-4yl) methylbromide (i.e. the product of Step A) (0.23 g, 0.971 mmol) in N,N-dimethylformamide (2.0 mL) under a nitrogen atmosphere was added powdered potassium carbonate (0.31 g, 2.21 mmol) and the reaction mixture was stirred at ambient temperature for 16 h. Then the reaction was diluted with water and diethyl ether and the layers were separated. The aqueous layer was extracted twice with diethyl ether. The organic layers were combined and washed three times with water, dried over MgSO$_4$, filtered and concentrated to afford 0.28 g of oil as crude product. The crude product was purified using a 12 g silica gel column eluting with a gradient of 10% to 30% of ethyl acetate in hexanes to give the title compound (0.22 g).

$^1$H NMR δ 8.72 (d, 1H), 8.21 (d, 2H), 7.68 (d, 2H), 7.53 (s, 1H), 7.25 (d, 1H), 5.44 (s, 2H), 2.79 (q, 2H), 1.37 (t, 3H).

(Comparative) Synthesis Example 2

Preparation of 3-(4-fluorophenyl)-1-methyl-5-[3-(trifluoromethyl)phenoxy]-1H-1,2,4-triazole (Compound 5)

Step A: Preparation of methyl 2-[(4-fluorophenyl)methylene]-1-methylhydrazinecarboximidothioate A solution of 4-fluorobenzaldehyde (2.5 g, 20 mmol) and 2-methyl-3-thiosemicarbazide (2.12 g, 20.1 mmol) in methanol (100 mL) was stirred under a nitrogen atmosphere at reflux overnight. Then the reaction mixture was cooled to 0° C. and iodomethane (15.72 g, 110.8 mmol) was added. The reaction mixture was stirred at room temperature for 3 d. The white solid that precipitated was filtered off and vacuum-line dried to afford the title compound (2.2 g).

MS (ES$^+$) 225.9 (M+1).

Step B: Preparation of 3-(4-fluorophenyl)-1-methyl-5-(methylthio)-1H-1,2,4-triazole To a solution of methyl 2-[(4-fluorophenyl)methylene]-1-methylhydrazinecarboximidothioate (i.e. the product of Step A) (2.2 g, 9.8 mmol) in acetic acid (60 mL) and water (60 mL) was added a solution of iron (III) chloride (5.23 g, 32.22 mmol) in water (60 mL) dropwise through an additional funnel. The reaction mixture was heated to reflux for 4 h. After a complete reaction, the reaction mixture was cooled to room temperature. Toluene was added and removed using rotavapor. The residue was neutralized to pH=8 with saturated aqueous NaHCO$_3$ and Na$_2$CO$_3$ solutions. The resulting mixture was extracted with ethyl acetate. The ethyl acetate layer was washed with brine, dried and concentrated to afford 1.6 g of a solid. The solid was washed with hexanes to afford the title compound (0.69 g).

$^1$H NMR δ 8.40 (m, 2H), 7.09 (t, 2H), 3.80 (s, 3H), 2.74 (s, 3H).

Step C: Preparation of 3-(4-fluorophenyl)-1-methyl-5-(methyl sulfonyl)-1H-1,2,4-triazole A solution of 3-(4-fluorophenyl)-1-methyl-5-(methylthio)-1H-1,2,4-triazole (i.e. the product of Step B) (0.6 g, 2.60 mmol) in dichloromethane (30 mL) was stirred and cooled to 0° C. with an ice-acetone bath. MCPBA (1.5 g, 6.5 mmol) was added to the solution. The reaction mixture was stirred at room temperature overnight. The reaction was diluted with saturated NaHCO$_3$ aqueous solution. The aqueous layer was separated and extracted with dichloromethane. All the organic layers were combined and washed with saturated NaHCO$_3$ aqueous solution, brine, dried over MgSO$_4$ and concentrated to afford 0.4 g of a solid. The solid was washed with hexanes to provide the title compound (268 mg).

$^1$H NMR δ 8.08 (m, 2H), 7.13 (t, 2H), 4.23 (s, 3H), 3.48 (s, 3H).

Step D: Preparation of 3-(4-fluorophenyl)-1-methyl-5-[3-(trifluoromethyl)phenoxy]-1H-1,2,4-triazole To a solution of 3-(4-fluorophenyl)-1-methyl-5-(methyl sulfonyl)-1H-1,2,4-triazole (i.e. the product of Step C) (134 mg, 0.525 mmol) in N,N-dimethylformamide (0.75 mL) was added α,α,α-trifluoro-m-cresol (110 mg, 0.682 mmol) and potassium carbonate (145 mg, 1.05 mmol). After the reaction mixture was heated at 100° C. for 5 h, it was cooled down to room temperature and allowed to stand for 16 h. Then the reaction mixture was diluted with water and diethyl ether. The aqueous layer was separated and extracted with diethyl ether (2×). All the organic layers were combined and washed with water (3×), 1 N NaOH solution, brine, dried over Na$_2$SO$_4$ and concentrated to afford the title compound (190 mg).

$^1$H NMR δ 7.97 (m, 2H), 7.69 (s, 1H), 7.61 (d, 1H), 7.48-7.58 (m, 2H), 7.08 (t, 2H), 3.84 (s, 3H).

Synthesis Example 3

Preparation of 4-[[3-(4-(fluorophenyl)-1-methyl-1H-1,2,4-triazol-5-yl]methyl]-2-(trifluoromethyl)pyridine (Compound 13)

Step A: Preparation of N-[(dimethylamino)methylene]-4-fluoro benzamide

A solution of fluorobenzamide (10 g, 71.9 mmol) in DMF-DMA (21.4 g, 180 mmol) was heated at 80° C. for 1 h. Then the reaction mixture was cooled down and concentrated to give a white solid. The resulting white solid was washed with hexanes to afford the title compound (12.72 g).

$^1$H NMR δ 8.63 (s, 1H), 8.30 (m, 2H), 7.07 (t, 2H), 3.21 (s, 3H), 3.19 (s, 3H).

Step B: Preparation of 5-(4-fluorophenyl)-1H-1,2,4-triazole

To a solution of N-[(dimethylamino)methylene]-4-fluoro benzamide (i.e. the product of Step A) (12.7 g, 65.5 mmol) in acetic acid was added hydrazine monohydrate (3.6 g, 72 mmol) at ambient temperature. After the reaction exothermed to 90° C., the reaction mixture was heated at 120° C. for 2 h. The reaction was then cooled down to room temperature and concentrated. Toluene was added to the residue and then concentrated to afford an oil. A solid was triturated from water and washed with hexanes to afford the title compound (10.6 g).

$^1$H NMR (DMSO-$d_6$) δ 8.45 (s, 1H), 8.05 (m, 2H), 7.32 (m, 2H).

Step C: Preparation of 3-(4-fluorophenyl)-1-methyl-1H-1,2,4-triazole

To a solution of 5-(4-fluorophenyl)-1H-1,2,4-triazole (i.e. the product of Step B) (5.0 g, 30.65 mmol) in N,N-dimethylformamide was added potassium carbonate (10.6 g, 76.6 mmol) and iodomethane (15.2 g, 107 mmol). The reaction mixture was stirred at ambient temperature for 16 h. The reaction was then diluted with water and diethyl ether. The aqueous layer was separated and extracted with diethyl ether (2×). The organic layers were then combined and washed with water (3×), brine, concentrated and the residue was re-dissolved in dichloromethane, dried over MgSO$_4$, filtered and concentrated to afford a solid. The solid was washed with hexanes to obtain the title compound (1.16 g).

$^1$H NMR δ 8.07 (m, 2H), 8.04 (s, 1H), 7.12 (m, 2H), 3.96 (s, 3H).

Step D: Preparation of 3-(4-fluorophenyl)-1-methyl-1H-1,2,4-triazole-5-carboxaldehyde To a solution of 1-methyl-3-(4-fluorophenyl)-1H-1,2,4-triazole (i.e. the product of Step C) (1.35 g, 7.62 mmol) in tetrahydrofuran (15 mL) was added 2.5 M n-butyllithium in hexanes (3.35 mL, 8.38 mmoles) at −78° C. via a syringe through a septa, maintaining the temperature below −50° C. The reaction mixture was stirred at −78° C. for 2 h. N,N-dimethylformamide (1.1 mL, 13.71 mmol) was added and the reaction was allowed to warm to 0° C., followed by quenching the reaction with saturated aqueous NH$_4$Cl solution (25 mL). The reaction mixture was extracted with ethyl acetate (3×). All the organic layers were combined and washed with brine, dried over MgSO$_4$, filtered and concentrated to afford 1.38 g of a solid. The solid was washed with hexanes to obtain the title compound (1.01 g).

$^1$H NMR δ 10.04 (s, 1H), 8.11 (m, 2H), 7.16 (t, 2H), 4.25 (s, 3H).

Step E: Preparation of α-[3-(4-fluorophenyl)-1-methyl-1H-1,2,4-triazol-5-yl]-2-(trifluoromethyl)-4-pyridinemethanol A solution of 4-iodo-2-(trifluoromethyl)pyridine (0.49 g, 1.82 mmoles) in tetrahydrofuran (3 mL) was cooled to 0° C. and 1.3 M isopropyl magnesium chloride lithium chloride in tetrahydrofuran (1.55 mL, 1.99 mmol) was added via a syringe through a septa at a temperature below 5° C. The reaction mixture was stirred at room temperature for 1 h. The reaction mixture was then cooled to −78° C. and added to 3-(4-fluorophenyl)-1-methyl-1H-1,2,4-triazole-5-carboxaldehyde (i.e. the product of Step D) (0.34 g, 1.65 mmoles) in 3 mL of tetrahydrofuran which was also cooled to −78° C. prior to the addition. The reaction mixture was allowed to warm to ambient temperature and quenched with saturated NH$_4$Cl aqueous solution. The resulting mixture was extracted with ethyl acetate (2×). The combined organic layers were washed with brine, dried over MgSO$_4$, filtered and concentrated to afford 0.57 g solid residue. The residue was purified through a 12 silica gel column eluting with 30% to 32% ethyl acetate in hexanes to provide the title compound (0.31 g).

$^1$H NMR δ 8.77 (d, 1H), 8.02 (m, 2H), 7.81 (s, 1H), 7.52 (d, 1H), 7.14 (t, 2H), 6.17 (s, 1H), 4.06 (bs, 1H), 3.72 (s, 3H).

Step F: Preparation of 4-[[3-(4-fluorophenyl)-1-methyl-1H-1,2,4-triazol-5-yl]methyl]-2-(trifluoromethyl)pyridine To a solution of α-[3-(4-fluorophenyl)-1-methyl-1H-1,2,4-triazol-5-yl]-2-(trifluoromethyl)-4-pyridinemethanol (i.e. the product of Step E) (0.25 g, 0.709 mmoles) in acetic acid (3 mL) was added iodine (360 mg, 1.42 mmol) and then hypophosphorous acid (187 mg, 2.83 mmol). The reaction mixture was heated at 110° C. for 16 h. More iodine (360 mg) and hypophosphorous acid (187 mg) were added the next day and heating was continued at 110° C. for 16 h. The reaction was cooled to 0° C. and diluted with 1 N NaOH aqueous solution and saturated aqueous NaHCO$_3$ solution. The reaction mixture was extracted with ethyl acetate (3×). The combined organic layers were washed with brine, dried over MgSO$_4$, filtered and concentrated to give 0.12 g oil. The oil was purified through a 12 g silica gel column eluting with 10% ethyl acetate in dichloromethane to give the title compound (60 mg).

$^1$H NMR δ 8.70 (d, 1H), 8.05 (m, 2H), 7.61 (s, 1H), 7.40 (d, 1H), 7.12 (t, 2H), 4.28 (s, 2H), 3.83 (s, 3H).

Synthesis Example 4

Preparation of 4-[[5-ethoxy-3-(4-fluorophenyl)-1H-1,2,4-triazol-1-yl]methyl]-2-(trifluoromethyl)pyridine (Compound 8)

Step A: Preparation of 4-[[3-(4-fluorophenyl)-5-(methylthio)-1H-1,2,4-triazole-1-yl]methyl]-2-(trifluoromethyl)pyridine To a solution of 5-(4-fluorophenyl)-4H-1,2,4-triazole-3-thiol (2.5 g, 12.8 mmol) in N,N-dimethylformamide (30 mL) was added powdered potassium carbonate (4.45 g, 32.2 mmol) followed with iodomethane (2.0 g, 14.10 mmol). The mixture was stirred at ambient temperature for 16 h. The reaction was then diluted with water and diethyl ether. The aqueous layer was separated and extracted with diethyl ether (2×). The combined organic layers were washed with water (2×), brine and concentrated. The resulting residue was then dissolved in ethyl acetate and dried over MgSO$_4$, filtered and concentrated. The resulting residue was purified with a 40 g silica gel column eluting with 10% to 20% ethyl acetate in hexanes to give 2.8 g of solid. The solid was washed with hexanes and filtered to obtain the title compound (1.6 g).

$^1$H NMR δ 8.10 (m, 2H), 7.26 (t, 2H), 2.68 (s, 3H).

Step B: Preparation of 3-(4-fluorophenyl)-1H-1,2,4-triazol-1-yl]methyl]-2-(trifluoromethyl)pyridine To a solution of 3-(4-fluorophenyl)-5-(methylthio)-1H-1,2,4-triazole (i.e. the product of Step A) (1.6 g, 7.65 mmol) and 2-trifluoromethyl-pyridin-4-yl methylbromide (i.e. the product of Step A in Synthesis Example 1) (2.3 g, 8.4 mmol) in N,N-dimethylformamide was added powdered potassium carbonate (2.6 g, 19.12 mmol). The mixture was stirred at ambient temperature for 16 h. Then the reaction was diluted with water and diethyl ether. The aqueous layer was separated and extracted with diethyl ether (2×). The combined organic layers were washed with water (2×), brine, dried over Na$_2$SO$_4$, filtered and concentrated to give 3.3 g of oil. The oil was purified through a 40 g silica gel column eluting with a gradient of 20% to 40% ethyl acetate in hexanes to provide the title compound as a white solid (1.81 g).

$^1$H NMR δ 8.72 (d, 1H), 8.06 (m, 2H), 7.59 (s, 1H), 7.33 (d, 1H), 7.12 (t, 2H), 5.35 (s, 2H), 2.78 (s, 3H).

Step C: Preparation of 4-[[3-(4-fluorophenyl)-5-(methyl sulfonyl)-1H-1,2,4-triazole-1-yl]methyl]-2-(trifluoromethyl)pyridine To a solution of 3-(4-fluorophenyl)-1H-1,2,4-triazol-1-yl]methyl]-2-(trifluoromethyl)pyridine (i.e. the product of Step B) (0.5 g, 1.4 mmol) in dichloromethane (9.6 mL) was added MCPBA (0.78 g, 3.4 mmol) at room temperature and stirred overnight. The reaction mixture was then diluted with saturated NaHSO$_3$ aqueous solution and dichloromethane. The aqueous layer was separated and extracted with dichloromethane. All organic layers were combined and washed with saturated NaHSO$_3$ aqueous solution (1×), NaHCO$_3$ aqueous solution (2×), brine, dried over magnesium sulfate, filtered and concentrated to give 0.57 g white solid. The white solid was washed with hexanes to obtain the title compound (418 mg).

$^1$H NMR δ 8.78 (d, 1H), 8.19 (m, 2H), 7.74 (s, 1H), 7.52 (d, 1H), 7.15 (t, 2H), 5.79 (s, 2H), 3.49 (s, 3H).

Step D: Preparation of 4-[[5-ethoxy-3-(4-fluorophenyl)-1H-1,2,4-triazol-1-yl]methyl]-2-(trifluoromethyl)pyridine Sodium hydride (60% dispersion in oil) (22 mg, 0.55 mmol) was dissolved in ethanol (1.5 mL) and stirred for about fifteen minutes before a solution of 4-[[3-(4-fluorophenyl)-5-(methyl sulfonyl)-1H-1,2,4-triazole-1-yl]methyl]-2-(trifluoromethyl)pyridine (i.e. the product of Step C) (0.20 g, 0.50 mmoles) in N,N-dimethylformamide (1.5 mL) was added. The reaction mixture was heated to 65° C. for 3 h before the reaction was allowed to stand at ambient temperature for 16 h. The reaction was then diluted with water and a white solid precipitated. The white solid was separated by filtration and rinsed well with water followed by hexanes. The solid was dried with vacuum to obtain the title compound (76 mg).

$^1$H NMR δ 8.71 (d, 1H), 7.99 (m, 2H), 7.60 (s, 1H), 7.37 (d, 1H), 7.10 (t, 2H), 5.22 (s, 2H), 4.58 (t, 2H), 1.46 (t, 3H).

Synthesis Example 5

Preparation of [1-ethyl-3-(4-fluorophenyl)-1H-1,2,4-triazol-5-yl][2-(trifluoromethyl)-4-pyridinyl]methanone (Compound 19)

Step A: Preparation of [1-ethyl-3-(4-fluorophenyl)-1H-1,2,4-triazol-5-yl][2-(trifluoromethyl)-4-pyridinyl]methanone α-[1-Ethyl-3-(4-fluorophenyl)-1H-1,2,4-triazol-5-yl]-2-(trifluoromethyl)-4-pyridinemethanol (prepared in a similar manner as described above in Example above, 3200 mg, 0.55 mmol) and manganese(IV) oxide (1.8 g, 21 mmol) were combined and the resulting mixture was heated at the reflux temperature of the solvent for 3 h. The mixture was cooled and allowed to stand at ambient temperature overnight. The mixture was filtered through a pad of Celite® diatomaceous earth filter aid and rinsed well with ethyl acetate. The filtrate was concentrated to provide 0.17 g of an oil which was purified by silica gel chromatography using a gradient of 10-30% ethyl acetate in dichloromethane to give 30 mg of the title compound as a solid.

$^1$H NMR δ 9.01 (d, 1H), 8.71 (s, 1H), 8.57 (d, 1H), 8.13 (m, 2H), 7.17 (t, 2H), 4.73 (q, 2H), 1.62 (t, 3H).

Synthesis Example 6

Preparation of 4-[[5-ethoxy-3-[4-(trifluoromethyl)phenyl]-1H-1,2,4-triazole-1-yl]methyl]-2-(trifluoromethyl)pyridine (Compound 35)

Step A: Preparation of benzoic acid, 4-(trifluoromethyl), 2-(aminothiocarbonyl) hydrazide Thiosemicarbazide (1.99 g, 21.79 mmol) was dissolved in 20 mL of pyridine under a nitrogen atmosphere. The reaction mixture was cooled using an ice-water bath. 4-(Trifluoromethyl)benzoyl chloride (5 g, 23.97 mmol) was added dropwise via an addition funnel, maintaining the temperature below 5° C. The resulting yellow suspension was stirred at ambient temperature for 16 h. The reaction mixture was diluted with excess dichloromethane and then concentrated under reduced pressure to yield a solid. De-ionized water was added directly to the residue. The solid was then filtered off and rinsed well with de-ionized water followed by hexanes. The solid was air-dried to obtain 7.64 g of the title compound.

$^1$H NMR (DMSO) δ 9.41 (bs, 1H), 8.64 (bs, 1H), 8.08 (d, 2H), 7.93 (m, 1H), 7.88 (d, 2H), 7.76 (bs, 1H), 8.50 (t, 1H).

Step B: Preparation of 1,2-dihydro-5-[4-(trifluoromethyl)phenyl]-3H-1,2,4-triazole-3-thione To 1.6 g of benzoic acid, 4-(trifluoromethyl), 2-(aminothiocarbonyl) hydrazide (i.e. the product obtained in Step A, 6.08 mmol) was added 1.0 mL of 1 N NaOH aqueous solution dissolved in 9 mL of de-ionized water. The mixture was heated to the reflux temperature of the solvent for 2.5 h. The mixture was cooled to ambient temperature and acetic acid was added, followed by de-ionized water. The resulting precipitate was filtered off and the solid was rinsed with de-ionized water followed by hexanes. The solid was air-dried to yield 2.84 g of the title compound as a white solid.

$^1$H NMR (DMSO) δ 8.13 (d, 2H), 7.91 (d, 2H).

Step C: Preparation of 5-(methylthio)-3-[4-(trifluoromethyl)phenyl]-1H-1,2,4-triazole 1,2-Dihydro-5-[4-(trifluoromethyl)phenyl]-3H-1,2,4-triazole-3-thione (i.e. the product from Step B above, 2.8 g, 11.42 mmol) was dissolved in 30 mL of N,N-dimethylformamide under a nitrogen atmosphere. Powdered potassium carbonate (3.94 g, 28.54 mmol) was added, followed by iodomethane (1.78 g, 12.56 mmol). The resulting mixture was stirred at ambient temperature overnight. The reaction was diluted with de-ionized water and diethyl ether. The layers were separated and the layer extracted with diethyl ether (3×). The combined organic layers were washed three times with de-ionized water, and once with brine. The organic layer was dried over sodium sulfate, filtered and concentrated to obtain 4.02 g of a solid. The solid was suspended in hexanes, and the mixture was filtered to provide a white solid (1.95 g).

$^1$H NMR δ 8.18 (d, 2H), 7.71 (d, 2H), 2.74 (s, 3H).

Step D: Preparation of 4-[[5-(methylthio)-3-[4-(trifluoromethyl)phenyl]-1H-1,2,4-triazole-1-yl]methyl]-2-(trifluoromethyl)pyridine 5-(Methylthio)-3-[4-(trifluoromethyl)phenyl]-1H-1,2,4-triazole (i.e. the product obtained in Step C, above, 1.32 g, 5.08 mmol) was dissolved in 16 mL of N,N-dimethylformamide under a nitrogen atmosphere. To this mixture was added powdered potassium carbonate (1.75 g, 12.69 mmol) followed by 2-trifluoromethyl-pyridin-4-yl methylbromide (i.e. the product of Example 1, Step A, 1.34 g, 5.58 mmol). The resulting mixture was stirred at ambient temperature for 16 h. The reaction mixture was diluted with de-ionized water and diethyl ether. The aqueous layer was separated and extracted three times with diethyl ether. The combined organic layers were washed three times with de-ionized water, followed by brine. The organic layer was dried over sodium sulfate, filtered and concentrated to yield 2.81 g of an oil. Purification with silica gel column chromatography using a gradient of hexanes to 20% ethyl acetate in hexanes yielded 1.82 g of the title compound as a yellow solid. The yellow solid was collected from hexanes and diethyl ether to provide the title compound as a solid (1.22 g).

$^1$H NMR δ 8.72 (d, 1H), 8.20 (d, 2H), 7.69 (d, 2H), 7.59 (s, 1H), 7.34 (d, 1H), 5.38 (s, 2H), 2.79 (s, 3H).

Step E: Preparation of 4-[[5-(methyl sulfonyl)-3-[4-(trifluoromethyl)phenyl]-1H-1,2,4-triazole-1-yl]methyl]-2-(trifluoromethyl)pyridine 4-[[5-(Methylthio)-3-[4-(trifluoromethyl)phenyl]-1H-1,2,4-triazole-1-yl]methyl]-2-(trifluoromethyl)pyridine (i.e. the product obtained in Step D, 1.22 g, 2.92 mmol) was dissolved in 30 mL of acetone and 7 mL of de-ionized water while stirring under a nitrogen atmosphere. OXONE® (potassium peroxymonopersulfate, 2.7 g, 4.37 mmol) was added at ambient temperature and stirred for 16 h. Additional OXONE® (2.0 g) was added and the reaction mixture was stirred for 3 h. The reaction mixture was concentrated under reduced pressure, then diluted with de-ionized water and ethyl acetate. The aqueous layer was separated and extracted with ethyl acetate (2×). The combined organic layers were washed with brine, dried over magnesium sulfate, filtered, and concentrated to give 1.47 g of a solid. The solid was purified by silica gel column chromatography using a gradient of 20 to 40% ethyl acetate in hexanes to provide 0.85 g of the title compound as a solid. The solid was filtered from hexanes and diethyl ether to provide 564 mg of the title compound.

$^1$H NMR δ 8.77 (d, 1H), 8.21 (d, 2H), 7.70-7.77 (s & d, 3H), 7.52 (d, 1H), 5.83 (s, 2H), 3.52 (s, 3H).

Step F: Preparation of 4-[[5-ethoxy-3-[4-(trifluoromethyl)phenyl]-1H-1,2,4-triazole-1-yl]methyl]-2-(trifluoromethyl)pyridine Sodium hydride (60% in mineral oil, 50 mg, 0.67 mmol) was dissolved in 1.5 mL of ethanol under a nitrogen atmosphere. The mixture was stirred for about 15 min. at ambient temperature after which 4-[[5-(methyl sulfonyl)-3-[4-(trifluoromethyl)phenyl]-1H-1,2,4-triazole-1-yl]methyl]-2-(trifluoromethyl)pyridine (i.e. the product obtained in the Step E 0.20 g, 0.44 mmol) was added as a solution in 1.5 mL of N,N-dimethylformamide. The resulting mixture was heated at 65° C. for 2 h. The cooled reaction mixture was diluted with de-ionized water. The precipitated solid was filtered and rinsed well with de-ionized water followed by hexanes. The solid was air-dried to yield 57 mg of the title compound.

$^1$H NMR δ 8.72 (d, 1H), 8.13 (d, 2H), 7.69 (d, 2H), 7.60 (s, 1H), 7.38 (d, 1H), 5.25 (s, 2H), 4.60 (q, 2H), 1.46 (t, 3H).

By the procedures described herein together with methods known in the art, the following compounds of Tables 1 to 278 can be prepared. Of note are Tables 1 through 75, 109 through 226, and 255 through 278. The following abbreviations are used in the Tables which follow: n means normal, i means iso, Me means methyl, Et means ethyl, Pr means propyl, Bu means butyl, i-Pr means isopropyl, n-Bu means butyl, Ph means phenyl, OMe means methoxy, OEt means ethoxy, SMe means methylthio, —CN means cyano, Py means pyridinyl, —NO$_2$ means nitro, CF$_3$ means trifluoromethyl, Ph means phenyl and S(O)$_2$Me means methylsulfonyl. Each value for J in the following table refers back to the individual values for J listed below. Of note for values of J is where J is selected from J-2a, J-2b. J-2c. J-10a, J-17a, J-17b, J-18a, J-20a, J-22a. J-29a and J-33a.

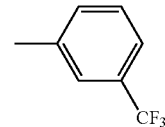

J-1a

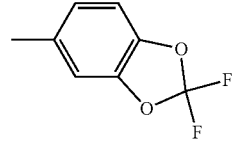

J-1b

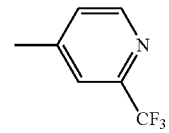

J-2a

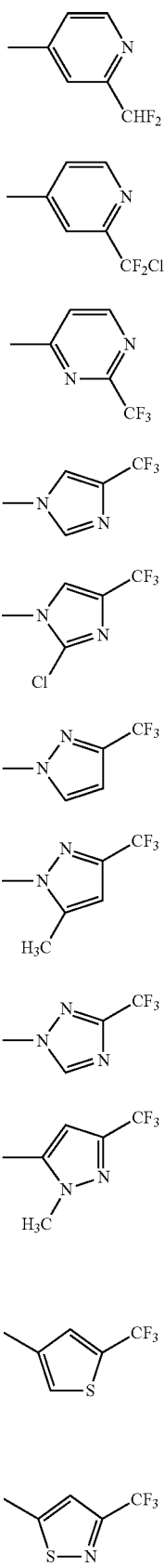

J-2b
J-2c
J-10a
J-17a
J-17b
J-18a
J-18b
J-20a
J-22a
J-29a
J-33a

TABLE 1

$J^1$ = J-2a, $Q^1$ = O, $R^1$ = CH$_3$

| A | A | A |
|---|---|---|
| 4-F—Ph | 2-F—Ph | 2-CF$_3$-4-Pyridyl |
| 4-CF$_3$—Ph | 2-CF$_3$—Ph | 2-Cl-4-Pyridyl |
| 4-Cl—Ph | 2-Cl—Ph | 6-CF$_3$-2-Pyridyl |
| 4-Br—Ph | 2-Br—Ph | 5-CF$_3$-3-Pyridyl |
| 4-SF$_5$—Ph | 2,4-di-F—Ph | 2-CF$_3$-5-Pyridyl |
| 4-OCF$_3$—Ph | 3,4-di-F—Ph | 5-CF$_3$-2-Pyrazinyl |
| 4-SMe—Ph | 2,5-di-F—Ph | 6-CF$_3$-3-Pyridazinyl |
| 4-OMe—Ph | 2,4,6-tri-Ph | 5-F-2-Pyridyl |
| 4-CN—Ph | 2-Cl-4-F—Ph | 2-F-4-Pyridyl |
| 4-Me—Ph | 3-Cl-4-F—Ph | 6-F-2-Pyridyl |
| 4-Ph | 4-F-3-CF$_3$—Ph | 5-F-3-Pyridyl |
| 3-F—Ph | 2-F-4-CF$_3$—Ph | 2-F-5-Pyridyl |
| 3-CF$_3$—Ph | 3-F-4-CF$_3$—Ph | 5-Cl-2-Pyrimidyl |
| 3-Cl—Ph | 3-Cl-4-CF$_3$—Ph | 5-CF$_3$-2-Pyrimidyl |
| 3-Br—Ph | 2-Cl-4-CF$_3$—Ph | 2-CF$_3$-4-Pyrimidyl |
| 3-SF$_5$—Ph | 4-Cl-3-CF$_3$—Ph | 4-CF$_3$-2-Pyrimidyl |
| 3-OCF$_3$—Ph | 2-Pyridyl | 5-Cl-2-Thienyl |
| 2-SMe—Ph | 3-Pyridyl | 5-CF$_3$-2-Thienyl |
| 3-OMe—Ph | 4-Pyridyl | 4-CF$_3$-2-Thiazolyl |
| 3-CN—Ph | 5-CF$_3$-2-Pyridyl | 5-CF$_3$-1,2,5-Thiadiazol-2-yl |
| 3-Me—Ph | 5-Cl-2-Pyridyl | |

The present disclosure also includes Tables 2 through 160. Each Table is constructed in the same manner as Table 1 above, except that the row heading in Table 1 (i.e. "$J^1$=J-2a, $Q^1$=O, $R^1$=CH$_3$") is replaced with the respective row heading shown below. For example, in Table 2 the row heading is "$J^1$ is J-2a, $Q^1$ is O and $R^1$ is Et" and A is as defined in Table 1.

TABLE 161

| Table | Row heading |
|---|---|
| 2 | $J^1$ = J-2a, $Q^1$ = O, $R^1$ = Et |
| 3 | $J^1$ = J-2a, $Q^1$ = O, $R^1$ = n-Pr |
| 4 | $J^1$ = J-2a, $Q^1$ = O, $R^1$ = i-Pr |
| 5 | $J^1$ = J-2a, $Q^1$ = O, $R^1$ = CH$_2$CF$_3$ |
| 6 | $J^1$ = J-2a, $Q^1$ = CH$_2$, $R^1$ = Me |
| 7 | $J^1$ = J-2a, $Q^1$ = CH$_2$, $R^1$ = Et |
| 8 | $J^1$ = J-2a, $Q^1$ = CH$_2$, $R^1$ = n-Pr |
| 9 | $J^1$ = J-2a, $Q^1$ = CH$_2$, $R^1$ = i-Pr |
| 10 | $J^1$ = J-2a, $Q^1$ = CH$_2$, $R^1$ = CH$_2$CF$_3$ |
| 11 | $J^1$ = J-2a, $Q^1$ = C(=O), $R^1$ = Me |
| 12 | $J^1$ = J-2a, $Q^1$ = C(=O), $R^1$ = Et |
| 13 | $J^1$ = J-2a, $Q^1$ = C(=O), $R^1$ = n-Pr |
| 14 | $J^1$ = J-2a, $Q^1$ = CH(OH), $R^1$ = Me |
| 15 | $J^1$ = J-2a, $Q^1$ = CH(OH), $R^1$ = Et |
| 16 | $J^1$ = J-2a, $Q^1$ = CH(OH), $R^1$ = n-Pr |
| 17 | $J^1$ = J-2a, $Q^1$ = S, $R^1$ = Me |
| 18 | $J^1$ = J-2a, $Q^1$ = S, $R^1$ = Et |
| 19 | $J^1$ = J-2a, $Q^1$ = S, $R^1$ = n-Pr |
| 20 | $J^1$ = J-2a, $Q^1$ = NH, $R^1$ = Me |
| 21 | $J^1$ = J-2a, $Q^1$ = NH, $R^1$ = Et |
| 22 | $J^1$ = J-2a, $Q^1$ = NH, $R^1$ = n-Pr |
| 23 | $J^1$ = J-2a, $Q^1$ = CHF, $R^1$ = Me |
| 24 | $J^1$ = J-2a, $Q^1$ = CHF, $R^1$ = Et |
| 25 | $J^1$ = J-2a, $Q^1$ = CHF, $R^1$ = n-Pr |
| 26 | $J^1$ = J-2b, $Q^1$ = O, $R^1$ = Me |
| 27 | $J^1$ = J-2b, $Q^1$ = O, $R^1$ = Et |
| 28 | $J^1$ = J-2b, $Q^1$ = O, $R^1$ = n-Pr |
| 29 | $J^1$ = J-2b, $Q^1$ = O, $R^1$ = i-Pr |
| 30 | $J^1$ = J-2b, $Q^1$ = O, $R^1$ = CH$_2$CF$_3$ |
| 31 | $J^1$ = J-2b, $Q^1$ = CH$_2$, $R^1$ = Me |
| 32 | $J^1$ = J-2b, $Q^1$ = CH$_2$, $R^1$ = Et |
| 33 | $J^1$ = J-2b, $Q^1$ = CH$_2$, $R^1$ = n-Pr |
| 34 | $J^1$ = J-2b, $Q^1$ = CH$_2$, $R^1$ = i-Pr |
| 35 | $J^1$ = J-2b, $Q^1$ = CH$_2$, $R^1$ = CH$_2$CF$_3$ |

TABLE 161-continued

| Table | Row heading |
|---|---|
| 36 | $J^1$ = J-2b, $Q^1$ = C(=O), $R^1$ = Me |
| 37 | $J^1$ = J-2b, $Q^1$ = C(=O), $R^1$ = Et |
| 38 | $J^1$ = J-2b, $Q^1$ = C(=O), $R^1$ = n-Pr |
| 39 | $J^1$ = J-2b, $Q^1$ = CH(OH), $R^1$ = Me |
| 40 | $J^1$ = J-2b, $Q^1$ = CH(OH), $R^1$ = Et |
| 41 | $J^1$ = J-2b, $Q^1$ = CH(OH), $R^1$ = n-Pr |
| 42 | $J^1$ = J-2b, $Q^1$ = S, $R^1$ = Me |
| 43 | $J^1$ = J-2b, $Q^1$ = S, $R^1$ = Et |
| 44 | $J^1$ = J-2b, $Q^1$ = S, $R^1$ = n-Pr |
| 45 | $J^1$ = J-2b, $Q^1$ = NH, $R^1$ = Me |
| 46 | $J^1$ = J-2b, $Q^1$ = NH, $R^1$ = Et |
| 47 | $J^1$ = J-2b, $Q^1$ = NH, $R^1$ = n-Pr |
| 48 | $J^1$ = J-2b, $Q^1$ = CHF, $R^1$ = Me |
| 49 | $J^1$ = J-2b, $Q^1$ = CHF, $R^1$ = Et |
| 50 | $J^1$ = J-2b, $Q^1$ = CHF, $R^1$ = n-Pr |
| 51 | $J^1$ = J-2c, $Q^1$ = O, $R^1$ = Me |
| 52 | $J^1$ = J-2c, $Q^1$ = O, $R^1$ = Et |
| 53 | $J^1$ = J-2c, $Q^1$ = O, $R^1$ = n-Pr |
| 54 | $J^1$ = J-2c, $Q^1$ = O, $R^1$ = i-Pr |
| 55 | $J^1$ = J-2c, $Q^1$ = O, $R^1$ = $CH_2CF_3$ |
| 56 | $J^1$ = J-2c, $Q^1$ = $CH_2$, $R^1$ = Me |
| 57 | $J^1$ = J-2c, $Q^1$ = $CH_2$, $R^1$ = Et |
| 58 | $J^1$ = J-2c, $Q^1$ = $CH_2$, $R^1$ = n-Pr |
| 59 | $J^1$ = J-2c, $Q^1$ = $CH_2$, $R^1$ = i-Pr |
| 60 | $J^1$ = J-2c, $Q^1$ = $CH_2$, $R^1$ = $CH_2CF_3$ |
| 61 | $J^1$ = J-2c, $Q^1$ = C(=O), $R^1$ = Me |
| 62 | $J^1$ = J-2c, $Q^1$ = C(=O), $R^1$ = Et |
| 63 | $J^1$ = J-2c, $Q^1$ = C(=O), $R^1$ = n-Pr |
| 64 | $J^1$ = J-2c, $Q^1$ = CH(OH), $R^1$ = Me |
| 65 | $J^1$ = J-2c, $Q^1$ = CH(OH), $R^1$ = Et |
| 66 | $J^1$ = J-2c, $Q^1$ = CH(OH), $R^1$ = n-Pr |
| 67 | $J^1$ = J-2c, $Q^1$ = S, $R^1$ = Me |
| 68 | $J^1$ = J-2c, $Q^1$ = S, $R^1$ = Et |
| 69 | $J^1$ = J-2c, $Q^1$ = S, $R^1$ = n-Pr |
| 70 | $J^1$ = J-2c, $Q^1$ = NH, $R^1$ = Me |
| 71 | $J^1$ = J-2c, $Q^1$ = NH, $R^1$ = Et |
| 72 | $J^1$ = J-2c, $Q^1$ = NH, $R^1$ = n-Pr |
| 73 | $J^1$ = J-2c, $Q^1$ = CHF, $R^1$ = Me |
| 74 | $J^1$ = J-2c, $Q^1$ = CHF, $R^1$ = Et |
| 75 | $J^1$ = J-2c, $Q^1$ = CHF, $R^1$ = n-Pr |
| 76 | $J^1$ = J-1a, $Q^1$ = O, $R^1$ = Me |
| 77 | $J^1$ = J-1a, $Q^1$ = O, $R^1$ = Et |
| 78 | $J^1$ = J-1a, $Q^1$ = O, $R^1$ = n-Pr |
| 79 | $J^1$ = J-1a, $Q^1$ = O, $R^1$ = i-Pr |
| 80 | $J^1$ = J-1a, $Q^1$ = O, $R^1$ = $CH_2CF_3$ |
| 81 | $J^1$ = J-1a, $Q^1$ = $CH_2$, $R^1$ = Me |
| 82 | $J^1$ = J-1a, $Q^1$ = $CH_2$, $R^1$ = Et |
| 83 | $J^1$ = J-1a, $Q^1$ = $CH_2$, $R^1$ = n-Pr |
| 84 | $J^1$ = J-1a, $Q^1$ = $CH_2$, $R^1$ = i-Pr |
| 85 | $J^1$ = J-1a, $Q^1$ = $CH_2$, $R^1$ = $CH_2CF_3$ |
| 86 | $J^1$ = J-1a, $Q^1$ = C(=O), $R^1$ = Me |
| 87 | $J^1$ = J-1a, $Q^1$ = C(=O), $R^1$ = Et |
| 88 | $J^1$ = J-1a, $Q^1$ = C(=O), $R^1$ = n-Pr |
| 89 | $J^1$ = J-1a, $Q^1$ = CH(OH), $R^1$ = Me |
| 90 | $J^1$ = J-1a, $Q^1$ = CH(OH), $R^1$ = Et |
| 91 | $J^1$ = J-1a, $Q^1$ = CH(OH), $R^1$ = n-Pr |
| 92 | $J^1$ = J-1a, $Q^1$ = S, $R^1$ = Me |
| 93 | $J^1$ = J-1a, $Q^1$ = S, $R^1$ = Et |
| 94 | $J^1$ = J-1a, $Q^1$ = S, $R^1$ = n-Pr |
| 95 | $J^1$ = J-1a, $Q^1$ = NH, $R^1$ = Me |
| 96 | $J^1$ = J-1a, $Q^1$ = NH, $R^1$ = Et |
| 97 | $J^1$ = J-1a, $Q^1$ = NH, $R^1$ = n-Pr |
| 98 | $J^1$ = J-1a, $Q^1$ = CHF, $R^1$ = Me |
| 99 | $J^1$ = J-1a, $Q^1$ = CHF, $R^1$ = Et |
| 100 | $J^1$ = J-1a, $Q^1$ = CHF, $R^1$ = n-Pr |
| 101 | $J^1$ = J-1b, $Q^1$ = O, $R^1$ = Me |
| 102 | $J^1$ = J-1b, $Q^1$ = O, $R^1$ = Et |
| 103 | $J^1$ = J-1b, $Q^1$ = O, $R^1$ = n-Pr |
| 104 | $J^1$ = J-1b, $Q^1$ = O, $R^1$ = $CH_2CF_3$ |
| 105 | $J^1$ = J-1b, $Q^1$ = $CH_2$, $R^1$ = Me |
| 106 | $J^1$ = J-1b, $Q^1$ = $CH_2$, $R^1$ = Et |
| 107 | $J^1$ = J-1b, $Q^1$ = $CH_2$, $R^1$ = n-Pr |
| 108 | $J^1$ = J-1b, $Q^1$ = $CH_2$, $R^1$ = $CH_2CF_3$ |
| 109 | $J^1$ = J-10a, $Q^1$ = O, $R^1$ = Me |
| 110 | $J^1$ = J-10a, $Q^1$ = O, $R^1$ = Et |
| 111 | $J^1$ = J-10a, $Q^1$ = O, $R^1$ = n-Pr |
| 112 | $J^1$ = J-10a, $Q^1$ = O, $R^1$ = $CH_2CF_3$ |
| 113 | $J^1$ = J-10a, $Q^1$ = $CH_2$, $R^1$ = Me |
| 114 | $J^1$ = J-10a, $Q^1$ = $CH_2$, $R^1$ = Et |
| 115 | $J^1$ = J-10a, $Q^1$ = $CH_2$, $R^1$ = n-Pr |
| 116 | $J^1$ = J-10a, $Q^1$ = $CH_2$, $R^1$ = $CH_2CF_3$ |
| 117 | $J^1$ = J-29a, $Q^1$ = O, $R^1$ = Me |
| 118 | $J^1$ = J-29a, $Q^1$ = O, $R^1$ = Et |
| 119 | $J^1$ = J-29a, $Q^1$ = O, $R^1$ = n-Pr |
| 120 | $J^1$ = J-29a, $Q^1$ = O, $R^1$ = $CH_2CF_3$ |
| 121 | $J^1$ = J-29a, $Q^1$ = $CH_2$, $R^1$ = Me |
| 122 | $J^1$ = J-29a, $Q^1$ = $CH_2$, $R^1$ = Et |
| 123 | $J^1$ = J-29a, $Q^1$ = $CH_2$, $R^1$ = n-Pr |
| 124 | $J^1$ = J-29a, $Q^1$ = $CH_2$, $R^1$ = $CH_2CF_3$ |
| 125 | $J^1$ = J-33a, $Q^1$ = O, $R^1$ = Me |
| 126 | $J^1$ = J-33a, $Q^1$ = O, $R^1$ = Et |
| 127 | $J^1$ = J-33a, $Q^1$ = O, $R^1$ = n-Pr |
| 128 | $J^1$ = J-33a, $Q^1$ = O, $R^1$ = $CH_2CF_3$ |
| 129 | $J^1$ = J-33a, $Q^1$ = $CH_2$, $R^1$ = Me |
| 130 | $J^1$ = J-33a, $Q^1$ = $CH_2$, $R^1$ = Et |
| 131 | $J^1$ = J-33a, $Q^1$ = $CH_2$, $R^1$ = n-Pr |
| 132 | $J^1$ = J-33a, $Q^1$ = $CH_2$, $R^1$ = $CH_2CF_3$ |
| 133 | $J^1$ = J-22a, $Q^1$ = O, $R^1$ = Me |
| 134 | $J^1$ = J-22a, $Q^1$ = O, $R^1$ = Et |
| 135 | $J^1$ = J-22a, $Q^1$ = O, $R^1$ = n-Pr |
| 136 | $J^1$ = J-22a, $Q^1$ = O, $R^1$ = $CH_2CF_3$ |
| 137 | $J^1$ = J-22a, $Q^1$ = $CH_2$, $R^1$ = Me |
| 138 | $J^1$ = J-22a, $Q^1$ = $CH_2$, $R^1$ = Et |
| 139 | $J^1$ = J-22a, $Q^1$ = $CH_2$, $R^1$ = n-Pr |
| 140 | $J^1$ = J-22a, $Q^1$ = $CH_2$, $R^1$ = $CH_2CF_3$ |
| 141 | $J^1$ = 18a, $Q^1$ = CH2, $R^1$ = Me |
| 142 | $J^1$ = 18a, $Q^1$ = $CH_2$, $R^1$ = Et |
| 143 | $J^1$ = 18a, $Q^1$ = $CH_2$, $R^1$ = n-Pr |
| 144 | $J^1$ = 18a, $Q^1$ = $CH_2$, $R^1$ = $CH_2CF_3$ |
| 145 | $J^1$ = J-20a, $Q^1$ = $CH_2$, $R^1$ = Me |
| 146 | $J^1$ = J-20a, $Q^1$ = $CH_2$, $R^1$ = Et |
| 147 | $J^1$ = J-20a, $Q^1$ = $CH_2$, $R^1$ = n-Pr |
| 148 | $J^1$ = J-20a, $Q^1$ = $CH_2$, $R^1$ = $CH_2CF_3$ |
| 149 | $J^1$ = J-17a, $Q^1$ = $CH_2$, $R^1$ = Me |
| 150 | $J^1$ = J-17a, $Q^1$ = $CH_2$, $R^1$ = Et |
| 151 | $J^1$ = J-17a, $Q^1$ = $CH_2$, $R^1$ = n-Pr |
| 152 | $J^1$ = J-17a, $Q^1$ = $CH_2$, $R^1$ = $CH_2CF_3$ |
| 153 | $J^1$ = J-17b, $Q^1$ = $CH_2$, $R^1$ = Me |
| 154 | $J^1$ = J-17b, $Q^1$ = $CH_2$, $R^1$ = Et |
| 155 | $J^1$ = J-17b, $Q^1$ = $CH_2$, $R^1$ = n-Pr |
| 156 | $J^1$ = J-17b, $Q^1$ = $CH_2$, $R^1$ = $CH_2CF_3$ |
| 157 | $J^1$ = J-18b, $Q^1$ = $CH_2$, $R^1$ = Me |
| 158 | $J^1$ = J-18b, $Q^1$ = $CH_2$, $R^1$ = Et |
| 159 | $J^1$ = J-18b, $Q^1$ = $CH_2$, $R^1$ = n-Pr |
| 160 | $J^1$ = J-18b, $Q^1$ = $CH_2$, $R^1$ = $CH_2CF_3$ |

Table 161 is constructed the same way as Table 1 except the structure and row heading in Table 1 are replaced with the structure and row heading below. The value for variable A is as defined in Table 1.

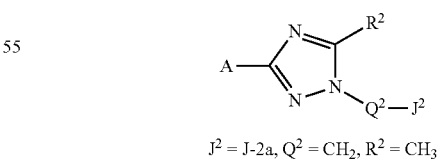

$J^2$ = J-2a, $Q^2$ = $CH_2$, $R^2$ = $CH_3$

The present disclosure also includes Table 162-278. Each Table is constructed in the same way as Table 161 above, except the row heading in Table 161 (i.e. "$J^2$=J-2a, $Q^2$=$CH_2$, $R^2$=$CH_3$") is replaced with respective row heading show below. For example, the row heading in Table 162 is "$J^2$=J-2a, $Q^2$=$CH_2$, $R^2$=Et" and A is as defined in Table 1.

| Table | Row heading |
|---|---|
| 162 | $J^2$ = J-2a, $Q^2$ = $CH_2$, $R^2$ = Et |
| 163 | $J^2$ = J-2a, $Q^2$ = $CH_2$, $R^2$ = n-Pr |
| 164 | $J^2$ = J-2a, $Q^2$ = $CH_2$, $R^2$ = i-Pr |
| 165 | $J^2$ = J-2a, $Q^2$ = $CH_2$, $R^2$ = $CH_2OCH_3$ |
| 166 | $J^2$ = J-2a, $Q^2$ = $CH_2$, $R^2$ = OMe |
| 167 | $J^2$ = J-2a, $Q^2$ = $CH_2$, $R^2$ = OEt |
| 168 | $J^2$ = J-2a, $Q^2$ = $CH_2$, $R^2$ = $OCH_2F$ |
| 169 | $J^2$ = J-2a, $Q^2$ = $CH_2$, $R^2$ = $OCH_2CF_3$ |
| 170 | $J^2$ = J-2a, $Q^2$ = $CH_2$, $R^2$ = Cl |
| 171 | $J^2$ = J-2a, $Q^2$ = $CH_2$, $R^2$ = Br |
| 172 | $J^2$ = J-2a, $Q^2$ = C(=O), $R^2$ = Me |
| 173 | $J^2$ = J-2a, $Q^2$ = C(=O), $R^2$ = Et |
| 174 | $J^2$ = J-2a, $Q^2$ = C(=O), $R^2$ = n-Pr |
| 175 | $J^2$ = J-2a, $Q^2$ = C(=O), $R^2$ = i-Pr |
| 176 | $J^2$ = J-2a, $Q^2$ = C(=O), $R^2$ = $CH_2OCH_3$ |
| 177 | $J^2$ = J-2a, $Q^2$ = C(=O), $R^2$ = OMe |
| 178 | $J^2$ = J-2a, $Q^2$ = C(=O), $R^2$ = OEt |
| 179 | $J^2$ = J-2a, $Q^2$ = C(=O), $R^2$ = $OCH_2F$ |
| 180 | $J^2$ = J-2a, $Q^2$ = C(=O), $R^2$ = $OCH_2CF_3$ |
| 181 | $J^2$ = J-2a, $Q^2$ = C(=O), $R^2$ = Cl |
| 182 | $J^2$ = J-2a, $Q^2$ = C(=O), $R^2$ = Br |
| 183 | $J^2$ = J-2b, $Q^2$ = $CH_2$, $R^2$ = Me |
| 184 | $J^2$ = J-2b, $Q^2$ = $CH_2$, $R^2$ = Et |
| 185 | $J^2$ = J-2b, $Q^2$ = $CH_2$, $R^2$ = n-Pr |
| 186 | $J^2$ = J-2b, $Q^2$ = $CH_2$, $R^2$ = i-Pr |
| 187 | $J^2$ = J-2b, $Q^2$ = $CH_2$, $R^2$ = $CH_2OCH_3$ |
| 188 | $J^2$ = J-2b, $Q^2$ = $CH_2$, $R^2$ = OMe |
| 189 | $J^2$ = J-2b, $Q^2$ = $CH_2$, $R^2$ = OEt |
| 190 | $J^2$ = J-2b, $Q^2$ = $CH_2$, $R^2$ = $OCH_2F$ |
| 191 | $J^2$ = J-2b, $Q^2$ = $CH_2$, $R^2$ = $OCH_2CF_3$ |
| 192 | $J^2$ = J-2b, $Q^2$ = $CH_2$, $R^2$ = Cl |
| 193 | $J^2$ = J-2b, $Q^2$ = $CH_2$, $R^2$ = Br |
| 194 | $J^2$ = J-2b, $Q^2$ = C(=O), $R^2$ = Me |
| 195 | $J^2$ = J-2b, $Q^2$ = C(=O), $R^2$ = Et |
| 196 | $J^2$ = J-2b, $Q^2$ = C(=O), $R^2$ = n-Pr |
| 197 | $J^2$ = J-2b, $Q^2$ = C(=O), $R^2$ = i-Pr |
| 198 | $J^2$ = J-2b, $Q^2$ = C(=O), $R^2$ = $CH_2OCH_3$ |
| 199 | $J^2$ = J-2b, $Q^2$ = C(=O), $R^2$ = OMe |
| 200 | $J^2$ = J-2b, $Q^2$ = C(=O), $R^2$ = OEt |
| 201 | $J^2$ = J-2b, $Q^2$ = C(=O), $R^2$ = $OCH_2F$ |
| 202 | $J^2$ = J-2b, $Q^2$ = C(=O), $R^2$ = $OCH_2CF_3$ |
| 203 | $J^2$ = J-2b, $Q^2$ = C(=O), $R^2$ = Cl |
| 204 | $J^2$ = J-2b, $Q^2$ = C(=O), $R^2$ = Br |
| 205 | $J^2$ = J-2c, $Q^2$ = $CH_2$, $R^2$ = Me |
| 206 | $J^2$ = J-2c, $Q^2$ = $CH_2$, $R^2$ = Et |
| 207 | $J^2$ = J-2c, $Q^2$ = $CH_2$, $R^2$ = n-Pr |
| 208 | $J^2$ = J-2c, $Q^2$ = $CH_2$, $R^2$ = i-Pr |
| 209 | $J^2$ = J-2c, $Q^2$ = $CH_2$, $R^2$ = $CH_2OCH_3$ |
| 210 | $J^2$ = J-2c, $Q^2$ = $CH_2$, $R^2$ = OMe |
| 211 | $J^2$ = J-2c, $Q^2$ = $CH_2$, $R^2$ = OEt |
| 212 | $J^2$ = J-2c, $Q^2$ = $CH_2$, $R^2$ = $OCH_2F$ |
| 213 | $J^2$ = J-2c, $Q^2$ = $CH_2$, $R^2$ = $OCH_2CF_3$ |
| 214 | $J^2$ = J-2c, $Q^2$ = $CH_2$, $R^2$ = Cl |
| 215 | $J^2$ = J-2c, $Q^2$ = $CH_2$, $R^2$ = Br |
| 216 | $J^2$ = J-2c, $Q^2$ = C(=O), $R^2$ = Me |
| 217 | $J^2$ = J-2c, $Q^2$ = C(=O), $R^2$ = Et |
| 218 | $J^2$ = J-2c, $Q^2$ = C(=O), $R^2$ = n-Pr |
| 219 | $J^2$ = J-2c, $Q^2$ = C(=O), $R^2$ = i-Pr |
| 220 | $J^2$ = J-2c, $Q^2$ = C(=O), $R^2$ = $CH_2OCH_3$ |
| 221 | $J^2$ = J-2c, $Q^2$ = C(=O), $R^2$ = OMe |
| 222 | $J^2$ = J-2c, $Q^2$ = C(=O), $R^2$ = OEt |
| 223 | $J^2$ = J-2c, $Q^2$ = C(=O), $R^2$ = $OCH_2F$ |
| 224 | $J^2$ = J-2c, $Q^2$ = C(=O), $R^2$ = $OCH_2CF_3$ |
| 225 | $J^2$ = J-2c, $Q^2$ = C(=O), $R^2$ = Cl |
| 226 | $J^2$ = J-2c, $Q^2$ = C(=O), $R^2$ = Br |
| 227 | $J^2$ = J-1a, $Q^2$ = $CH_2$, $R^2$ = Me |
| 228 | $J^2$ = J-1a, $Q^2$ = $CH_2$, $R^2$ = Et |
| 229 | $J^2$ = J-1a, $Q^2$ = $CH_2$, $R^2$ = n-Pr |
| 230 | $J^2$ = J-1a, $Q^2$ = $CH_2$, $R^2$ = i-Pr |
| 231 | $J^2$ = J-1a, $Q^2$ = $CH_2$, $R^2$ = $CH_2OCH_3$ |
| 232 | $J^2$ = J-1a, $Q^2$ = $CH_2$, $R^2$ = OMe |
| 233 | $J^2$ = J-1a, $Q^2$ = $CH_2$, $R^2$ = OEt |
| 234 | $J^2$ = J-1a, $Q^2$ = $CH_2$, $R^2$ = $OCH_2F$ |
| 235 | $J^2$ = J-1a, $Q^2$ = $CH_2$, $R^2$ = $OCH_2CF_3$ |
| 236 | $J^2$ = J-1a, $Q^2$ = $CH_2$, $R^2$ = Cl |
| 237 | $J^2$ = J-1a, $Q^2$ = $CH_2$, $R^2$ = Br |
| 238 | $J^2$ = J-1a, $Q^2$ = C(=O), $R^2$ = Me |
| 239 | $J^2$ = J-1a, $Q^2$ = C(=O), $R^2$ = Et |
| 240 | $J^2$ = J-1a, $Q^2$ = C(=O), $R^2$ = n-Pr |
| 241 | $J^2$ = J-1a, $Q^2$ = C(=O), $R^2$ = i-Pr |
| 242 | $J^2$ = J-1a, $Q^2$ = C(=O), $R^2$ = $CH_2OCH_3$ |
| 243 | $J^2$ = J-1a, $Q^2$ = C(=O), $R^2$ = OMe |
| 244 | $J^2$ = J-1a, $Q^2$ = C(=O), $R^2$ = OEt |
| 245 | $J^2$ = J-1a, $Q^2$ = C(=O), $R^2$ = $OCH_2F$ |
| 246 | $J^2$ = J-1a, $Q^2$ = C(=O), $R^2$ = $OCH_2CF_3$ |
| 247 | $J^2$ = J-1a, $Q^2$ = C(=O), $R^2$ = Cl |
| 248 | $J^2$ = J-1a, $Q^2$ = C(=O), $R^2$ = Br |
| 249 | $J^2$ = J-1b, $Q^2$ = $CH_2$, $R^2$ = Me |
| 250 | $J^2$ = J-1b, $Q^2$ = $CH_2$, $R^2$ = Et |
| 251 | $J^2$ = J-1b, $Q^2$ = $CH_2$, $R^2$ = n-Pr |
| 252 | $J^2$ = J-1b, $Q^2$ = $CH_2$, $R^2$ = $CH_2OCH_3$ |
| 253 | $J^2$ = J-1b, $Q^2$ = $CH_2$, $R^2$ = OMe |
| 254 | $J^2$ = J-1b, $Q^2$ = $CH_2$, $R^2$ = OEt |
| 255 | $J^2$ = J-10a, $Q^2$ = $CH_2$, $R^2$ = Me |
| 256 | $J^2$ = J-10a, $Q^2$ = $CH_2$, $R^2$ = Et |
| 257 | $J^2$ = J-10a, $Q^2$ = $CH_2$, $R^2$ = n-Pr |
| 258 | $J^2$ = J-10a, $Q^2$ = $CH_2$, $R^2$ = $CH_2OCH_3$ |
| 259 | $J^2$ = J-10a, $Q^2$ = $CH_2$, $R^2$ = OMe |
| 260 | $J^2$ = J-10a, $Q^2$ = $CH_2$, $R^2$ = OEt |
| 261 | $J^2$ = J-29a, $Q^2$ = $CH_2$, $R^2$ = Me |
| 262 | $J^2$ = J-29a, $Q^2$ = $CH_2$, $R^2$ = Et |
| 263 | $J^2$ = J-29a, $Q^2$ = $CH_2$, $R^2$ = n-Pr |
| 264 | $J^2$ = J-29a, $Q^2$ = $CH_2$, $R^2$ = $CH_2OCH_3$ |
| 265 | $J^2$ = J-29a, $Q^2$ = $CH_2$, $R^2$ = OMe |
| 266 | $J^2$ = J-29a, $Q^2$ = $CH_2$, $R^2$ = OEt |
| 267 | $J^2$ = J-33a, $Q^2$ = $CH_2$, $R^2$ = Me |
| 268 | $J^2$ = J-33a, $Q^2$ = $CH_2$, $R^2$ = Et |
| 269 | $J^2$ = J-33a, $Q^2$ = $CH_2$, $R^2$ = n-Pr |
| 270 | $J^2$ = J-33a, $Q^2$ = $CH_2$, $R^2$ = $CH_2OCH_3$ |
| 271 | $J^2$ = J-33a, $Q^2$ = $CH_2$, $R^2$ = OMe |
| 272 | $J^2$ = J-33a, $Q^2$ = $CH_2$, $R^2$ = OEt |
| 273 | $J^2$ = J-22a, $Q^2$ = $CH_2$, $R^2$ = Me |
| 274 | $J^2$ = J-22a, $Q^2$ = $CH_2$, $R^2$ = Et |
| 275 | $J^2$ = J-22a, $Q^2$ = $CH_2$, $R^2$ = n-Pr |
| 276 | $J^2$ = J-22a, $Q^2$ = $CH_2$, $R^2$ = $CH_2OCH_3$ |
| 277 | $J^2$ = J-22a, $Q^2$ = $CH_2$, $R^2$ = OMe |
| 278 | $J^2$ = J-22a, $Q^2$ = $CH_2$, $R^2$ = OEt |

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as NN-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following non-limiting Examples are illustrative of the invention. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 1 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except the "Compound 1" is replaced with "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", "Compound 36", "Compound 37", "Compound 38", "Compound 39", "Compound 40" or "Compound 41". Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have (both preemergent and postemergent herbicidal) activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. "tol." means "tolerance", "res." means "resistance", "mod" means "modified" and "herb." means "herbicide". A "-" means the entry is not available.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herb. tol. |
| T12 | Dicamba Tol. |
| T13 | Anti-allergy |
| T14 | Salt tol. |
| T15 | Cold tol. |
| T16 | Imidazolinone herb. tol. |
| T17 | Mod. alpha-amylase |
| T18 | Pollination control |
| T19 | 2,4-D tol. |
| T20 | Increased lysine |
| T21 | Drought tol. |
| T22 | Delayed ripening/senescence |
| T23 | Mod. product quality |
| T24 | High cellulose |
| T25 | Mod. starch/carbohydrate |
| T26 | Insect & disease res. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Mod. product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |

| Crop | Event Name | Event Code | Trait(s) | Gene(s) |
|---|---|---|---|---|
| Canola* | MON88302 | MON-88302-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |

| Crop | Event Name | Event Code | Trait(s) | Gene(s) |
| --- | --- | --- | --- | --- |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | F1117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |

-continued

| Crop | Event Name | Event Code | Trait(s) | Gene(s) |
|---|---|---|---|---|
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-tri ethyl ammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2, 6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1, 5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13*th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide.

Table A1 lists specific combinations of a Component (a) with Component (b) illustrative of the mixtures, compositions and methods of the present invention. Compound 1 in the Component (a) column is identified in Index Table B. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table B) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Aciflurofen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |

TABLE A1-continued

| Component (a) (Compound #) | Component (b) | Typical Weight Ratio | More Typical Weight Ratio | Most Typical Weight Ratio |
|---|---|---|---|---|
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucalbazone | 1:8-135:1 | 1:2-45:1 | 1:1-9:1 |
| 1 | Flucetosulfuron | 1:8-135:1 | 1:2-45:1 | 1:1-9:1 |

TABLE A1-continued

| Component (a) (Compound #) | Component (b) | Typical Weight Ratio | More Typical Weight Ratio | Most Typical Weight Ratio |
|---|---|---|---|---|
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencathazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |

TABLE A1-continued

| Component (a) (Compound #) | Component (b) | Typical Weight Ratio | More Typical Weight Ratio | Most Typical Weight Ratio |
|---|---|---|---|---|
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound # in the Component (a) column is identified in Index Tables A and B. Thus, for example, in Table A2 the entries below the "Component (a)" column heading all recite "Compound 6" (i.e. Compound 6 identified in Index Table B), and the first line below the column headings in Table A2 specifically discloses a mixture of Compound 6 with 2,4-D. Tables A3 through A41 are constructed similarly.

| Table Number | Component (a) Column Entries |
|---|---|
| A2 | 6 |
| A3 | 8 |
| A4 | 9 |
| A5 | 17 |
| A6 | 2 |
| A7 | 3 |
| A8 | 4 |
| A9 | 5 |
| A10 | 7 |
| A11 | 10 |

-continued

| Table Number | Component (a) Column Entries |
|---|---|
| A12 | 11 |
| A13 | 12 |
| A14 | 13 |
| A15 | 14 |
| A16 | 15 |
| A17 | 16 |
| A18 | 18 |
| A19 | 19 |
| A20 | 20 |
| A21 | 21 |
| A22 | 22 |
| A23 | 23 |
| A24 | 24 |
| A25 | 25 |
| A26 | 26 |
| A27 | 27 |
| A28 | 28 |
| A29 | 29 |
| A30 | 30 |
| A31 | 31 |
| A32 | 32 |
| A33 | 33 |
| A34 | 34 |
| A35 | 35 |
| A36 | 36 |
| A37 | 37 |
| A38 | 38 |
| A39 | 39 |
| A40 | 40 |
| A41 | 41 |

The following Tests demonstrate the control efficacy of the compounds of this invention against specific weeds. The weed control afforded by the compounds is not limited, however, to these species. See Index Tables A for compound descriptions. The following abbreviations are used in the Index Tables which follow: $CF_3$ is trifluoromethyl, Pyr is pyridyl, n is normal, Et is ethyl, Pr is propyl, $CF_3$ is trifluoromethyl, Pyr is pyridyl, and Ph is phenyl. The abbreviation "Ex." stands for "Example" and is followed by a number indicating in which example the compound is prepared.

INDEX TABLE A

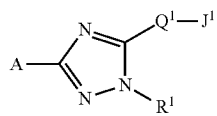

| Cmpd. No. | A | $Q^1$ | $J^1$ | $R^1$ | M.S. |
|---|---|---|---|---|---|
| 5 (Ex. 2) | 4-F—Ph | O | 3-$CF_3$—Ph | $CH_3$ | 337.9$^a$ |
| 13 (Ex. 3) | 4-F—Ph | $CH_2$ | 2-$CF_3$-4-Pyr | $CH_3$ | ** |
| 14 (Ex. 3) | 4-F—Ph | CH(OH) | 2-$CF_3$-4-Pyr | $CH_3$ | ** |
| 15 | 4-F—Ph | CH(OH) | 2-$CF_3$-4-Pyr | Et | * |
| 16 | 4-F—Ph | CH(OH) | 2-$CF_3$-4-Pyr | n-Pr | * |

INDEX TABLE A-continued

| Cmpd. No. | A | $Q^1$ | $J^1$ | $R^1$ | M.S. |
|---|---|---|---|---|---|
| 17 | 4-F—Ph | $CH_2$ | 2-$CF_3$-4-Pyr | n-Pr | 365.6$^c$ |
| 18 | 4-F—Ph | $CH_2$ | 2-$CF_3$-4-Pyr | Et | 351.6$^c$ |
| 19 (Ex. 5) | 4-F—Ph | C=O | 2-$CF_3$-4-Pyr | Et | 365.6$^c$ |
| 20 | 4-F—Ph | C=O | 2-$CF_3$-4-Pyr | n-Pr | * |

$^a$ES$^+$, $^b$ES$^-$, $^c$AP$^+$.
* See Index Table C for $^1$H NMR data.
** See Synthesis Example for $^1$H NMR data.

INDEX TABLE B

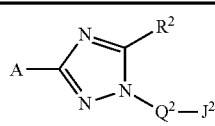

| Cmpd. No. | A | $Q^2$ | $J^2$ | $R^2$ | M.S. |
|---|---|---|---|---|---|
| 1 (Ex. 1) | 4-$CF_3$—Ph | $CH_2$ | 2-$CF_3$-4-Pyr | Et | ** |
| 2 | 4-F—Ph | $CH_2$ | 2-$CF_3$-4-Pyr | Et | 351$^a$ |
| 3 | 4-$CF_3$—Ph | $CH_2$ | 3-$CF_3$—Ph | $CH_3$ | * |
| 4 | 4-$CF_3$—Ph | $CH_2$ | 3-$OCF_3$—Ph | $CH_3$ | * |
| 6 | 4-F—Ph | $CH_2$ | 2-$CF_3$-4-Pyr | n-Pr | 365$^c$ |
| 7 | 4-$CF_3$—Ph | $CH_2$ | 2-$CF_3$-4-Pyr | $CH_3$ | 385$^b$ |
| 8 (Ex. 4) | 4-F—Ph | $CH_2$ | 2-$CF_3$-4-Pyr | OEt | ** |
| 9 | 4-F—Ph | $CH_2$ | 2-$CF_3$-4-Pyr | $OCH_3$ | 353.5$^c$ |
| 10 | 4-F—Ph | $CH_2$ | 2-$CF_3$-4-Pyr | O-n-Pr | 381.5$^c$ |
| 11 | 3-$CF_3$—Ph | $CH_2$ | 2-$CF_3$-4-Pyr | Et | 401.6$^c$ |
| 12 | 4-$CF_3$—Ph | $CH_2$ | 2-$CF_3$-4-Pyr | n-Pr | 415.6$^c$ |
| 21 | 4-F—Ph | $CH_2$ | 2-$CF_3$-4-Pyr | $SCH_3$ | 369.6$^c$ |
| 22 | 4-Cl—Ph | $CH_2$ | 2-$CF_3$-4-Pyr | n-Pr | 381.6$^c$ |
| 23 | 3,4-di-F—Ph | $CH_2$ | 2-$CF_3$-4-Pyr | n-Pr | 383.6$^c$ |
| 24 | Ph | $CH_2$ | 2-$CF_3$-4-Pyr | $OCH_2CF_3$ | * |
| 25 | 4-$CF_3$—Ph | $CH_2$ | 2-$CF_3$-4-Pyr | $OCH_3$ | * |
| 26 | 4-Cl—Ph | $CH_2$ | 2-$CF_3$-4-Pyr | OEt | * |
| 27 | Ph | $CH_2$ | 2-$CF_3$-4-Pyr | OEt | * |
| 28 | 4-Cl—Ph | $CH_2$ | 2-$CF_3$-4-Pyr | $OCH_3$ | * |
| 29 | 4-F—Ph | $CH_2$ | 2-$CF_3$-4-Pyr | S(=O)$_2$CH$_3$ | * |
| 30 | 4-F—Ph | $CH_2$ | 2-$CF_3$-4-Pyr | $OCH_2CF_3$ | * |
| 31 | 4-Cl—Ph | $CH_2$ | 2-$CF_3$-4-Pyr | $OCH_2CF_3$ | * |
| 32 | Ph | $CH_2$ | 2-$CF_3$-4-Pyr | $OCH_3$ | * |
| 33 | Ph | $CH_2$ | 2-$CF_3$-4-Pyr | O-n-Pr | * |
| 34 | 4-$CF_3$—Ph | $CH_2$ | 2-$CF_3$-4-Pyr | $OCH_2CF_3$ | * |
| 35 (Ex. 6) | 4-$CF_3$—Ph | $CH_2$ | 2-$CF_3$-4-Pyr | OEt | * |
| 36 | 4-Br—Ph | $CH_2$ | 2-$CF_3$-4-Pyr | $CH_3$ | * |
| 37 | 4-$OCF_3$—Ph | $CH_2$ | 2-$CF_3$-4-Pyr | $CH_3$ | * |
| 38 | 4-F—Ph | $CH_2$ | 2-$CF_3$-4-Pyr | $CH_3$ | * |
| 39 | 4-Pyr | $CH_2$ | 2-$CF_3$-4-Pyr | Et | * |
| 40 | 4-$OCF_3$—Ph | $CH_2$ | 2-$CF_3$-4-Pyr | $OCH_3$ | * |
| 41 | 4-$CF_3$—Ph | $CH_2$ | 2-$CF_3$-4-Pyr | O-n-Pr | * |

$^a$ES$^+$, $^b$ES$^-$, $^c$AP$^+$.
* See Index Table C for $^1$H NMR data.

INDEX TABLE C

| Cmpd. No. | Data (CDCl$_3$ solution unless indicated otherwise)$^a$ |
|---|---|
| 3 | δ 8.2 (d, 2H), 7.69 (d, 2H), 7.6 (d, 1H), 7.52 (s, 1H), 7.50 (t, 1H), 7.4 (d, 1H), 5.40 (s, 2H), 2.49 (s, 3H). |
| 4 | δ 8.2 (d, 2H), 7.4 (t, 1H), 7.2 (d, 1H), 7.1 (d, 1H), 7.0 (s, 1H), 5.36 (s, 2H), 2.47 (s, 3H). |
| 15 | δ 8.73 (d, 1H), 8.02 (m, 2H), 7.79 (s, 1H), 7.50 (d, 1H), 7.13 (t, 2H), 6.14 (d, 1H), 4.66 (d, 1H), 3.99 (m, 2H), 1.24 (t, 3H). |
| 16 | δ 8.73 (d, 1H), 8.03 (m, 2H), 7.80 (s, 1H), 7.51 (d, 1H), 7.12 (t, 2H), 6.12 (d, 1H), 4.30 (bs, 1H), 3.93 (m, 2H), 1.76 (m, 1H), 1.67 (m, 1H), 0.79 (t, 3H). |

INDEX TABLE C-continued

| Cmpd. No. | Data (CDCl$_3$ solution unless indicated otherwise)$^a$ |
|---|---|
| 20 | δ 9.01 (d, 1H), 8.72 (s, 1H), 8.54 (d, 1H), 8.13 (m, 2H), 7.15 (t, 2H), 4.64 (m, 2H), 2.01 (m, 2H), 1.03 (t, 3H). |
| 24 | δ 8.72 (d, 1H), 8.00 (d, 2H), 7.62 (s, 1H), 7.38-7.46 (m, 4H), 5.27 (s, 2H), 4.93 (q, 2H). |
| 25 | δ 8.72 (d, 1H), 8.14 (d, 2H), 7.68 (d, 2H), 7.59 (s, 1H), 7.37 (d, 1H), 5.24 (s, 2H), 4.21 (s, 3H). |
| 26 | δ 8.71 (d, 1H), 7.95 (d, 2H), 7.39 (d, 2H), 7.37 (d, 1H), 5.22 (s, 2H), 4.58 (q, 2H), 1.46 (t, 3H). |
| 27 | δ 8.71 (d, 1H), 8.0 (d, 2H), 7.61 (s, 1H), 7.36-7.44 (m, 4H), 5.24 (s, 2H), 4.59 (q, 2H), 1.45 (t, 3H). |
| 28 | δ 8.72 (d, 1H), 7.97 (d, 2H), 7.59 (s, 1H), 7.39 (d, 2H), 5.22 (s, 2H), 4.19 (s, 3H). |
| 29 | δ 8.78 (d, 1H), 8.19 (m, 2H), 7.74 (s, 1H), 7.52 (d, 1H), 7.15 (t, 2H), 5.79 (s, 2H), 3.49 (s, 3H). |
| 30 | δ 8.72 (d, 1H), 7.99 (m, 2H), 7.61 (s, 1H), 7.39 (d, 1H), 7.11 (t, 2H), 5.27 (s, 2H), 4.91 (m, 2H). |
| 31 | δ 8.73 (d, 1H), 7.94 (d, 2H), 7.61 (s, 1H), 7.40 (d, 3H), 5.27 (s, 2H), 4.91 (q, 2H). |
| 32 | δ 8.70 (d, 1H), 8.02 (d, 2H), 7.59 (s, 1H), 7.39-7.45 (m, 3H), 7.37 (d, 1H), 5.23 (s, 2H), 4.20 (s, 3H). |
| 33 | δ 8.71 (d, 1H), 8.02 (d, 2H), 7.60 (s, 1H), 7.36-7.45 (m, 4H), 5.24 (s, 2H), 4.49 (t, 2H), 1.82 (m, 2H), 1.00 (t, 3H). |
| 34 | δ 8.74 (d, 1H), 8.12 (d, 2H), 7.68 (d, 2H), 7.61 (s, 1H), 7.40 (d, 1H), 5.29 (s, 2H), 4.94 (q, 2H). |
| 35 | δ 8.72 (d, 1H), 8.13 (d, 2H), 7.69 (d, 2H), 7.60 (s, 1H), 7.38 (d, 1H), 5.25 (s, 2H), 4.60 (q, 2H), 1.46 (t, 3H). |
| 36 | δ 8.73 (d, 1H), 7.95 (d, 2H), 7.58 (d, 2H), 7.53 (s, 1H), 7.25 (d, 1H), 5.42 (s, 2H), 2.49 (s, 3H). |
| 37 | δ 8.73 (d, 1H), 8.21 (d, 2H), 7.54 (s, 1H), 7.29 (d, 2H), 7.25 (d, 1H), 5.42 (s, 2H), 2.50 (s, 3H). |
| 38 | δ 8.73 (d, 1H), 8.08 (m, 2H), 7.54 (s, 1H), 7.25 (d, 1H), 7.12 (t, 2H), 5.41 (s, 2H), 2.49 (s, 3H). |
| 39 | δ 8.74 (d, 1H), 8.70 (d, 1H), 7.96 (d, 2H), 7.53 (s, 1H), 7.26 (d, 1H), 5.44 (s, 2H), 2.79 (q, 2H), 1.39 (t, 3H). |
| 40 | δ 8.71 (d, 1H), 8.06 (d, 2H), 7.59 (s, 1H), 7.36 (d, 1H), 7.25 (d, 2H), 5.21 (s, 2H), 4.19 (s, 3H). |
| 41 | δ 8.71 (d, 1H), 8.13 (d, 2H), 7.68 (d, 2H), 7.60 (s, 1H), 7.39 (d, 1H), 5.25 (s, 2H), 4.49 (t, 2H), 1.85 (m, 2H), 1.00 (t, 3H). |

$^a$$^1$H NMR data are in ppm downfield from tetramethylsilane. Couplings are designated by (s)—singlet, (d)—doublet, (t)—triplet, (m)—multiplet and (bs)—broad singlet.

Biological Examples of the Invention

Test A

Seeds of plant species selected from barnyardgrass (*Echinochloa crus-galli*), crabgrass, large (large crabgrass, *Digitaria sanguinalis*), kochia (*Kochia scoparia*), ragweed (common ragweed, *Ambrosia elatior*), foxtail, giant (giant foxtail, *Setaria faberii*), morningglory (*Ipomoea* spp.), pigweed (*Amaranthus retroflexus*), velvetleaf (*Abutilon theophrasti*), ryegrass, Italian (Italian ryegrass, *Lolium multiflorum*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*), were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 500 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Postemergence | | | | | | | | | | | | | | |
| Barnyardgrass | 90 | 90 | 10 | 10 | 30 | 90 | 80 | 100 | 90 | 80 | 50 | 50 | 90 | 20 |
| Blackgrass | — | — | — | — | — | — | — | — | — | — | — | — | — | — |
| Corn | 80 | 90 | 20 | 10 | 20 | 70 | 50 | 90 | 80 | 30 | 50 | 40 | 60 | 20 |
| Crabgrass, Large | 100 | 100 | 40 | 10 | 90 | 90 | 90 | 100 | 100 | 90 | 60 | 90 | 90 | 30 |
| Foxtail, Giant | 100 | 90 | 30 | 10 | 70 | 90 | 90 | 100 | 100 | 90 | 60 | 90 | 90 | 30 |
| *Galium* | — | — | — | — | — | — | — | — | — | — | — | — | — | — |
| *Kochia* | — | — | — | — | — | — | — | — | — | — | — | — | — | — |
| Morningglory | 100 | 90 | 80 | 60 | 100 | 100 | 80 | 100 | 100 | 90 | 90 | 100 | 100 | 80 |
| Pigweed | 100 | 100 | 100 | 80 | 100 | 100 | 100 | 100 | 100 | 100 | 100 | 100 | 100 | 90 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 100 | 100 | 40 | 10 | 60 | 100 | 100 | 100 | 90 | 80 | 100 | 100 | 90 | 50 |
| Wheat | 60 | 70 | 0 | 0 | 10 | 70 | 50 | 100 | 10 | 10 | 20 | 40 | 40 | 30 |

TABLE A-continued

| 500 g ai/ha | Compounds |||||||||||||| 
| --- | --- | --- | --- | --- | --- | --- | --- | --- | --- | --- | --- | --- | --- | --- |
| | 15 | 16 | 17 | 18 | 19 | 20 | 21 | 22 | 23 | 24 | 27 | 28 | 29 | 30 |
| Postemergence |||||||||||||||
| Barnyardgrass | 10 | 70 | 90 | 60 | 0 | 20 | 10 | 60 | 70 | 70 | 90 | 80 | 0 | 90 |
| Blackgrass | — | — | — | — | — | — | — | — | — | 60 | 80 | 40 | — | 80 |
| Corn | 10 | 50 | 70 | 40 | 20 | 20 | 20 | 50 | 60 | 40 | 70 | 40 | 0 | 50 |
| Crabgrass, Large | 10 | 70 | 90 | 90 | 0 | 10 | 20 | 100 | 90 | — | — | — | 0 | — |
| Foxtail, Giant | 10 | 70 | 90 | 90 | 0 | 10 | 20 | 80 | 90 | 90 | 100 | 90 | 0 | 90 |
| *Galium* | — | — | — | — | — | — | — | — | — | 90 | 90 | 80 | — | 90 |
| *Kochia* | — | — | — | — | — | — | — | — | — | 90 | 90 | 90 | — | 90 |
| Morningglory | 10 | 40 | 100 | 100 | 0 | 10 | 30 | 80 | 90 | — | — | — | 0 | — |
| Pigweed | 70 | 100 | 100 | 100 | 30 | 90 | 80 | 100 | 100 | 100 | 100 | 100 | 0 | 100 |
| Ragweed | — | — | — | — | — | — | — | — | — | 70 | 70 | 30 | — | 70 |
| Ryegrass, Italian | — | — | — | — | — | — | — | — | — | 60 | 90 | 50 | — | 80 |
| Velvetleaf | 0 | 40 | 100 | 80 | 0 | 40 | 20 | 100 | 100 | — | — | — | 0 | — |
| Wheat | 0 | 30 | 80 | 30 | 0 | 30 | 10 | 40 | 50 | 30 | 70 | 10 | 0 | 30 |

| 500 g ai/ha | Compounds |||
| --- | --- | --- | --- |
| | 31 | 32 | 33 |
| Postemergence ||||
| Barnyardgrass | 90 | 60 | 50 |
| Blackgrass | 80 | 50 | 50 |
| Corn | 30 | 30 | 30 |
| Crabgrass, Large | — | — | — |
| Foxtail, Giant | 90 | 90 | 90 |
| *Galium* | 90 | 90 | 80 |
| *Kochia* | 90 | 90 | 90 |
| Morningglory | — | — | — |
| Pigweed | 100 | 100 | 100 |
| Ragweed | 80 | 70 | 50 |
| Ryegrass, Italian | 80 | 50 | 40 |
| Velvetleaf | — | — | — |
| Wheat | 40 | 20 | 30 |

| 125 g ai/ha | Compounds ||||||||||||||
| --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 |
| Postemergence |||||||||||||||
| Barnyardgrass | 80 | 20 | 0 | 0 | 10 | 80 | 40 | 100 | 70 | 40 | 0 | 30 | 50 | 10 |
| Blackgrass | — | — | — | — | — | — | — | — | — | — | — | — | — | — |
| Corn | 30 | 20 | 10 | 10 | 10 | 40 | 30 | 50 | 40 | 20 | 20 | 20 | 30 | 10 |
| Crabgrass, Large | 100 | 70 | 10 | 10 | 30 | 90 | 50 | 100 | 90 | 40 | 20 | 50 | 70 | 20 |
| Foxtail, Giant | 90 | 70 | 10 | 10 | 20 | 90 | 60 | 100 | 80 | 50 | 20 | 70 | 80 | 20 |
| *Galium* | — | — | — | — | — | — | — | — | — | — | — | — | — | — |
| *Kochia* | — | — | — | — | — | — | — | — | — | — | — | — | — | — |
| Morningglory | 90 | 70 | 40 | 10 | 50 | 100 | 50 | 90 | 90 | 50 | 80 | 70 | 70 | 40 |
| Pigweed | 100 | 100 | 60 | 40 | 90 | 50 | 100 | 100 | 100 | 100 | 80 | 100 | 100 | 60 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 90 | 30 | 10 | 0 | 30 | 90 | 80 | 90 | 50 | 50 | 50 | 70 | 70 | 30 |
| Wheat | 30 | 0 | 0 | 0 | 0 | 40 | 20 | 40 | 10 | 10 | 10 | 30 | 30 | 10 |

| 125 g ai/ha | Compounds ||||||||||||||
| --- | --- | --- | --- | --- | --- | --- | --- | --- | --- | --- | --- | --- | --- | --- |
| | 15 | 16 | 17 | 18 | 19 | 20 | 21 | 22 | 23 | 24 | 25 | 26 | 27 | 28 |
| Postemergence |||||||||||||||
| Barnyardgrass | 0 | 0 | 70 | 30 | 0 | 0 | 0 | 40 | 50 | 30 | 60 | 70 | 90 | 30 |
| Blackgrass | — | — | — | — | — | — | — | — | — | 40 | 30 | 50 | 70 | 10 |
| Corn | 0 | 10 | 50 | 30 | 0 | 20 | 10 | 20 | 30 | 20 | 30 | 40 | 60 | 10 |
| Crabgrass, Large | 0 | 20 | 90 | 60 | 0 | 20 | 20 | 100 | 70 | — | — | — | — | — |
| Foxtail, Giant | 0 | 30 | 90 | 50 | 0 | 10 | 10 | 70 | 70 | 70 | 90 | 90 | 90 | 70 |
| *Galium* | — | — | — | — | — | — | — | — | — | 70 | 80 | 90 | 80 | 50 |
| *Kochia* | — | — | — | — | — | — | — | — | — | 90 | 90 | 90 | 90 | 90 |
| Morningglory | 0 | 40 | 70 | 50 | 0 | 10 | 20 | 50 | 50 | — | — | — | — | — |
| Pigweed | 10 | 100 | 100 | 100 | 0 | 40 | 30 | 100 | 100 | 90 | 100 | 100 | 100 | 100 |
| Ragweed | — | — | — | — | — | — | — | — | — | 50 | 30 | 50 | 50 | 20 |
| Ryegrass, Italian | — | — | — | — | — | — | — | — | — | 30 | 30 | 50 | 50 | 20 |
| Velvetleaf | 0 | 0 | 90 | 30 | 0 | 0 | 10 | 60 | 70 | — | — | — | — | — |
| Wheat | 0 | 10 | 60 | 20 | 0 | 20 | 0 | 30 | 30 | 20 | 20 | 20 | 20 | 0 |

TABLE A-continued

| 125 g ai/ha | Compounds | | | | | | | | | | | | |
|---|---|---|---|---|---|---|---|---|---|---|---|---|---|
| | 29 | 30 | 31 | 32 | 33 | 34 | 35 | 36 | 37 | 38 | 39 | 40 | 41 |
| Postemergence | | | | | | | | | | | | | |
| Barnyardgrass | 0 | 80 | 50 | 30 | 20 | 70 | 90 | 20 | 0 | 20 | 10 | 0 | 40 |
| Blackgrass | — | 30 | 50 | 20 | 30 | 50 | 50 | 30 | 20 | 40 | 0 | 0 | 30 |
| Corn | 0 | 40 | 20 | 10 | 20 | 20 | 80 | 30 | 20 | 30 | 20 | 20 | 30 |
| Crabgrass, Large | 0 | — | — | — | — | — | — | — | — | — | — | — | — |
| Foxtail, Giant | 0 | 80 | 80 | 60 | 40 | 90 | 90 | 70 | 0 | 80 | 20 | 0 | 50 |
| *Galium* | — | 60 | 70 | 60 | 70 | 90 | 90 | 90 | 20 | 90 | 60 | 30 | 90 |
| *Kochia* | — | 90 | 90 | 80 | 90 | 90 | 90 | 90 | 70 | 90 | 70 | 0 | 90 |
| Morningglory | 0 | — | — | — | — | — | — | — | — | — | — | — | — |
| Pigweed | — | 100 | 100 | 90 | 100 | 100 | 100 | 100 | 80 | 90 | 70 | 70 | 90 |
| Ragweed | — | 40 | 70 | 30 | 30 | 50 | 60 | 30 | 0 | 30 | 30 | 0 | 70 |
| Ryegrass, Italian | — | 50 | 50 | 0 | 10 | 20 | 60 | 0 | 0 | 0 | 0 | 0 | 30 |
| Velvetleaf | 0 | — | — | — | — | — | — | — | — | — | — | — | — |
| Wheat | 0 | 10 | 30 | 0 | 0 | 50 | 70 | 10 | 0 | 10 | 0 | 0 | 20 |

| 31 g ai/ha | Compounds | | | | | | | | | |
|---|---|---|---|---|---|---|---|---|---|---|
| | 25 | 26 | 34 | 35 | 36 | 37 | 38 | 39 | 40 | 41 |
| Postemergence | | | | | | | | | | |
| Barnyardgrass | 20 | 40 | 20 | 80 | 0 | 0 | 0 | 0 | 0 | 30 |
| Blackgrass | 10 | 30 | 20 | 30 | 10 | 0 | 10 | 0 | 0 | 20 |
| Corn | 10 | 30 | 20 | 40 | 20 | 10 | 10 | 0 | 0 | 20 |
| Foxtail, Giant | 50 | 70 | 20 | 80 | 20 | 0 | 20 | 10 | 0 | 30 |
| *Galium* | 60 | 60 | 30 | 90 | 50 | 0 | 30 | 40 | 20 | 60 |
| *Kochia* | 90 | 80 | 70 | 90 | 70 | 20 | 70 | 50 | 0 | 70 |
| Pigweed | 90 | 80 | 100 | 100 | 90 | 20 | 80 | 60 | 30 | 80 |
| Ragweed | 20 | 30 | 20 | 20 | 0 | 0 | 0 | 20 | 0 | 50 |
| Ryegrass, Italian | 10 | 20 | 0 | 30 | 0 | 0 | 0 | 0 | 0 | 20 |
| Wheat | 10 | 20 | 30 | 40 | 0 | 0 | 0 | 0 | 0 | 0 |

| 500 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Preemergence | | | | | | | | | | | | | | |
| Barnyardgrass | 90 | 80 | 0 | 0 | 20 | 100 | 80 | 100 | 100 | 100 | 30 | 80 | 100 | 10 |
| Corn | 20 | 0 | 0 | 0 | 0 | 30 | 10 | 100 | 40 | 20 | 0 | 20 | 10 | 0 |
| Crabgrass, Large | 100 | 100 | 40 | 0 | 100 | 100 | 100 | 100 | 100 | 100 | 90 | 100 | 100 | 100 |
| Foxtail, Giant | 100 | 100 | 30 | 0 | 90 | 100 | 100 | 100 | 100 | 100 | 90 | 100 | 100 | 90 |
| *Kochia* | — | — | — | — | — | — | — | — | — | — | — | — | — | — |
| Morningglory | 80 | 60 | 0 | 0 | 0 | 100 | 60 | 100 | 90 | 20 | 20 | 90 | 70 | 0 |
| Pigweed | 100 | 100 | 80 | 0 | 50 | 100 | 100 | 100 | 100 | 100 | 100 | 100 | 100 | 100 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 100 | 40 | 0 | 0 | 0 | 100 | 70 | 90 | 80 | 30 | 0 | 70 | 80 | 0 |
| Wheat | 30 | 20 | 0 | 0 | 0 | 60 | 10 | 100 | 50 | 20 | 0 | 30 | 0 | 0 |

| 500 g ai/ha | Compounds | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 27 | 28 | 29 | 30 |
| Preemergence | | | | | | | | | | | | | | |
| Barnyardgrass | 0 | 80 | 100 | 60 | 0 | 80 | 0 | 70 | 100 | 90 | 100 | 90 | 0 | 100 |
| Corn | 0 | 0 | 40 | 0 | 0 | 0 | 0 | 20 | 30 | — | — | — | 0 | — |
| Crabgrass, Large | 30 | 100 | 100 | 100 | 50 | 100 | 80 | 100 | 100 | — | — | — | 0 | — |
| Foxtail, Giant | 20 | 90 | 100 | 100 | 50 | 90 | 60 | 100 | 100 | 100 | 100 | 100 | 0 | 100 |
| *Kochia* | — | — | — | — | — | — | — | — | — | 90 | 100 | 90 | — | 100 |
| Morningglory | 0 | 20 | 90 | 40 | 0 | 20 | 0 | 70 | 80 | — | — | — | 0 | — |
| Pigweed | 0 | 100 | 100 | 100 | 0 | 90 | 90 | 100 | 100 | 100 | 100 | 100 | 0 | 100 |
| Ragweed | — | — | — | — | — | — | — | — | — | 40 | 100 | 40 | — | 80 |
| Ryegrass, Italian | — | — | — | — | — | — | — | — | — | 80 | 100 | 90 | — | 100 |
| Velvetleaf | 0 | 20 | 100 | 70 | 0 | 0 | 0 | 40 | 80 | — | — | — | 0 | — |
| Wheat | 0 | 0 | 70 | 0 | 0 | 20 | 0 | 20 | 40 | — | — | — | 0 | — |

TABLE A-continued

| | Compounds | | |
|---|---|---|---|
| 500 g ai/ha | 31 | 32 | 33 |
| Preemergence | | | |
| Barnyardgrass | 90 | 80 | 80 |
| Corn | — | — | — |
| Crabgrass, Large | — | — | — |
| Foxtail, Giant | 100 | 100 | 100 |
| Kochia | 90 | 100 | 90 |
| Morningglory | — | — | — |
| Pigweed | 100 | 100 | 90 |
| Ragweed | 70 | 40 | 30 |
| Ryegrass, Italian | 100 | 60 | 60 |
| Velvetleaf | — | — | — |
| Wheat | — | — | — |

| | Compounds | | | | | | | | | | | | | |
|---|---|---|---|---|---|---|---|---|---|---|---|---|---|---|
| 125 g ai/ha | 1 | 2 | 3 | 4 | 5 | 6 | 7 | 8 | 9 | 10 | 11 | 12 | 13 | 14 |
| Preemergence | | | | | | | | | | | | | | |
| Barnyardgrass | 80 | 0 | 0 | 0 | 0 | 80 | 20 | 100 | 80 | 30 | 0 | 50 | 30 | 0 |
| Corn | 10 | 0 | 0 | 0 | 0 | 20 | 10 | 90 | 0 | 0 | 0 | 0 | 0 | 0 |
| Crabgrass, Large | 100 | 100 | 0 | 0 | 70 | 100 | 90 | 100 | 100 | 100 | 20 | 100 | 100 | 60 |
| Foxtail, Giant | 100 | 80 | 0 | 0 | 60 | 100 | 80 | 100 | 100 | 100 | 20 | 100 | 100 | 30 |
| Kochia | — | — | — | — | — | — | — | — | — | — | — | — | — | — |
| Morningglory | 30 | 0 | 0 | 0 | 0 | 50 | 10 | 100 | 10 | 10 | 0 | 70 | 60 | 0 |
| Pigweed | 100 | 100 | 10 | 0 | 40 | 100 | 90 | 100 | 100 | 100 | 30 | 100 | 100 | 90 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 30 | 0 | 0 | 0 | 0 | 40 | 20 | 70 | 0 | 0 | 0 | 70 | 20 | 0 |
| Wheat | 20 | 0 | 0 | 0 | 0 | 10 | 0 | 80 | 0 | 0 | 0 | 10 | 0 | 0 |

| | Compounds | | | | | | | | | | | | | |
|---|---|---|---|---|---|---|---|---|---|---|---|---|---|---|
| 125 g ai/ha | 15 | 16 | 17 | 18 | 19 | 20 | 21 | 22 | 23 | 24 | 25 | 26 | 27 | 28 |
| Preemergence | | | | | | | | | | | | | | |
| Barnyardgrass | 0 | 0 | 50 | 10 | 0 | 0 | 0 | 40 | 50 | 50 | 70 | 90 | 100 | 30 |
| Corn | 0 | 0 | 30 | 0 | 0 | 0 | 0 | 10 | 20 | — | — | — | — | — |
| Crabgrass, Large | 10 | 60 | 100 | 90 | 0 | 20 | 10 | 100 | 100 | — | — | — | — | — |
| Foxtail, Giant | 0 | 50 | 100 | 90 | 0 | 80 | 0 | 100 | 100 | 100 | 100 | 100 | 100 | 100 |
| Kochia | — | — | — | — | — | — | — | — | — | 80 | 80 | 90 | 100 | 70 |
| Morningglory | 0 | 0 | 70 | 10 | 0 | 0 | 0 | 10 | 50 | — | — | — | — | — |
| Pigweed | 0 | 80 | 100 | 100 | 0 | 20 | 10 | 100 | 100 | 100 | 100 | 100 | 100 | 100 |
| Ragweed | — | — | — | — | — | — | — | — | — | 20 | 20 | 90 | 90 | 10 |
| Ryegrass, Italian | — | — | — | — | — | — | — | — | — | 70 | 50 | 100 | 90 | 20 |
| Velvetleaf | 0 | 0 | 90 | 10 | 0 | 0 | 0 | 20 | 30 | — | — | — | — | — |
| Wheat | 0 | 0 | 30 | 0 | 0 | 0 | 0 | 10 | 20 | — | — | — | — | — |

| | Compounds | | | | | | | | | | | | |
|---|---|---|---|---|---|---|---|---|---|---|---|---|---|
| 125 g ai/ha | 29 | 30 | 31 | 32 | 33 | 34 | 35 | 36 | 37 | 38 | 39 | 40 | 41 |
| Preemergence | | | | | | | | | | | | | |
| Barnyardgrass | 0 | 90 | 90 | 20 | 50 | 100 | 100 | 60 | 0 | 80 | 0 | 0 | 40 |
| Corn | 0 | — | — | — | — | — | — | — | — | — | — | — | — |
| Crabgrass, Large | 0 | — | — | — | — | — | — | — | — | — | — | — | — |
| Foxtail, Giant | 0 | 100 | 100 | 90 | 90 | 100 | 100 | 90 | 0 | 100 | 30 | 0 | 90 |
| Kochia | — | 100 | 90 | 100 | 60 | 90 | 90 | 90 | 0 | 100 | 0 | 0 | 60 |
| Morningglory | 0 | — | — | — | — | — | — | — | — | — | — | — | — |
| Pigweed | 0 | 100 | 100 | 100 | 90 | 100 | 100 | 90 | 20 | 100 | 90 | 30 | 90 |
| Ragweed | — | 80 | 50 | 0 | 20 | 30 | 50 | 20 | 0 | 20 | 0 | 0 | 30 |
| Ryegrass, Italian | — | 90 | 90 | 40 | 30 | 90 | 60 | 10 | 0 | 10 | 0 | 0 | 40 |
| Velvetleaf | 0 | — | — | — | — | — | — | — | — | — | — | — | — |
| Wheat | 0 | — | — | — | — | — | — | — | — | — | — | — | — |

| | Compounds | | | | | | | | |
|---|---|---|---|---|---|---|---|---|---|
| 31 g ai/ha | 25 | 26 | 34 | 35 | 36 | 37 | 38 | 39 | 40 | 41 |
| Preemergence | | | | | | | | | | |
| Barnyardgrass | 10 | 60 | 30 | 80 | 0 | 0 | 0 | 0 | 30 | |
| Foxtail, Giant | 70 | 100 | 100 | 100 | 20 | 0 | 20 | 0 | 0 | 70 |

TABLE A-continued

| | | | | | | | | | | |
|---|---|---|---|---|---|---|---|---|---|---|
| Kochia | 20 | 60 | 20 | 90 | 60 | 0 | 30 | 0 | 0 | 30 |
| Pigweed | 90 | 90 | 100 | 100 | 90 | 10 | 90 | 30 | 0 | 90 |
| Ragweed | 10 | 60 | 0 | 20 | 0 | 0 | 0 | 0 | 0 | 20 |
| Ryegrass, Italian | 0 | 40 | 0 | 30 | 0 | 0 | 0 | 0 | 0 | 20 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

of loam soil and sand and treated preemergence with test chemicals formulated in a non-phytotoxic solvent mixture which included a surfactant.

At the same time, plants selected from these crop and weed species and also chickweed (common chickweed, *Stellaria media*), oat, wild (wild oat, *Avena fatua*), and kochia (*Kochia scoparia*), were planted in pots containing Sunshine Redi-Earth® planting medium comprising spaghnum peat moss, vermiculite, starter nutrients and dolomitic limestone and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 d, after which time all species were compared to controls and visually evaluated. Plant response ratings, summarized in Table C, are based on

TABLE B

| 250 g ai/ha | Compounds | | | | | | | | | | | | | |
|---|---|---|---|---|---|---|---|---|---|---|---|---|---|---|
| | 6 | 7 | 11 | 21 | 22 | 23 | 24 | 25 | 26 | 27 | 28 | 30 | 31 | 32 |
| | Flood | | | | | | | | | | | | | |
| Barnyardgrass | 40 | 0 | 0 | 80 | 0 | 90 | 30 | 35 | 50 | 50 | 20 | 30 | 40 | 0 |
| Ducksalad | 70 | 0 | 0 | 95 | 0 | 90 | 30 | 20 | 70 | 90 | 90 | 80 | 70 | 30 |
| Rice | 50 | 0 | 0 | 25 | 0 | 25 | 0 | 25 | 45 | 30 | 30 | 30 | 35 | 0 |
| Sedge, Umbrella | 80 | 85 | 0 | 90 | 0 | 95 | 85 | 95 | 90 | 95 | 100 | 90 | 100 | 75 |

| 250 g ai/ha | Compound 33 | 125 g ai/ha | Compound 29 |
|---|---|---|---|
| | Flood | | |
| Barnyardgrass | 0 | Barnyardgrass | 0 |
| Ducksalad | 30 | Ducksalad | 0 |
| Rice | 0 | Rice | 0 |
| Sedge, Umbrella | 85 | Sedge, Umbrella | 0 |

| 125 g ai/ha | Compounds | | | | | | | | | | | | |
|---|---|---|---|---|---|---|---|---|---|---|---|---|---|
| | 1 | 2 | 8 | 9 | 10 | 12 | 13 | 14 | 15 | 16 | 17 | 18 | 19 | 20 |
| | Flood | | | | | | | | | | | | |
| Barnyardgrass | 40 | 0 | 50 | 0 | 45 | 0 | 0 | 0 | 0 | 0 | 10 | 0 | 0 | 0 |
| Ducksalad | 20 | 30 | 85 | 20 | 70 | 0 | 65 | 0 | 0 | 0 | 70 | 70 | 0 | 0 |
| Rice | 25 | 20 | 50 | 0 | 20 | 0 | 0 | 0 | 0 | 0 | 15 | 0 | 0 | 0 |
| Sedge, Umbrella | 75 | 75 | 90 | 80 | 80 | 0 | 80 | 0 | 0 | 0 | 80 | 70 | 0 | 0 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), crabgrass, large (large crabgrass, *Digitaria sanguinalis*), foxtail, giant, (giant foxtail, *Setaria faberii*), johnsongrass (*Sorghum halepense*), lambsquarters (*Chenopodium album*), morningglory (*Ipomoea coccinea*), nutsedge, yellow (yellow nutsedge, *Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*), and velvetleaf (*Abutilon theophrasti*) were planted into a blend a scale of 0 to 100 where 0 is no effect and 100 is complete control. A dash (-) response means no test result.

Plant species in the flooded paddy test consisted of rice (*Oryza sativa*), sedge, umbrella (small-flower umbrella sedge, *Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test.

Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

TABLE C

| 250 g ai/ha | \multicolumn{12}{c}{Compounds} |
|---|---|---|---|---|---|---|---|---|---|---|---|---|

| 250 g ai/ha | 1 | 6 | 8 | 24 | 25 | 27 | 28 | 30 | 31 | 32 | 33 | 35 |
|---|---|---|---|---|---|---|---|---|---|---|---|---|
| \multicolumn{13}{c}{Postemergence} |
| Barnyardgrass | 50 | 40 | 75 | 35 | 35 | 55 | 25 | 85 | 75 | 20 | 25 | 85 |
| Blackgrass | 35 | 10 | 75 | 35 | 60 | 50 | 25 | 60 | 80 | 15 | 10 | 85 |
| Chickweed | 95 | 95 | 98 | 85 | 100 | 90 | 90 | 100 | 95 | 50 | 80 | 100 |
| Corn | 20 | 50 | 40 | 30 | 25 | 25 | 15 | 20 | 30 | 35 | 25 | 50 |
| Crabgrass, Large | 45 | 65 | 85 | 35 | 45 | 45 | 30 | 60 | 80 | 25 | 15 | 80 |
| Foxtail, Giant | 55 | 75 | 85 | 20 | 35 | 15 | 10 | 25 | 40 | 10 | 15 | 85 |
| *Galium* | 90 | 90 | 95 | 95 | 90 | 90 | 95 | 90 | 80 | 75 | 80 | 90 |
| Johnsongrass | 20 | 35 | 40 | 20 | 30 | — | 85 | 30 | 70 | 10 | 15 | 100 |
| *Kochia* | 90 | 90 | 95 | 90 | 95 | 95 | 100 | 100 | 90 | 90 | 90 | 90 |
| Lambsquarters | 80 | 85 | 98 | 100 | 98 | 98 | 98 | 95 | 100 | 98 | 90 | 100 |
| Morningglory | 95 | — | 100 | 95 | 95 | 85 | 100 | 100 | 100 | 65 | 75 | 95 |
| Nutsedge, Yellow | 10 | 5 | 10 | 25 | 25 | 10 | 10 | 15 | 35 | 25 | 15 | 35 |
| Oat, Wild | 25 | 10 | 45 | 35 | 35 | 40 | 15 | 45 | 80 | 10 | 25 | 90 |
| Oilsee Rape | 90 | 95 | 95 | 85 | 90 | 90 | 95 | 95 | 90 | 45 | 60 | 98 |
| Pigweed | 100 | 85 | 98 | 100 | 100 | 95 | 100 | 98 | 98 | 98 | 98 | 100 |
| Ragweed | 80 | 80 | 80 | 75 | 85 | 70 | 75 | 85 | 100 | 60 | 75 | 85 |
| Ryegrass, Italian | 5 | 10 | 50 | 25 | 30 | 35 | 15 | 50 | 65 | 10 | 15 | 80 |
| Soybean | 50 | — | 85 | 40 | 65 | 70 | 60 | 75 | 65 | 35 | 65 | 70 |
| Velvetleaf | 75 | 55 | 90 | 60 | 75 | 70 | 80 | 90 | 75 | 20 | 40 | 85 |
| Waterhemp | 90 | 85 | 98 | 98 | 95 | 98 | 98 | 98 | 98 | 98 | 95 | 98 |
| Wheat | 20 | 15 | 40 | 5 | 10 | 15 | 10 | 20 | 20 | 0 | 5 | 30 |

| 125 g ai/ha | 1 | 6 | 8 | 9 | 24 | 25 | 26 | 27 | 28 | 30 | 31 | 32 | 33 | 35 |
|---|---|---|---|---|---|---|---|---|---|---|---|---|---|---|
| \multicolumn{15}{c}{Postemergence} |
| Barnyardgrass | 15 | 25 | 40 | 20 | 35 | 35 | 55 | 25 | 15 | 40 | 45 | 20 | 20 | 60 |
| Blackgrass | 15 | 5 | 55 | 15 | 35 | 30 | 40 | 35 | 15 | 40 | 60 | 5 | 10 | 85 |
| Chickweed | 85 | 85 | 98 | 80 | 65 | 85 | 95 | 90 | 90 | 100 | 95 | 55 | 60 | 100 |
| Corn | 20 | 20 | 25 | 20 | 25 | 25 | 35 | 10 | 15 | 25 | 20 | 25 | 25 | 25 |
| Crabgrass, Large | 45 | 25 | 70 | 25 | 25 | 30 | 50 | 15 | 10 | 35 | 60 | 25 | 10 | 70 |
| Foxtail, Giant | 55 | 45 | 55 | 20 | 20 | 20 | 40 | 10 | 10 | 25 | 40 | 10 | 15 | 70 |
| *Galium* | 90 | 90 | 95 | 65 | 80 | 90 | 90 | 85 | 90 | 90 | 80 | 60 | 75 | 90 |
| Johnsongrass | 15 | 15 | 30 | 10 | 10 | 20 | 55 | 100 | 10 | 35 | 40 | 10 | 10 | 95 |
| *Kochia* | 90 | 90 | 95 | 90 | 90 | 90 | 90 | 95 | 100 | 100 | 90 | 90 | 90 | 90 |
| Lambsquarters | 75 | 85 | 95 | 85 | 100 | 98 | 100 | 98 | 98 | 95 | 100 | 100 | 85 | 98 |
| Morningglory | 70 | 98 | 80 | 75 | 90 | 75 | 85 | 90 | 65 | 80 | 75 | 80 | 85 | 85 |
| Nutsedge, Yellow | 5 | 5 | 10 | 5 | 20 | 25 | 20 | 10 | 15 | 10 | 30 | 10 | 10 | 30 |
| Oat, Wild | 15 | 10 | 35 | 10 | 20 | 25 | 45 | 25 | 10 | 30 | 80 | 5 | 20 | 85 |
| Oilseed Rape | 80 | 95 | 95 | 70 | 85 | 90 | 95 | 90 | 70 | 95 | 85 | 10 | 80 | 80 |
| Pigweed | 98 | 85 | 98 | 85 | 100 | 100 | 98 | 95 | 98 | 98 | 100 | 98 | 98 | 100 |
| Ragweed | 75 | — | 70 | 50 | 75 | 75 | 85 | 25 | 75 | 65 | 85 | 60 | 40 | 80 |
| Ryegrass, Italian | 5 | 5 | 35 | 5 | 20 | 10 | 40 | 30 | 10 | 30 | 40 | 0 | 5 | 60 |
| Soybean | 50 | 60 | 95 | 30 | 55 | 50 | 70 | 65 | 55 | 60 | 35 | 30 | 55 | 65 |
| Velvetleaf | 60 | 55 | 90 | 35 | 60 | 70 | 70 | 60 | 65 | 80 | 65 | 20 | 10 | 80 |
| Waterhemp | 90 | 80 | 95 | 85 | 98 | 98 | 98 | 95 | 95 | 95 | 100 | 90 | 95 | 95 |
| Wheat | 15 | 15 | 30 | 5 | 5 | 5 | 10 | 5 | 5 | 15 | 10 | 0 | 5 | 35 |

| 62 g ai/ha | 1 | 6 | 8 | 9 | 24 | 25 | 26 | 27 | 28 | 30 | 31 | 32 | 33 | 35 |
|---|---|---|---|---|---|---|---|---|---|---|---|---|---|---|
| \multicolumn{15}{c}{Postemergence} |
| Barnyardgrass | 15 | 20 | 20 | 10 | 30 | 25 | 45 | 15 | 15 | 20 | 35 | 15 | 20 | 45 |
| Blackgrass | 5 | 5 | 40 | 5 | 5 | 10 | 40 | 15 | 15 | 30 | 50 | 5 | 5 | 70 |
| Chickweed | 85 | 80 | 98 | 75 | 80 | 90 | 95 | 90 | 95 | 95 | 95 | 10 | 60 | 100 |
| Corn | 15 | 15 | 15 | 35 | 20 | 20 | 30 | 15 | 10 | 10 | 20 | 20 | 30 | 20 |
| Crabgrass, Large | 5 | 15 | 35 | 25 | 10 | 20 | 35 | 20 | 10 | 15 | 35 | 10 | 10 | 60 |
| Foxtail, Giant | 35 | 40 | 40 | 15 | 20 | 20 | 25 | 10 | 10 | 10 | 35 | 10 | 10 | 40 |
| *Galium* | 80 | 80 | 95 | 80 | 80 | 90 | 90 | 90 | 90 | 80 | 80 | 45 | 60 | 80 |
| Johnsongrass | 10 | 10 | 35 | 5 | 20 | 20 | 35 | 45 | 5 | 100 | 25 | 10 | 5 | 85 |
| *Kochia* | 85 | 90 | 95 | 90 | 90 | 90 | 90 | 95 | 90 | 95 | 90 | 90 | 90 | 90 |
| Lambsquarters | 70 | 70 | 98 | 70 | 100 | 90 | 100 | 95 | 80 | 85 | 100 | 95 | 85 | 95 |
| Morningglory | 70 | 95 | 98 | 80 | 98 | 85 | 75 | 80 | 60 | 70 | 60 | 40 | 80 | 95 |
| Nutsedge, Yellow | 5 | 5 | 10 | 0 | 25 | 20 | 30 | 5 | 5 | 5 | 30 | 20 | 10 | 10 |
| Oat, Wild | 10 | 5 | 50 | 5 | 30 | 20 | 40 | 10 | 5 | 15 | 35 | 5 | 10 | 50 |
| Oilseed Rape | 70 | 55 | 95 | 80 | 80 | 90 | 90 | 90 | 55 | 80 | 90 | 5 | 55 | 90 |
| Pigweed | 98 | 80 | 95 | 90 | 100 | 100 | 98 | 85 | 95 | 95 | 98 | 95 | 90 | 98 |

TABLE C-continued

| | | | | | | | | | | | | | | |
|---|---|---|---|---|---|---|---|---|---|---|---|---|---|---|
| Ragweed | 70 | 75 | 50 | 25 | 75 | 80 | 70 | 60 | 25 | 55 | 75 | 70 | 35 | 75 |
| Ryegrass, Italian | 5 | 5 | 35 | 5 | 5 | 5 | 35 | 20 | 5 | 25 | 30 | 0 | 5 | 55 |
| Soybean | 35 | 40 | 75 | 30 | 40 | 70 | 65 | 95 | 70 | 45 | 65 | 25 | 35 | 65 |
| Velvetleaf | 55 | 55 | 70 | 35 | 55 | 50 | 65 | 50 | 60 | 60 | 65 | 10 | 15 | 75 |
| Waterhemp | 85 | 80 | 98 | 80 | 98 | 95 | 98 | 95 | 95 | 98 | 98 | 90 | 95 | 98 |
| Wheat | 10 | 10 | 35 | 0 | 5 | 5 | 10 | 5 | 5 | 5 | 5 | 0 | 5 | 20 |

| | Compounds | | | | | | | | | | | | | |
|---|---|---|---|---|---|---|---|---|---|---|---|---|---|---|
| 31 g ai/ha | 1 | 6 | 8 | 9 | 24 | 25 | 26 | 27 | 28 | 30 | 31 | 32 | 33 | 35 |

Postemergence

| | | | | | | | | | | | | | | |
|---|---|---|---|---|---|---|---|---|---|---|---|---|---|---|
| Barnyardgrass | 10 | 20 | 10 | 10 | 25 | 20 | 30 | 10 | 15 | 25 | 35 | 10 | 10 | 30 |
| Blackgrass | 5 | 5 | 50 | 5 | 5 | 5 | 35 | 10 | 10 | 25 | 35 | 5 | 5 | 65 |
| Chickweed | 60 | 70 | 85 | 75 | 55 | 50 | 95 | 95 | 80 | 95 | 90 | 10 | 55 | 100 |
| Corn | 15 | 10 | 10 | 20 | 20 | 20 | 25 | 10 | 5 | 15 | 40 | 10 | 25 | 25 |
| Crabgrass, Large | 5 | 10 | 20 | 10 | 15 | 15 | 20 | 10 | 10 | 20 | 20 | 5 | 5 | 35 |
| Foxtail, Giant | 35 | 40 | 20 | 15 | 15 | 10 | 20 | 5 | 15 | 5 | 15 | 10 | 10 | 25 |
| Galium | 80 | 80 | 80 | 70 | 70 | 80 | 90 | 90 | 85 | 80 | 80 | 20 | 55 | 80 |
| Johnsongrass | 10 | 10 | 5 | 5 | 10 | 10 | 20 | 5 | — | 30 | 35 | 10 | 5 | 75 |
| Kochia | 85 | 90 | 95 | 90 | 90 | 90 | 90 | 95 | 95 | 100 | 90 | 80 | 90 | 90 |
| Lambsquarters | 70 | 65 | 95 | 55 | 100 | 90 | 100 | 85 | 100 | 70 | 98 | 100 | 80 | 98 |
| Morningglory | 60 | 90 | 85 | 85 | 98 | 90 | 90 | 85 | 70 | 80 | 95 | 80 | 55 | 70 |
| Nutsedge, Yellow | 5 | 5 | 5 | 0 | 15 | 20 | 25 | 5 | 5 | 5 | 20 | 5 | 5 | 20 |
| Oat, Wild | 5 | 5 | 45 | 5 | 15 | 10 | 35 | 10 | 5 | 25 | 30 | 0 | 10 | 45 |
| Oilseed Rape | 50 | 55 | 90 | 55 | 50 | 90 | 98 | 90 | 25 | 35 | 85 | 20 | 40 | 80 |
| Pigweed | 50 | 80 | 95 | 85 | 100 | 100 | 95 | 85 | 95 | 95 | 95 | 98 | 95 | 98 |
| Ragweed | 60 | 75 | 45 | 25 | 65 | 65 | 90 | 55 | 25 | 65 | 70 | 35 | 35 | 65 |
| Ryegrass, Italian | 5 | 5 | 30 | 5 | 5 | 5 | 35 | 5 | 5 | 20 | 20 | 0 | 0 | 30 |
| Soybean | 20 | 35 | 65 | 25 | 55 | 45 | 70 | 70 | 45 | 25 | 40 | 20 | 25 | 55 |
| Velvetleaf | 40 | 55 | 50 | 35 | 60 | 35 | 60 | 45 | 60 | 55 | 45 | 15 | 15 | 65 |
| Waterhemp | 85 | 80 | 95 | 65 | 100 | 95 | 98 | 90 | 98 | 95 | 95 | 85 | 80 | 98 |
| Wheat | 10 | 5 | 30 | 0 | 5 | 5 | 10 | 5 | 0 | 5 | 5 | 0 | 5 | 15 |

| | Compounds | |
|---|---|---|
| 16 g ai/ha | 9 | 26 |

Postemergence

| | | |
|---|---|---|
| Barnyardgrass | 5 | 25 |
| Blackgrass | 5 | 15 |
| Chickweed | 70 | 90 |
| Corn | 10 | 25 |
| Crabgrass, Large | 10 | 20 |
| Foxtail, Giant | 10 | 10 |
| Galium | 50 | 80 |
| Johnsongrass | 0 | 25 |
| Kochia | 95 | 85 |
| Lambsquarters | 65 | 100 |
| Morningglory | 70 | 90 |
| Nutsedge, Yellow | 0 | 15 |
| Oat, Wild | 5 | 35 |
| Oilseed Rape | 40 | 90 |
| Pigweed | 75 | 95 |
| Ragweed | 15 | 85 |
| Ryegrass, Italian | 0 | 20 |
| Soybean | 15 | 35 |
| Velvetleaf | 25 | 60 |
| Waterhemp | 70 | 95 |
| Wheat | 0 | 5 |

| | Compounds | | | | | | | | |
|---|---|---|---|---|---|---|---|---|---|
| 250 g ai/ha | 1 | 6 | 8 | 9 | 24 | 27 | 30 | 31 | 32 | 35 |

Preemergence

| | | | | | | | | | | |
|---|---|---|---|---|---|---|---|---|---|---|
| Barnyardgrass | 70 | 98 | 100 | 85 | 85 | 100 | 98 | 95 | 75 | 100 |
| Blackgrass | 85 | 95 | 90 | 90 | 90 | 90 | 90 | 95 | 90 | 90 |
| Corn | 40 | 50 | 65 | 55 | 40 | 60 | 35 | 25 | 20 | 45 |
| Crabgrass, Large | 100 | 100 | 100 | 100 | 100 | 100 | 100 | 100 | 98 | 100 |
| Foxtail, Giant | 100 | 100 | 100 | 100 | 100 | 100 | 100 | 100 | 100 | 100 |
| Galium | 100 | 100 | 100 | 98 | 90 | 95 | 95 | 35 | 80 | 90 |
| Johnsongrass | 80 | 100 | 100 | 80 | 85 | 100 | 95 | 95 | 60 | 98 |
| Lambsquarters | 98 | 98 | 100 | 98 | 85 | 100 | 98 | 98 | 90 | 98 |
| Morningglory | 90 | 100 | 100 | 90 | 40 | 95 | 90 | 65 | 45 | 90 |
| Nutsedge, Yellow | 15 | 50 | 80 | 50 | 15 | 60 | 10 | 5 | 20 | 0 |
| Oilseed Rape | 100 | 100 | 100 | 100 | 98 | 100 | 100 | 85 | 85 | 90 |

TABLE C-continued

| | | | | | | | | | | |
|---|---|---|---|---|---|---|---|---|---|---|
| Pigweed | 100 | 100 | 100 | 98 | 100 | 100 | 100 | 100 | 100 | 100 |
| Ragweed | 70 | 80 | 90 | 85 | 55 | 98 | 90 | 75 | 65 | 90 |
| Ryegrass, Italian | — | 100 | 90 | 85 | 90 | 95 | 70 | 90 | 10 | 90 |
| Soybean | 20 | 70 | 75 | 40 | 35 | 75 | 40 | 10 | 5 | 65 |
| Velvetleaf | 75 | 100 | 100 | 60 | 60 | 100 | 85 | 80 | 60 | 90 |
| Waterhemp | — | — | 100 | 100 | 100 | 100 | 100 | 100 | 100 | 100 |
| Wheat | 5 | 60 | 80 | 25 | 5 | 60 | 35 | 35 | 0 | 35 |

| | Compounds | | | | | | | | | |
|---|---|---|---|---|---|---|---|---|---|---|
| 125 g ai/ha | 1 | 6 | 8 | 9 | 24 | 27 | 30 | 31 | 32 | 35 |
| | Preemergence | | | | | | | | | |
| Barnyardgrass | 55 | 95 | 100 | 70 | 80 | 100 | 85 | 90 | 10 | 98 |
| Blackgrass | 80 | 95 | 90 | 90 | 90 | 50 | 90 | 90 | 10 | 90 |
| Corn | 25 | 50 | 65 | 25 | 25 | 55 | 30 | 20 | 5 | 35 |
| Crabgrass, Large | 100 | 100 | 100 | 100 | 100 | 100 | 100 | 100 | 100 | 100 |
| Foxtail, Giant | 100 | 100 | 100 | 100 | 98 | 100 | 100 | 98 | 85 | 100 |
| *Galium* | 100 | 100 | 100 | 90 | 50 | 95 | 95 | 30 | 60 | 90 |
| Johnsongrass | 55 | 85 | 98 | 65 | 55 | 80 | 85 | 85 | 30 | 95 |
| Lambsquarters | 98 | 98 | 100 | 98 | 85 | 98 | 95 | 100 | 80 | 100 |
| Morningglory | 55 | 75 | 98 | 45 | 35 | 100 | 60 | 55 | 5 | 80 |
| Nutsedge, Yellow | — | 35 | 55 | 35 | 5 | 35 | 0 | 5 | 5 | 0 |
| Oilseed Rape | 100 | 100 | 100 | 95 | 35 | 100 | 100 | 45 | 10 | 90 |
| Pigweed | 100 | 100 | 100 | 100 | 100 | 100 | 100 | 100 | 100 | 100 |
| Ragweed | 60 | 55 | 90 | 60 | 25 | 98 | 80 | 65 | 10 | 85 |
| Ryegrass, Italian | 90 | 80 | 90 | 65 | 85 | 90 | 70 | 90 | 0 | 90 |
| Soybean | 10 | 55 | 60 | 15 | 20 | 55 | 15 | 15 | 0 | 60 |
| Velvetleaf | 75 | 100 | 95 | 35 | 35 | 95 | 75 | 65 | 55 | 80 |
| Waterhemp | — | — | 98 | 100 | 100 | 100 | 100 | 100 | 100 | 100 |
| Wheat | 0 | 45 | 75 | 5 | 0 | 35 | 5 | 5 | 0 | 5 |

| | Compounds | | | | | | | | | |
|---|---|---|---|---|---|---|---|---|---|---|
| 62 g ai/ha | 1 | 6 | 8 | 9 | 24 | 27 | 30 | 31 | 32 | 35 |
| | Preemergence | | | | | | | | | |
| Barnyardgrass | 35 | 75 | 100 | 35 | 45 | 90 | 85 | 80 | 5 | 90 |
| Blackgrass | 75 | 90 | 90 | 85 | 60 | 5 | 80 | 70 | 0 | 85 |
| Corn | 15 | 35 | 55 | 5 | 10 | 40 | 15 | 0 | 0 | 15 |
| Crabgrass, Large | 100 | 100 | 100 | 100 | 98 | 100 | 100 | 98 | 90 | 100 |
| Foxtail, Giant | 98 | 100 | 100 | 100 | 95 | 100 | 100 | 95 | 70 | 100 |
| *Galium* | 98 | 98 | 100 | 5 | 30 | 95 | 65 | 30 | 0 | 80 |
| Johnsongrass | 35 | 75 | 98 | 20 | 40 | 80 | 65 | 80 | 0 | 95 |
| Lambsquarters | 98 | 98 | 98 | 85 | 75 | 98 | 98 | 100 | 60 | 98 |
| Morningglory | 55 | 60 | 100 | 45 | 30 | 80 | 35 | 45 | 5 | 60 |
| Nutsedge, Yellow | 5 | 30 | 40 | 5 | 0 | 10 | 0 | 0 | 0 | 0 |
| Oilseed Rape | 90 | 100 | 95 | 60 | 30 | 90 | 80 | 20 | 20 | 75 |
| Pigweed | 100 | 100 | 100 | 100 | 100 | 100 | 100 | 100 | 100 | 100 |
| Ragweed | 50 | 20 | 85 | 60 | 25 | 50 | 65 | 50 | 5 | 75 |
| Ryegrass, Italian | 10 | 70 | 80 | 25 | 15 | 30 | 60 | 60 | 0 | 85 |
| Soybean | 5 | 5 | 35 | 0 | 5 | 40 | 5 | 5 | 0 | 15 |
| Velvetleaf | 30 | 75 | 85 | 25 | 45 | 70 | 70 | 55 | 10 | 65 |
| Waterhemp | — | — | 100 | 100 | 100 | 100 | 100 | 100 | 100 | 100 |
| Wheat | 0 | 10 | 45 | 5 | 0 | 25 | 0 | 5 | 0 | 5 |

| | Compounds | | | | | | | | | |
|---|---|---|---|---|---|---|---|---|---|---|
| 31 g ai/ha | 1 | 6 | 8 | 9 | 24 | 27 | 30 | 31 | 32 | 35 |
| | Preemergence | | | | | | | | | |
| Barnyardgrass | 10 | 50 | 98 | 5 | 10 | 70 | 40 | 70 | 0 | 85 |
| Blackgrass | 5 | 70 | 90 | 5 | 10 | 5 | 60 | 80 | 0 | 90 |
| Corn | 5 | 15 | 35 | 0 | 0 | 25 | 5 | 0 | 0 | 5 |
| Crabgrass, Large | 98 | 100 | 100 | 95 | 98 | 100 | 98 | 98 | 65 | 100 |
| Foxtail, Giant | 98 | 100 | 100 | 80 | 80 | 100 | 98 | 90 | 5 | 98 |
| *Galium* | 70 | 90 | 80 | 5 | 5 | 90 | 60 | 5 | 0 | 50 |
| Johnsongrass | 25 | 60 | 85 | 5 | 10 | 45 | 35 | 75 | 0 | 90 |
| Lambsquarters | 90 | 98 | 95 | 70 | 60 | 90 | 98 | 90 | 60 | 98 |
| Morningglory | 20 | 45 | 85 | 5 | 10 | 20 | 35 | 25 | 0 | 70 |
| Nutsedge, Yellow | 0 | 25 | 10 | 10 | 0 | 5 | 0 | 0 | 0 | 0 |
| Oilseed Rape | 25 | 70 | 95 | 0 | 5 | 90 | 80 | 10 | 5 | 80 |
| Pigweed | 100 | 100 | 100 | 100 | 100 | 100 | 100 | 98 | 100 | 98 |
| Ragweed | 35 | 20 | 75 | 25 | 5 | 50 | 55 | 45 | 0 | 60 |
| Ryegrass, Italian | 5 | 30 | 50 | 5 | 5 | 25 | 5 | 50 | 0 | 70 |
| Soybean | 0 | 5 | 15 | 0 | 0 | 35 | 10 | 5 | 0 | 20 |
| Velvetleaf | 15 | 20 | 70 | 20 | 30 | 10 | 20 | 35 | 20 | 70 |

TABLE C-continued

|  |  |  | | | | | | | | |
|---|---|---|---|---|---|---|---|---|---|---|
| Waterhemp | — | — | 98 | 100 | 100 | 100 | 100 | 100 | 90 | 100 |
| Wheat | 0 | 0 | 35 | 0 | 0 | 20 | 0 | 0 | 0 | 5 |

| | Compounds | | | | | Compounds | | | |
|---|---|---|---|---|---|---|---|---|---|
| 250 g ai/ha | 3 | 4 | 5 | 23 | 125 g ai/ha | 3 | 4 | 5 | 23 |
| | | | | Flood | | | | | |
| Barnyardgrass | 20 | 0 | 15 | 20 | Barnyardgrass | 20 | 0 | 15 | 15 |
| Ducksalad | 40 | 0 | 60 | 80 | Ducksalad | 30 | 0 | 40 | 75 |
| Rice | 0 | 0 | 0 | 0 | Rice | 0 | 0 | 0 | 0 |
| Sedge, Umbrella | 50 | 0 | 40 | 95 | Sedge, Umbrella | 40 | 0 | 20 | 90 |

| | Compounds | | | | | Compounds | | | |
|---|---|---|---|---|---|---|---|---|---|
| 62 g ai/ha | 3 | 4 | 5 | 23 | 31 g ai/ha | 3 | 4 | 5 | 23 |
| | | | | Flood | | | | | |
| Barnyardgrass | 20 | 0 | 10 | 10 | Barnyardgrass | 0 | 0 | 10 | 0 |
| Ducksalad | 20 | 0 | 30 | 45 | Ducksalad | 0 | 0 | 20 | 30 |
| Rice | 0 | 0 | 0 | 0 | Rice | 0 | 0 | 0 | 0 |
| Sedge, Umbrella | 0 | 0 | 0 | 85 | Sedge, Umbrella | 0 | 0 | 0 | 80 |

Test D

Seeds of plant species selected from bluegrass (annual bluegrass, *Poa annua*), blackgrass (*Alopecurus myosuroides*), canarygrass (*Phalaris minor*), chickweed (common chickweed, *Stellaria media*), galium (catchweed bedstraw, *Galium aparine*), bromegrass, down (downy bromegrass, *Bromus tectorum*), Russian thistle (*Salsola kali*), field poppy (*Papaver rhoeas*), field violet (*Viola arvensis*), foxtail, green (green foxtail, *Setaria viridis*), deadnettle (henbit deadnettle, *Lamium amplexicaule*), ryegrass, Ital. (Italian ryegrass, *Lolium multiflorum*), kochia (*Kochia scoparia*), lambsquarters (*Chenopodium album*), oilseed rape (*Brassica napus*), pigweed (*Amaranthus retroflexus*), chamomile (scentless chamomile, *Matricaria inodora*), speedwell (bird's-eye speedwell, *Veronica persica*), barley, spring (spring barley, *Hordeum vulgare*), wheat, spring (spring wheat, *Triticum aestivum*), buckwheat, wild (wild buckwheat, *Polygonum convolvulus*), wild mustard (*Sinapis arvensis*), oat, wild (wild oat, *Avena fatua*), radish, wild (wild radish, *Raphanus raphanistrum*), windgrass (*Apera spica-venti*), barley, winter (winter barley, *Hordeum vulgare*), and wheat, winter (winter wheat, *Triticum aestivum*) were planted into a silt loam soil and treated preemergence with test chemicals formulated in a non-phytotoxic solvent mixture which included a surfactant.

At the same time, these species were planted in pots containing Sunshine Redi-Earth® planting medium comprising spaghnum peat moss, vermiculite, starter nutrients and dolomitic limestone and treated with postemergence applications of the test chemicals formulated in the same manner. Plants ranged in height from 2 to 18 cm (1- to 4-leaf stage). Treated plants and controls were maintained in a controlled growth environment for 14 to 21 d after which time all species were compared to controls and visually evaluated. Plant response ratings, summarized in Table D, are based on a scale of 0 to 100 where 0 is no effect and 100 is complete control. A dash (-) response means no test result.

TABLE D

| | Compounds | | | Compounds | | | | | | | |
|---|---|---|---|---|---|---|---|---|---|---|---|
| 250 g ai/ha | 1 | 8 | 125 g ai/ha | 1 | 8 | 24 | 27 | 28 | 30 | 31 | 35 |
| | | | Postemergence | | | | | | | | |
| Barley, Spring | 40 | 35 | Barley, Spring | 35 | 35 | 35 | 35 | 25 | 45 | 50 | 50 |
| Barley, Winter | 40 | 35 | Barley, Winter | 35 | 35 | 25 | 35 | 25 | 40 | 50 | 50 |
| Blackgrass | 45 | 70 | Blackgrass | 30 | 75 | 65 | 65 | 60 | 75 | 80 | 80 |
| Bluegrass | 55 | 75 | Bluegrass | 35 | 75 | 70 | 70 | 40 | 80 | 85 | 95 |
| Bromegrass, Down | 35 | 60 | Bromegrass, Down | 25 | 55 | 50 | 65 | 35 | 65 | 70 | 75 |
| Buckwheat, Wild | 100 | 95 | Buckwheat, Wild | 100 | 95 | 70 | 85 | 95 | 85 | 75 | 95 |
| Canarygrass | 65 | 75 | Canarygrass | 35 | 65 | 70 | 60 | 50 | 80 | 80 | 80 |
| Chamomile | 65 | 65 | Chamomile | 55 | 60 | 30 | 35 | 25 | 70 | 80 | 100 |
| Chickweed | 90 | 90 | Chickweed | 85 | 85 | 90 | 100 | 90 | 100 | 100 | 100 |
| Deadnettle | 85 | 90 | Deadnettle | 70 | 95 | 85 | 100 | 75 | 100 | 95 | 90 |
| Field Poppy | 100 | 100 | Field Poppy | 100 | 95 | 100 | 100 | 70 | 100 | 100 | 100 |
| Field Violet | 100 | 100 | Field Violet | 100 | 90 | 90 | 80 | 100 | 100 | 100 | 100 |
| Foxtail, Green | 75 | 85 | Foxtail, Green | 65 | 75 | 65 | 95 | 80 | 90 | 85 | 95 |
| *Galium* | 90 | 95 | *Galium* | 90 | 95 | 75 | 100 | 80 | 85 | 90 | 80 |
| *Kochia* | 80 | 80 | *Kochia* | 80 | 85 | 90 | 100 | 95 | 95 | 95 | 90 |
| Lambsquarters | 90 | 90 | Lambsquarters | 85 | 95 | 85 | 95 | 95 | 95 | 90 | 100 |
| Mustard, Wild | 100 | 100 | Mustard, Wild | 100 | 100 | 100 | 100 | 100 | 100 | 100 | 100 |
| Oat, Wild | 45 | 55 | Oat, Wild | 35 | 45 | 55 | 60 | 50 | 75 | 75 | 80 |
| Oilseed Rape | 100 | 100 | Oilseed Rape | 100 | 100 | 85 | 100 | 85 | 100 | 100 | 100 |
| Pigweed | 85 | 95 | Pigweed | 85 | 100 | 100 | 100 | 100 | 100 | 100 | 100 |

TABLE D-continued

| | | |
|---|---|---|
| Radish, Wild | 95 | 100 |
| Ryegrass, Ital. | 35 | 55 |
| Speedwell | 100 | 100 |
| Wheat, Spring | 45 | 35 |
| Wheat, Winter | 35 | 35 |
| Windgrass | 60 | 85 |

| | | | | | | | | |
|---|---|---|---|---|---|---|---|---|
| Radish, Wild | 95 | 100 | 95 | 100 | 100 | 100 | 100 | 100 |
| Russian Thistle | — | — | 85 | 85 | 85 | 90 | 90 | 85 |
| Ryegrass, Ital. | 20 | 55 | 40 | 60 | 45 | 70 | 65 | 75 |
| Speedwell | 100 | 100 | 90 | 95 | 80 | 100 | 100 | 100 |
| Wheat, Spring | 35 | 35 | 15 | 35 | 25 | 45 | 45 | 50 |
| Wheat, Winter | 25 | 35 | 20 | 30 | 20 | 35 | 30 | 45 |
| Windgrass | 30 | 75 | 60 | 70 | 45 | 85 | 80 | 90 |

| | Compounds | | | | | | |
|---|---|---|---|---|---|---|---|
| 62 g ai/ha | 1 | 8 | 24 | 27 | 28 | 30 | 31 | 35 |
| Postemergence | | | | | | | | |
| Barley, Spring | 35 | 30 | 30 | 35 | 20 | 35 | 45 | 40 |
| Barley, Winter | 25 | 30 | 25 | 30 | 20 | 30 | 40 | 40 |
| Blackgrass | 20 | 50 | 45 | 55 | 55 | 65 | 70 | 70 |
| Bluegrass | 20 | 65 | 60 | 65 | 45 | 75 | 75 | 75 |
| Bromegrass, Down | 20 | 45 | 45 | 50 | 25 | 65 | 50 | 60 |
| Buckwheat, Wild | 80 | 70 | 60 | 70 | 75 | 85 | 75 | 70 |
| Canarygrass | 20 | 60 | 60 | 70 | 45 | 75 | 80 | 75 |
| Chamomile | 35 | 50 | 20 | 20 | 15 | 40 | 65 | 95 |
| Chickweed | 80 | 85 | 70 | 100 | 70 | 100 | 100 | 100 |
| Deadnettle | 60 | 80 | 70 | 95 | 70 | 90 | 80 | 75 |
| Field Poppy | 100 | 90 | 80 | 85 | 65 | 98 | 98 | 95 |
| Field Violet | 100 | 75 | 80 | 80 | 100 | 95 | 100 | 100 |
| Foxtail, Green | 45 | 75 | 65 | 80 | 60 | 85 | 80 | 95 |
| *Galium* | 70 | 90 | 65 | 100 | 75 | 80 | 80 | 80 |
| *Kochia* | 75 | 80 | 90 | 95 | 85 | 90 | 90 | 90 |
| Lambsquarters | 80 | 95 | 80 | 95 | 85 | 95 | 85 | 95 |
| Mustard, Wild | 100 | 100 | 100 | 100 | 100 | 100 | 100 | 100 |
| Oat, Wild | 30 | 45 | 50 | 50 | 45 | 65 | 70 | 75 |
| Oilseed Rape | 80 | 75 | 80 | 90 | 75 | 100 | 90 | 100 |
| Pigweed | 85 | 95 | 100 | 100 | 100 | 100 | 100 | 100 |
| Radish, Wild | 100 | 100 | 95 | 100 | 95 | 98 | 95 | 100 |
| Russian Thistle | — | — | 85 | 85 | 85 | 90 | 85 | 80 |
| Ryegrass, Ital. | 15 | 35 | 30 | 35 | 30 | 65 | 55 | 65 |
| Speedwell | 100 | 100 | 75 | 95 | 85 | 100 | 100 | 90 |
| Wheat, Spring | 25 | 25 | 25 | 20 | 20 | 35 | 40 | 50 |
| Wheat, Winter | 15 | 35 | 20 | 30 | 25 | 25 | 20 | 40 |
| Windgrass | 20 | 60 | 45 | 70 | 45 | 75 | 75 | 80 |

| | Compounds | | | | | | |
|---|---|---|---|---|---|---|---|
| 31 g ai/ha | 1 | 8 | 24 | 27 | 28 | 30 | 31 | 35 |
| Postemergence | | | | | | | | |
| Barley, Spring | 20 | 25 | 25 | 25 | 20 | 40 | 45 | 40 |
| Barley, Winter | 20 | 20 | 15 | 25 | 15 | 25 | 35 | 40 |
| Blackgrass | 10 | 50 | 35 | 50 | 35 | 60 | 65 | 55 |
| Bluegrass | 10 | 55 | 35 | 60 | 20 | 70 | 65 | 70 |
| Bromegrass, Down | 15 | 35 | 40 | 30 | 20 | 45 | 45 | 55 |
| Buckwheat, Wild | 60 | 70 | 55 | 80 | 65 | 70 | 75 | 70 |
| Canarygrass | 15 | 55 | 55 | 65 | 30 | 65 | 75 | 70 |
| Chamomile | 25 | 50 | 20 | 15 | 15 | 30 | 35 | 75 |
| Chickweed | 75 | 80 | 60 | 95 | 70 | 80 | 90 | 85 |
| Deadnettle | 65 | 75 | 60 | 75 | 60 | 75 | 75 | 65 |
| Field Poppy | 70 | 80 | 75 | 80 | 65 | 90 | 80 | 95 |
| Field Violet | 100 | 70 | 75 | 75 | 80 | 98 | 100 | 100 |
| Foxtail, Green | 25 | 40 | 25 | 65 | 35 | 75 | 80 | 80 |
| *Galium* | 70 | 75 | 70 | 75 | 70 | 75 | 75 | 75 |
| *Kochia* | 65 | 75 | 90 | 95 | 85 | 90 | 85 | 90 |
| Lambsquarters | 75 | 95 | 75 | 95 | 90 | 90 | 95 | 95 |
| Mustard, Wild | 100 | 100 | 70 | 100 | 100 | 100 | 100 | 100 |
| Oat, Wild | 25 | 35 | 45 | 45 | 40 | 40 | 45 | 65 |
| Oilseed Rape | 70 | 70 | 75 | 85 | 75 | 75 | 85 | 90 |
| Pigweed | 80 | 95 | 100 | 100 | 100 | 100 | 100 | 100 |
| Radish, Wild | 75 | 80 | 95 | 90 | 95 | 95 | 95 | 100 |
| Russian Thistle | — | — | 75 | 80 | 75 | 90 | 80 | 75 |
| Ryegrass, Ital. | 10 | 35 | 25 | 20 | 20 | 60 | 30 | 60 |
| Speedwell | 100 | 100 | 75 | 85 | 75 | 100 | 90 | 85 |
| Wheat, Spring | 20 | 25 | 15 | 15 | 15 | 30 | 35 | 40 |
| Wheat, Winter | 15 | 25 | 15 | 25 | 20 | 15 | 20 | 35 |
| Windgrass | 15 | 40 | 35 | 65 | 25 | 65 | 70 | 75 |

TABLE D-continued

| 16 g ai/ha | Compounds | | | | | |
|---|---|---|---|---|---|---|
| | 24 | 27 | 28 | 30 | 31 | 35 |
| Postemergence | | | | | | |
| Barley, Spring | 20 | 25 | 15 | 30 | 35 | 30 |
| Barley, Winter | 15 | 15 | 10 | 20 | 25 | 25 |
| Blackgrass | 25 | 45 | 25 | 45 | 45 | 35 |
| Bluegrass | 15 | 35 | 20 | 65 | 50 | 45 |
| Bromegrass, Down | 25 | 25 | 20 | 30 | 25 | 40 |
| Buckwheat, Wild | 50 | 65 | 60 | 70 | 65 | 65 |
| Canarygrass | 45 | 50 | 25 | 55 | 65 | 65 |
| Chamomile | 30 | 15 | 10 | 20 | 20 | 70 |
| Chickweed | 55 | 85 | 65 | 70 | 80 | 70 |
| Deadnettle | 40 | 55 | 50 | 70 | 75 | 55 |
| Field Poppy | 60 | 75 | 65 | 70 | 75 | 80 |
| Field Violet | 70 | 70 | 75 | 75 | 100 | 90 |
| Foxtail, Green | 15 | 35 | 25 | 55 | 70 | 70 |
| *Galium* | 55 | 70 | 65 | 70 | 70 | 70 |
| *Kochia* | 85 | 85 | 85 | 85 | 80 | 90 |
| Lambsquarters | 65 | 85 | 75 | 85 | 75 | 85 |
| Mustard, Wild | 65 | 80 | 90 | 90 | 100 | 70 |
| Oat, Wild | 35 | 35 | 30 | 40 | 35 | 40 |
| Oilseed Rape | 65 | 80 | 65 | 90 | 80 | 80 |
| Pigweed | 95 | 100 | 100 | 100 | 100 | 100 |
| Radish, Wild | 70 | 85 | 85 | 95 | 95 | 85 |
| Russian Thistle | 65 | 75 | 70 | 80 | 70 | 70 |
| Ryegrass, Ital. | 15 | 15 | 20 | 35 | 25 | 30 |
| Speedwell | 75 | 75 | 75 | 100 | 95 | 75 |
| Wheat, Spring | 15 | 15 | 10 | 25 | 30 | 25 |
| Wheat, Winter | 15 | 25 | 15 | 15 | 20 | 20 |
| Windgrass | 20 | 60 | 25 | 45 | 60 | 55 |

| 250 g ai/ha | Compounds | | 125 g ai/ha | Compounds | | | | | | |
|---|---|---|---|---|---|---|---|---|---|---|
| | 1 | 8 | | 1 | 8 | 24 | 27 | 28 | 30 | 31 | 35 |
| Preemergence | | | | | | | | | | |
| Barley, Spring | 5 | 60 | Barley, Spring | 0 | 45 | 35 | 35 | 25 | 45 | 50 | 50 |
| Barley, Winter | 20 | 45 | Barley, Winter | 10 | 35 | 25 | 35 | 25 | 40 | 50 | 50 |
| Blackgrass | 65 | 100 | Blackgrass | 35 | 100 | 65 | 70 | 50 | 70 | 75 | 95 |
| Bluegrass | 100 | 100 | Bluegrass | 60 | 100 | 98 | 100 | 85 | 100 | 100 | 100 |
| Bromegrass, Down | 10 | 100 | Bromegrass, Down | 10 | 100 | 40 | 70 | 45 | 70 | 55 | 75 |
| Buckwheat, Wild | 100 | 100 | Buckwheat, Wild | 65 | 100 | 70 | 85 | 95 | 85 | 75 | 95 |
| Canarygrass | 100 | 100 | Canarygrass | 60 | 100 | 75 | 98 | 65 | 100 | 100 | 100 |
| Chamomile | 100 | 100 | Chamomile | 80 | 100 | 90 | 100 | 95 | 100 | 100 | 100 |
| Chickweed | 100 | 100 | Chickweed | 100 | 100 | 90 | 100 | 90 | 100 | 100 | 100 |
| Deadnettle | 100 | 100 | Deadnettle | 100 | 100 | 100 | 100 | 100 | 100 | 100 | 100 |
| Field Poppy | 100 | 100 | Field Poppy | 100 | 100 | 100 | 100 | 100 | 100 | 100 | 100 |
| Field Violet | 100 | 100 | Field Violet | 100 | 100 | 100 | 100 | 100 | 100 | 100 | 100 |
| Foxtail, Green | 100 | 100 | Foxtail, Green | 100 | 100 | 100 | 100 | 100 | 100 | 100 | 100 |
| *Galium* | 100 | 70 | *Galium* | 60 | 50 | 75 | 100 | 80 | 85 | 90 | 80 |
| *Kochia* | 100 | 100 | *Kochia* | 100 | 100 | 90 | 100 | 95 | 95 | 95 | 90 |
| Lambsquarters | 100 | 100 | Lambsquarters | 100 | 100 | 85 | 95 | 95 | 95 | 90 | 100 |
| Mustard, Wild | 100 | 100 | Mustard, Wild | 100 | 100 | 100 | 100 | 100 | 100 | 100 | 100 |
| Oat, Wild | 45 | 80 | Oat, Wild | 15 | 70 | 35 | 75 | 35 | 80 | 75 | 80 |
| Oilseed Rape | 100 | 100 | Oilseed Rape | 100 | 100 | 70 | 80 | 15 | 55 | 35 | 100 |
| Pigweed | 100 | 100 | Pigweed | 100 | 100 | 100 | 100 | 100 | 100 | 100 | 100 |
| Radish, Wild | 100 | 100 | Radish, Wild | 100 | 100 | 100 | 100 | 80 | 100 | 100 | 100 |
| Ryegrass, Ital. | 35 | 100 | Russian Thistle | — | — | 85 | 85 | 85 | 90 | 90 | 85 |
| Speedwell | 100 | 100 | Ryegrass, Ital. | 30 | 95 | 45 | 75 | 55 | 70 | 100 | 70 |
| Wheat, Spring | 5 | 70 | Speedwell | 100 | 100 | 100 | 100 | 100 | 100 | 100 | 100 |
| Wheat, Winter | 0 | 65 | Wheat, Spring | 0 | 35 | 15 | 35 | 25 | 45 | 45 | 50 |
| Windgrass | 100 | 100 | Wheat, Winter | 0 | 40 | 20 | 30 | 20 | 35 | 30 | 45 |
| | | | Windgrass | 100 | 100 | 100 | 95 | 80 | 100 | 100 | 100 |

| 62 g ai/ha | Compounds | | | | | | | |
|---|---|---|---|---|---|---|---|---|
| | 1 | 8 | 24 | 27 | 28 | 30 | 31 | 35 |
| Preemergence | | | | | | | | |
| Barley, Spring | 0 | 20 | 30 | 35 | 20 | 35 | 45 | 40 |
| Barley, Winter | 5 | 25 | 25 | 30 | 20 | 30 | 40 | 40 |
| Blackgrass | 35 | 70 | 50 | 45 | 50 | 60 | 60 | 65 |
| Bluegrass | 35 | 70 | 80 | 85 | 45 | 100 | 95 | 95 |
| Bromegrass, Down | 0 | 35 | 35 | 65 | 45 | 55 | 50 | 60 |
| Buckwheat, Wild | 70 | 100 | 60 | 70 | 75 | 85 | 75 | 70 |

TABLE D-continued

| | | | | | | | | |
|---|---|---|---|---|---|---|---|---|
| Canarygrass | 30 | 100 | 60 | 75 | 60 | 100 | 90 | 100 |
| Chamomile | 20 | 30 | 85 | 100 | 75 | 100 | 100 | 100 |
| Chickweed | 100 | 100 | 70 | 100 | 70 | 100 | 100 | 100 |
| Deadnettle | 100 | 100 | 85 | 100 | 95 | 100 | 90 | 100 |
| Field Poppy | 100 | 100 | 100 | 100 | 100 | 100 | 100 | 100 |
| Field Violet | 95 | 100 | 80 | 98 | 95 | 100 | 100 | 100 |
| Foxtail, Green | 100 | 100 | 98 | 100 | 85 | 100 | 100 | 100 |
| *Galium* | — | 35 | 65 | 100 | 75 | 80 | 80 | 80 |
| *Kochia* | 70 | 100 | 90 | 95 | 85 | 90 | 90 | 90 |
| Lambsquarters | 100 | 100 | 80 | 95 | 85 | 95 | 85 | 95 |
| Mustard, Wild | 100 | 100 | 100 | 100 | 100 | 100 | 100 | 100 |
| Oat, Wild | 0 | 40 | 30 | 45 | 30 | 70 | 55 | 75 |
| Oilseed Rape | 100 | 60 | 55 | 60 | 15 | 35 | 35 | 40 |
| Pigweed | 100 | 100 | 100 | 100 | 100 | 100 | 100 | 100 |
| Radish, Wild | 100 | 60 | 75 | 85 | 60 | 95 | 100 | 85 |
| Russian Thistle | — | — | 85 | 85 | 85 | 90 | 85 | 80 |
| Ryegrass, Ital. | 25 | 40 | 40 | 65 | 25 | 55 | 50 | 65 |
| Speedwell | 100 | 100 | 100 | 100 | 100 | 100 | 100 | 100 |
| Wheat, Spring | 0 | 15 | 25 | 20 | 20 | 35 | 40 | 50 |
| Wheat, Winter | 0 | 25 | 20 | 30 | 25 | 25 | 20 | 40 |
| Windgrass | 100 | 90 | 65 | 80 | 50 | 100 | 100 | 85 |

| | Compounds | | | | | | | |
|---|---|---|---|---|---|---|---|---|
| 31 g ai/ha | 1 | 8 | 24 | 27 | 28 | 30 | 31 | 35 |
| | Preemergence | | | | | | | |
| Barley, Spring | 0 | 5 | 25 | 25 | 20 | 40 | 45 | 40 |
| Barley, Winter | 0 | 5 | 15 | 25 | 15 | 25 | 35 | 40 |
| Blackgrass | 15 | 65 | 45 | 30 | 30 | 45 | 40 | 40 |
| Bluegrass | 10 | 70 | 75 | 55 | 35 | 75 | 65 | 80 |
| Bromegrass, Down | 0 | 10 | 40 | 20 | 40 | 40 | 25 | 40 |
| Buckwheat, Wild | 60 | 35 | 55 | 80 | 65 | 70 | 75 | 70 |
| Canarygrass | 5 | 50 | 50 | 55 | 40 | 70 | 85 | 95 |
| Chamomile | 0 | 10 | 35 | 90 | 20 | 40 | 95 | 100 |
| Chickweed | 90 | 100 | 60 | 95 | 70 | 80 | 90 | 85 |
| Deadnettle | 100 | 100 | 80 | 100 | 75 | 95 | 80 | 85 |
| Field Poppy | 100 | 100 | 100 | 98 | 95 | 98 | 100 | 100 |
| Field Violet | 90 | 100 | 15 | 85 | 85 | 100 | 100 | 100 |
| Foxtail, Green | 85 | 100 | 80 | 100 | 85 | 100 | 100 | 100 |
| *Galium* | 65 | — | 70 | 75 | 70 | 75 | 75 | 75 |
| *Kochia* | 60 | 65 | 90 | 95 | 85 | 90 | 85 | 90 |
| Lambsquarters | 60 | 100 | 75 | 95 | 90 | 90 | 95 | 95 |
| Mustard, Wild | 100 | 100 | 70 | 100 | 100 | 100 | 100 | 100 |
| Oat, Wild | 0 | 5 | 25 | 40 | 35 | 55 | 55 | 55 |
| Oilseed Rape | 25 | 20 | 20 | 15 | 15 | 35 | 30 | 30 |
| Pigweed | 100 | 100 | 100 | 100 | 100 | 100 | 100 | 100 |
| Radish, Wild | 50 | 35 | 70 | 85 | 50 | 70 | 80 | 70 |
| Russian Thistle | — | — | 75 | 80 | 75 | 90 | 80 | 75 |
| Ryegrass, Ital. | 10 | 25 | 40 | 35 | 25 | 40 | 45 | 55 |
| Speedwell | 100 | 100 | 85 | 100 | 95 | 100 | 100 | 100 |
| Wheat, Spring | 0 | 10 | 15 | 15 | 15 | 30 | 35 | 40 |
| Wheat, Winter | 0 | 10 | 15 | 25 | 20 | 15 | 20 | 35 |
| Windgrass | 20 | 100 | 25 | 30 | 25 | 75 | 98 | 80 |

| | Compounds | | | | | |
|---|---|---|---|---|---|---|
| 16 g ai/ha | 24 | 27 | 28 | 30 | 31 | 35 |
| | Preemergence | | | | | |
| Barley, Spring | 20 | 25 | 15 | 30 | 35 | 30 |
| Barley, Winter | 15 | 15 | 10 | 20 | 25 | 25 |
| Blackgrass | 20 | 25 | 30 | 30 | 35 | 35 |
| Bluegrass | 20 | 20 | 25 | 75 | 55 | 70 |
| Bromegrass, Down | 25 | 0 | 35 | 35 | 25 | 15 |
| Buckwheat, Wild | 50 | 65 | 60 | 70 | 65 | 65 |
| Canarygrass | 55 | 35 | 10 | 50 | 50 | 45 |
| Chamomile | 0 | 10 | 0 | 30 | 30 | 95 |
| Chickweed | 55 | 85 | 65 | 70 | 80 | 70 |
| Deadnettle | 30 | 80 | 20 | 85 | 80 | 80 |
| Field Poppy | 95 | 95 | 70 | 95 | 95 | 100 |
| Field Violet | 0 | 85 | 65 | 100 | 95 | 95 |
| Foxtail, Green | 75 | 95 | 80 | 85 | 95 | 70 |
| *Galium* | 55 | 70 | 65 | 70 | 70 | 70 |
| *Kochia* | 85 | 85 | 85 | 85 | 80 | 90 |
| Lambsquarters | 65 | 85 | 75 | 85 | 75 | 85 |
| Mustard, Wild | 65 | 80 | 90 | 90 | 100 | 70 |
| Oat, Wild | 30 | 25 | 35 | 45 | 35 | 40 |

TABLE D-continued

| | | | | | | |
|---|---|---|---|---|---|---|
| Oilseed Rape | 15 | 5 | 10 | 10 | 10 | 25 |
| Pigweed | 95 | 100 | 100 | 100 | 100 | 100 |
| Radish, Wild | 45 | 75 | — | 65 | — | 65 |
| Russian Thistle | 65 | 75 | 70 | 80 | 70 | 70 |
| Ryegrass, Ital. | 40 | 25 | 25 | 40 | 40 | 35 |
| Speedwell | 80 | 95 | 75 | 100 | 100 | 100 |
| Wheat, Spring | 15 | 15 | 10 | 25 | 30 | 25 |
| Wheat, Winter | 15 | 25 | 15 | 15 | 20 | 20 |
| Windgrass | 0 | 5 | 25 | 25 | 60 | 70 |

Test E

Seeds of plant species selected from corn (*Zea mays*), soybean (*Glycine max*), lambsquarters (*Chenopodium album*), poinsettia, wild (wild poinsettia, *Euphorbia heterophylla*), pigweed, palmer (palmer pigweed, *Amaranthus palmeri*), waterhemp (common waterhemp, *Amaranthus rudis*), surinam grass (*Brachiaria decumbens*), crabgrass, large (large crabgrass, *Digitaria sanguinalis*), crabgrass, Brazilian (Brazilian crabgrass, *Digitaria horizontalis*), panicum, fall (fall panicum, *Panicum dichotomiflorum*), foxtail, giant (giant foxtail, *Setaria faberii*), foxtail, green (green foxtail, *Setaria viridis*), goosegrass (*Eleusine indica*), johnsongrass (*Sorghum halepense*), ragweed (common ragweed, *Ambrosia elatior*), barnyardgrass (*Echinochloa crus-galli*), sandbur (southern sandbur, *Cenchrus echinatus*), arrowleaf sida (*Sida rhombifolia*), ryegrass, Italian (Italian ryegrass, *Lolium multiflorum*), dayflower, VA (Virginia dayflower, *Commelina virginica*), field bindweed (*Convolvulus arvensis*), cocklebur (common cocklebur, *Xanthium strumarium*), morningglory (*Ipomoea coccinea*), nightshade (eastern black nightshade, *Solanum ptycanthum*), kochia (*Kochia scoparia*), nutsedge, yellow (yellow nutsedge, *Cyperus esculentus*), smartweed (ladysthumb smartweed, *Polygonum persicaria*), velvetleaf (*Abutilon theophrasti*), horseweed (*Conyza canadensis*), and beggarticks (hairy beggarticks, *Bidens pilosa*), were planted into a silt loam soil and treated preemergence with test chemicals formulated in a non-phytotoxic solvent mixture which included a surfactant.

At the same time, plants from these crop and weed species and also waterhemp_RES1, (ALS & Triazine resistant common waterhemp, *Amaranthus rudis*), and waterhemp_RES2, (ALS & HPPD resistant common waterhemp, *Amaranthus rudis*) were planted in pots containing Sunshine Redi-Earth® planting medium comprising spaghnum peat moss, vermiculite, starter nutrients and dolomitic limestone were treated with postemergence applications of test chemicals formulated in the same manner. Plants ranged in height from 2 to 18 cm for postemergence treatments (1- to 4-leaf stage). Treated plants and controls were maintained in a greenhouse for 14 to 21 d, after which time all species were compared to controls and visually evaluated. Plant response ratings, summarized in Table E, are based on a scale of 0 to 100 where 0 is no effect and 100 is complete control. A dash (-) response means no test result.

TABLE E

| | Compounds | | | | Compounds | | | |
|---|---|---|---|---|---|---|---|---|
| 250 g ai/ha | 1 | 28 | 30 | 125 g ai/ha | 1 | 27 | 28 | 30 |
| Postemergence | | | | | | | | |
| Arrowleaf Sida | 85 | 75 | 98 | Arrowleaf Sida | 70 | 100 | 80 | 95 |
| Barnyardgrass | 30 | 40 | 100 | Barnyardgrass | 20 | 50 | 40 | 90 |
| Beggarticks | 60 | 60 | 75 | Beggarticks | 50 | 55 | 50 | 70 |
| Corn | 10 | 30 | 30 | Corn | 10 | 25 | 20 | 20 |
| Crabgrass, Brazil | 40 | 50 | 85 | Crabgrass, Brazil | 30 | 40 | 50 | 70 |
| Dayflower, VA | 50 | 70 | 90 | Dayflower, VA | 50 | 75 | 70 | 80 |
| Field Bindweed | 75 | 80 | 70 | Field Bindweed | 65 | 80 | 80 | 75 |
| Horseweed | — | 40 | — | Horseweed | — | — | 35 | — |
| *Kochia* | — | 95 | 90 | *Kochia* | — | 95 | 95 | 100 |
| *Panicum*, Fall | 30 | 20 | 30 | *Panicum*, Fall | 20 | 30 | 20 | 35 |
| Pigweed, Palmer | 100 | 95 | 100 | Pigweed, Palmer | 100 | 98 | 90 | 100 |
| Poinsettia, Wild | 90 | — | — | Poinsettia, Wild | 80 | — | — | — |
| Ragweed | — | 50 | 80 | Ragweed | — | 60 | 40 | 75 |
| Ryegrass, Italian | 25 | 30 | 50 | Ryegrass, Italian | 15 | 40 | 25 | 40 |
| Sandbur | 20 | 40 | 35 | Sandbur | 20 | 30 | 30 | 30 |
| Smartweed | 80 | — | — | Smartweed | 30 | — | — | — |
| Soybean | 65 | 80 | 95 | Soybean | 50 | 95 | 95 | 85 |
| Waterhemp | 95 | 95 | 95 | Waterhemp | 95 | 95 | 95 | 95 |
| Waterhemp_RES1 | 95 | 95 | 95 | Waterhemp_RES1 | 95 | 98 | 95 | 100 |
| Waterhemp_RES2 | 95 | 95 | 95 | Waterhemp_RES2 | 90 | 90 | 90 | 95 |
| | Compounds | | | | Compounds | | | |
| 62 g ai/ha | 1 | 27 | 28 | 30 | 31 g ai/ha | 1 | 27 | 28 | 30 |
| Postemergence | | | | | | | | |
| Arrowleaf Sida | 50 | 90 | 80 | 95 | Arrowleaf Sida | 40 | 80 | 70 | 100 |
| Barnyardgrass | 15 | 30 | 25 | 50 | Barnyardgrass | 10 | 20 | 20 | 30 |
| Beggarticks | 40 | 50 | 60 | 60 | Beggarticks | 40 | 50 | 50 | 50 |

TABLE E-continued

| | | | | | | | | | |
|---|---|---|---|---|---|---|---|---|---|
| Corn | 5 | 20 | 20 | 20 | Corn | 5 | 15 | 15 | 10 |
| Crabgrass, Brazil | 30 | 30 | 50 | 60 | Crabgrass, Brazil | 20 | 20 | 40 | 35 |
| Dayflower, VA | 40 | 70 | 70 | 70 | Dayflower, VA | 25 | 60 | 60 | 60 |
| Field Bindweed | 65 | 70 | 75 | 70 | Field Bindweed | 55 | 60 | 50 | 70 |
| Horseweed | — | — | 20 | — | Horseweed | — | — | 20 | — |
| *Kochia* | — | 95 | 95 | 90 | *Kochia* | — | 100 | 90 | 90 |
| *Panicum*, Fall | 20 | 15 | 20 | 30 | *Panicum*, Fall | 20 | 10 | 15 | 20 |
| Pigweed, Palmer | 90 | 100 | 90 | 100 | Pigweed, Palmer | 90 | 98 | 100 | 95 |
| Poinsettia, Wild | 75 | — | — | — | Poinsettia, Wild | 70 | — | — | — |
| Ragweed | — | 50 | 40 | 70 | Ragweed | — | 50 | 40 | 65 |
| Ryegrass, Italian | 10 | 30 | 20 | 25 | Ryegrass, Italian | 10 | 30 | 10 | 25 |
| Sandbur | 15 | 30 | 30 | 30 | Sandbur | 15 | 20 | 20 | 20 |
| Soybean | 50 | 80 | 75 | 80 | Soybean | 40 | 80 | 70 | 75 |
| Waterhemp | 90 | 95 | 90 | 95 | Waterhemp | 80 | 98 | 90 | 95 |
| Waterhemp_RES1 | 90 | 95 | 95 | 98 | Waterhemp_RES1 | 90 | 95 | 95 | 95 |
| Waterhemp_RES2 | 85 | 90 | 90 | 95 | Waterhemp_RES2 | 85 | 95 | 95 | 95 |

| | Compounds | |
|---|---|---|
| 16 g ai/ha | 1 | 27 |

Postemergence

| | | |
|---|---|---|
| Arrowleaf Sida | 30 | 70 |
| Barnyardgrass | 10 | 15 |
| Beggarticks | 20 | 40 |
| Corn | 5 | 10 |
| Crabgrass, Brazil | 20 | 20 |
| Dayflower, VA | 20 | 50 |
| Field Bindweed | 40 | 50 |
| *Kochia* | — | 95 |
| *Panicum*, Fall | 10 | 10 |
| Pigweed, Palmer | 80 | 98 |
| Poinsettia, Wild | 60 | — |
| Ragweed | — | 50 |
| Ryegrass, Italian | 0 | 20 |
| Sandbur | 10 | 0 |
| Soybean | 40 | 70 |
| Waterhemp | 65 | 95 |
| Waterhemp_RES1 | 90 | 95 |
| Waterhemp_RES2 | 80 | 90 |

| | Compounds | | | | Compounds | | | | |
|---|---|---|---|---|---|---|---|---|---|
| 250 g ai/ha | 1 | 6 | 30 | 125 g ai/ha | 1 | 6 | 8 | 27 | 30 |

Preemergence

| | | | | | | | | | |
|---|---|---|---|---|---|---|---|---|---|
| Arrowleaf Sida | 50 | 70 | 95 | Arrowleaf Sida | 20 | 30 | 98 | 90 | 85 |
| Barnyardgrass | 50 | 75 | 95 | Barnyardgrass | 30 | 60 | 95 | 95 | 75 |
| Beggarticks | 60 | 70 | 50 | Beggarticks | 20 | 20 | 20 | 0 | 20 |
| Cocklebur | 30 | 10 | — | Cocklebur | 10 | — | — | — | — |
| Corn | 35 | 60 | 50 | Corn | 25 | 50 | 65 | 50 | 0 |
| Crabgrass, Brazil | 100 | 100 | 100 | Crabgrass, Brazil | 98 | 100 | 100 | 100 | 100 |
| Crabgrass, Large | 100 | 100 | 100 | Crabgrass, Large | 95 | 100 | 100 | 100 | 100 |
| Dayflower, VA | 80 | 90 | 65 | Dayflower, VA | 65 | 80 | 95 | 50 | 25 |
| Field Bindweed | 50 | 70 | 75 | Field Bindweed | 40 | 50 | 95 | 90 | 65 |
| Foxtail, Giant | 98 | 100 | 100 | Foxtail, Giant | 80 | 95 | 100 | 100 | 98 |
| Foxtail, Green | 100 | 100 | 100 | Foxtail, Green | 80 | 80 | 100 | 100 | 100 |
| Goosegrass | 100 | 100 | 100 | Goosegrass | 75 | 75 | 100 | 100 | 100 |
| Horseweed | — | — | 100 | Horseweed | — | — | — | — | 100 |
| Johnsongrass | 60 | 100 | 100 | Johnsongrass | 50 | 80 | 100 | 100 | 98 |
| *Kochia* | 95 | 100 | 100 | *Kochia* | 90 | 85 | 100 | 100 | 100 |
| Lambsquarters | 95 | 100 | 100 | Lambsquarters | 95 | 100 | 100 | 100 | 100 |
| Morningglory | 100 | — | 65 | Morningglory | 60 | 30 | 100 | 35 | 15 |
| Nightshade | 95 | 100 | 98 | Nightshade | 90 | 100 | 100 | 100 | 90 |
| Nutsedge, Yellow | 10 | 40 | 0 | Nutsedge, Yellow | 0 | 30 | 35 | 15 | 0 |
| *Panicum*, Fall | 100 | 100 | 100 | *Panicum*, Fall | 100 | 95 | 100 | 100 | 100 |
| Pigweed, Palmer | 100 | 100 | 100 | Pigweed, Palmer | 100 | 100 | 100 | 100 | 100 |
| Poinsettia, Wild | 50 | 95 | — | Poinsettia, Wild | 40 | 50 | 95 | — | — |
| Ragweed | 75 | 90 | 98 | Ragweed | 65 | 50 | 90 | 80 | 70 |
| Ryegrass, Italian | 40 | 80 | 100 | Ryegrass, Italian | 20 | 70 | 100 | 95 | 75 |
| Sandbur | 50 | 80 | 95 | Sandbur | 40 | 70 | 98 | 98 | 90 |
| Smartweed | 80 | 95 | — | Smartweed | 60 | 95 | — | — | — |
| Soybean | 35 | 70 | 30 | Soybean | 10 | 50 | 50 | 15 | 0 |
| Surinam Grass | 20 | 50 | 70 | Surinam Grass | 20 | 50 | 75 | 15 | 50 |
| Velvetleaf | 50 | 70 | 90 | Velvetleaf | 30 | 50 | 98 | 95 | 75 |
| Waterhemp | 100 | 100 | 100 | Waterhemp | 100 | 100 | 100 | 100 | 100 |

TABLE E-continued

| 62 g ai/ha | Compounds | | | | | 31 g ai/ha | Compounds | | | |
| --- | --- | --- | --- | --- | --- | --- | --- | --- | --- | --- |
| | 1 | 6 | 8 | 27 | 30 | | 1 | 6 | 27 | 30 |
| Preemergence | | | | | | | | | | |
| Arrowleaf Sida | 20 | 10 | 65 | 75 | 65 | Arrowleaf Sida | 10 | 0 | 20 | 40 |
| Barnyardgrass | 30 | 50 | 75 | 90 | 70 | Barnyardgrass | 10 | 40 | 25 | 20 |
| Beggarticks | 0 | 0 | 20 | 0 | 10 | Beggarticks | 0 | 0 | 0 | 0 |
| Cocklebur | 0 | 0 | — | — | — | Cocklebur | 0 | 0 | — | — |
| Corn | 10 | 30 | 25 | 25 | 0 | Corn | 0 | 15 | 0 | 0 |
| Crabgrass, Brazil | 98 | 100 | 100 | 100 | 100 | Crabgrass, Brazil | — | 80 | 100 | 90 |
| Crabgrass, Large | 80 | 90 | 100 | 100 | 98 | Crabgrass, Large | 75 | — | 100 | 98 |
| Dayflower, VA | 25 | 70 | 65 | 10 | 10 | Dayflower, VA | 15 | 60 | 10 | 5 |
| Field Bindweed | 30 | 30 | 70 | 60 | 25 | Field Bindweed | 10 | 10 | 0 | 10 |
| Foxtail, Giant | 80 | 60 | 100 | 100 | 98 | Foxtail, Giant | 30 | — | 95 | 95 |
| Foxtail, Green | 50 | 70 | 100 | 100 | 100 | Foxtail, Green | 50 | — | 100 | 95 |
| Goosegrass | 60 | 50 | 100 | 95 | 100 | Goosegrass | 60 | 50 | 98 | 70 |
| Horseweed | — | — | — | — | 100 | Horseweed | — | — | — | 100 |
| Johnsongrass | 40 | 50 | 65 | 100 | 65 | Johnsongrass | 15 | 40 | 95 | 65 |
| *Kochia* | 80 | 80 | 100 | 100 | 100 | *Kochia* | 60 | 80 | 90 | 90 |
| Lambsquarters | 90 | 100 | 100 | 100 | 98 | Lambsquarters | 65 | 70 | 100 | 90 |
| Morningglory | — | 10 | 70 | 35 | 15 | Morningglory | 40 | 10 | 25 | 25 |
| Nightshade | 75 | 90 | 98 | 98 | 80 | Nightshade | — | 70 | 50 | 20 |
| Nutsedge, Yellow | 0 | 15 | 25 | 0 | 0 | Nutsedge, Yellow | 0 | 0 | 0 | 0 |
| *Panicum*, Fall | 80 | 35 | 100 | 100 | 98 | *Panicum*, Fall | 60 | 20 | 100 | 100 |
| Pigweed, Palmer | 98 | 90 | 100 | 100 | 100 | Pigweed, Palmer | — | 75 | 100 | 90 |
| Poinsettia, Wild | 40 | 50 | 70 | — | — | Poinsettia, Wild | 30 | 30 | — | — |
| Ragweed | 35 | 20 | 80 | 90 | 50 | Ragweed | 10 | 20 | 35 | 65 |
| Ryegrass, Italian | 20 | 50 | 65 | 60 | 40 | Ryegrass, Italian | 0 | 40 | 20 | 30 |
| Sandbur | 20 | 50 | 60 | 75 | 65 | Sandbur | 10 | 40 | 35 | 35 |
| Smartweed | 50 | 60 | — | — | — | Smartweed | 40 | 50 | — | — |
| Soybean | 0 | 40 | 50 | 0 | 0 | Soybean | 0 | 10 | 0 | 0 |
| Surinam Grass | 10 | 40 | 50 | 10 | 20 | Surinam Grass | 0 | 40 | 0 | 15 |
| Velvetleaf | 10 | 40 | 50 | 50 | 65 | Velvetleaf | 10 | 30 | 50 | 50 |
| Waterhemp | 95 | 100 | 100 | 100 | 100 | Waterhemp | 95 | 80 | 100 | 100 |

| 16 g ai/ha | Compounds | | |
| --- | --- | --- | --- |
| | 1 | 6 | 27 |
| Preemergence | | | |
| Arrowleaf Sida | 0 | 0 | 20 |
| Barnyardgrass | 0 | 10 | 10 |
| Beggarticks | 0 | 0 | 0 |
| Cocklebur | 0 | 0 | — |
| Corn | 0 | 0 | 0 |
| Crabgrass, Brazil | — | 75 | 90 |
| Crabgrass, Large | 60 | — | 98 |
| Dayflower, VA | 5 | 10 | 10 |
| Field Bindweed | 0 | 10 | 0 |
| Foxtail, Giant | 20 | 50 | 75 |
| Foxtail, Green | 20 | — | 75 |
| Goosegrass | 50 | 15 | 80 |
| Johnsongrass | 10 | — | 100 |
| *Kochia* | 20 | 60 | 65 |
| Lambsquarters | 10 | — | 80 |
| Morningglory | 10 | — | 15 |
| Nightshade | 50 | 15 | 0 |
| Nutsedge, Yellow | 0 | 0 | 0 |
| *Panicum*, Fall | 15 | — | 65 |
| Pigweed, Palmer | 80 | 50 | 85 |
| Poinsettia, Wild | 10 | 15 | — |
| Ragweed | 0 | 10 | 50 |
| Ryegrass, Italian | 0 | 10 | 0 |
| Sandbur | 0 | 10 | 35 |
| Smartweed | 25 | 20 | — |
| Soybean | 0 | 0 | 0 |
| Surinam Grass | 0 | 20 | 0 |
| Velvetleaf | 0 | 0 | 35 |
| Waterhemp | 20 | — | 100 |

What is claimed is:

1. A compound selected from Formula 1, N-oxides and salts thereof,

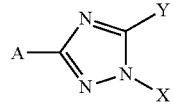

1 wherein

X is $-Q^2-J^2$ and Y is $R^2$;

$R^2$ is $C_1-C_4$ alkoxy, $C_1-C_4$ haloalkoxy, $C_2-C_4$ alkoxyalkyl, $C_1-C_4$ alkyl, $C_1-C_4$ haloalkyl, $C_2-C_4$ alkenyl, $C_2-C_4$ alkynyl, $C_3-C_4$ alkenyloxy, $C_3-C_4$ alkynyloxy, $C_2-C_4$ alkylthioalkyl or $C_3-C_6$ cycloalkyl;

$Q^2$ is $C(R^{4'})(R^{5'})$;

$J^2$ is a 6-membered aromatic heterocyclic ring substituted with 1 $R^7$ and optionally substituted with up to 2 $R^8$ on carbon ring members; or a 5-membered aromatic heterocyclic ring substituted with 1 $R^9$ on a carbon ring member and $R^{11}$ on nitrogen ring members and optionally substituted with 1 $R^{10}$ on a carbon ring member;

A is phenyl substituted with up to 4 $R^{16}$; or a 5- or 6-membered aromatic heterocyclic ring substituted with up to 3 $R^{16}$ on carbon ring members and $R^{17}$ on nitrogen ring members;

$R^{4'}$ is H, F, Cl, Br, cyano, $C_1-C_4$ alkyl, $C_1-C_4$ haloalkyl or $CO_2R^{13}$;

$R^{5'}$ is H, F, $C_1-C_4$ alkyl, OH or $OR^{13}$; or $R^{4'}$ and $R^{5'}$ are taken together with the carbon to which they are attached to form $C(=NOR^{13})$ or $C(=N-N(R^{14})(R^{15}))$;

$R^7$ is $SF_5$, $C_1-C_4$ haloalkyl, $C_1-C_4$ alkoxy, $C_1-C_4$ haloalkoxy or $S(O)_pR^{18}$;

each $R^8$ is independently halogen, cyano, $C_1-C_4$ alkyl, $C_1-C_4$ haloalkyl, $C_1-C_4$ alkoxy, $C_1-C_4$ haloalkoxy or $S(O)_pR^{19}$; or $R^7$ and $R^8$ are taken together to form a 5-membered carbocyclic ring containing ring members selected from up to two O atoms or up to two S atoms, and optionally substituted on carbon atom ring members with up to five halogen atoms;

$R^9$ is $SF_5$, $C_1-C_4$ haloalkyl, $C_1-C_4$ haloalkoxy or $S(O)_pR^{18}$, which is at the position meta to the connection of the ring to the remainder of Formula 1;

$R^{10}$ is halogen, cyano, $C_1-C_4$ alkyl, $C_1-C_4$ haloalkyl, $C_1-C_4$ alkoxy, $C_1-C_4$ haloalkoxy or $S(O)_pR^{19}$;

$R^{11}$ is $C_1-C_4$ alkyl or $C_1-C_4$ haloalkyl;

each $R^{13}$ is independently $C_1-C_4$ alkyl;

$R^{14}$ is $C_1-C_4$ alkyl or $C_1-C_4$ haloalkyl;

$R^{15}$ is $C_1-C_4$ alkyl or $C_1-C_4$ haloalkyl;

each $R^{16}$ is independently halogen, cyano, nitro, $SF_5$, $C_1-C_4$ alkoxy, $C_1-C_4$ haloalkoxy, $C_1-C_4$ alkyl, $C_1-C_4$ haloalkyl, alkenyl, alkynyl, $C_3-C_4$ alkenyloxy, $C_3-C_4$ alkynyloxy or $S(O)_pR^{20}$;

each $R^{17}$ is independently H, $C_1-C_4$ alkyl or $C_1-C_4$ haloalkyl;

each $R^{18}$ is independently $C_1-C_4$ haloalkyl;

each $R^{19}$ is independently $C_1-C_4$ alkyl or $C_1-C_4$ haloalkyl;

$R^{20}$ is $C_1-C_4$ alkyl or $C_1-C_4$ haloalkyl;

n is 0 or 1; and each p is independently 0, 1 or 2.

2. The compound of claim 1 wherein $J^2$ is selected from

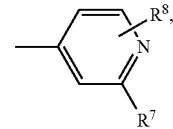 J-2

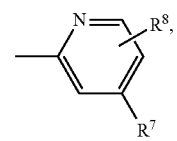 J-3

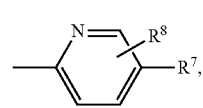 J-4

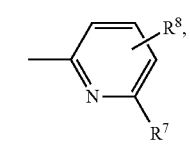 J-5

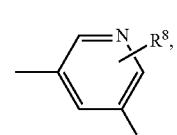 J-6

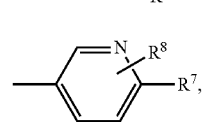 J-7

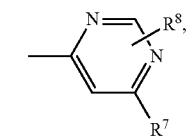 J-8

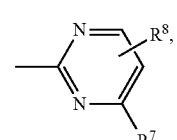 J-9

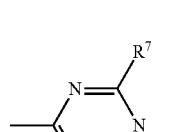 J-12

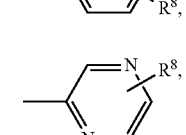 J-13

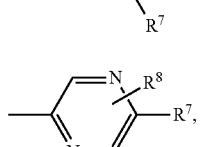 J-14

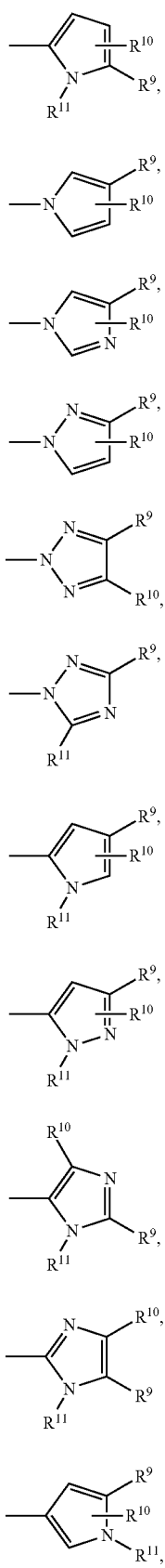

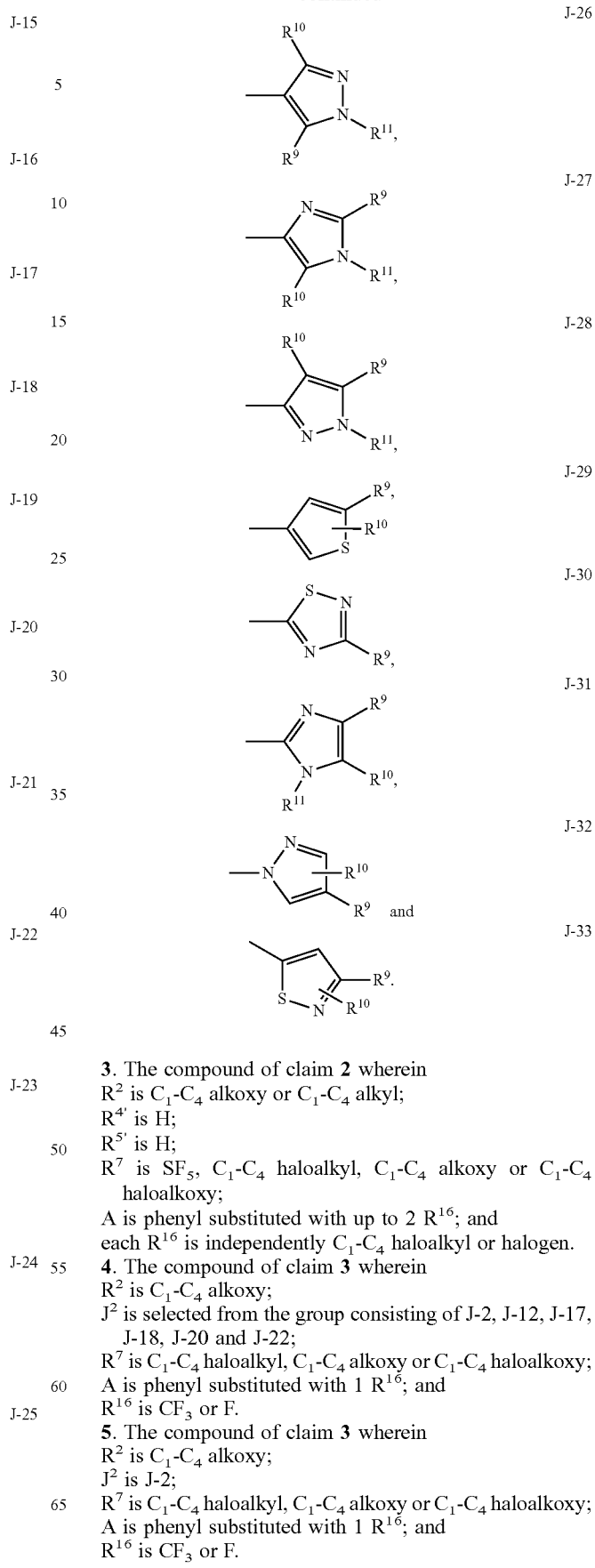

3. The compound of claim 2 wherein
R² is C₁-C₄ alkoxy or C₁-C₄ alkyl;
R⁴' is H;
R⁵' is H;
R⁷ is SF₅, C₁-C₄ haloalkyl, C₁-C₄ alkoxy or C₁-C₄ haloalkoxy;
A is phenyl substituted with up to 2 R¹⁶; and
each R¹⁶ is independently C₁-C₄ haloalkyl or halogen.

4. The compound of claim 3 wherein
R² is C₁-C₄ alkoxy;
J² is selected from the group consisting of J-2, J-12, J-17, J-18, J-20 and J-22;
R⁷ is C₁-C₄ haloalkyl, C₁-C₄ alkoxy or C₁-C₄ haloalkoxy;
A is phenyl substituted with 1 R¹⁶; and
R¹⁶ is CF₃ or F.

5. The compound of claim 3 wherein
R² is C₁-C₄ alkoxy;
J² is J-2;
R⁷ is C₁-C₄ haloalkyl, C₁-C₄ alkoxy or C₁-C₄ haloalkoxy;
A is phenyl substituted with 1 R¹⁶; and
R¹⁶ is CF₃ or F.

6. The compound of claim 3 wherein $R^{16}$ is at the position para to the connection of the phenyl ring to the remainder of Formula 1.

7. The compound of claim 4 wherein $R^{16}$ is at the position para to the connection of the phenyl ring to the remainder of Formula 1.

8. The compound of claim 5 wherein $R^{16}$ is at the position para to the connection of the phenyl ring to the remainder of Formula 1.

9. The compound of claim 2 wherein $R^2$ is $C_1$-$C_4$ alkoxy, $C_1$-$C_4$ haloalkoxy, $C_2$-$C_4$ alkoxyalkyl, $C_1$-$C_4$ alkyl or $C_1$-$C_4$ haloalkyl.

10. A compound of claim 1 selected from the group consisting of:
   4-[[5-ethyl-3-[4-(trifluoromethyl)phenyl]-1H-1,2,4-triazol-1-yl]methyl]-2-(trifluoromethyl)pyridine;
   4-[[3-(4-fluoromethyl)-5-propyl-1H-1,2,4-triazol-1-yl]methyl]-2-(trifluoromethyl)-pyridine;
   4-[[5-ethoxy-3-(4-fluorophenyl)-1H-1,2,4-triazol-1-yl]methyl]-2-(trifluoromethyl)-pyridine
   and
   4-[[3-(4-fluorophenyl)-5-methoxy-1H-1,2,4-triazol-1-yl]methyl]-2-(trifluoromethyl)-pyridine.

11. The compound of claim 1 that is 4-[[5-ethoxy-3-(4-fluorophenyl)-1H-1,2,4-triazol-1-yl]methyl]-2-(trifluoromethyl)pyridine.

12. A herbicidal composition comprising a compound of claim 1 and at least one component selected from the group consisting of surfactants, solid diluents and liquid diluents.

13. A herbicidal composition comprising a compound of claim 1, at least one additional active ingredient selected from the group consisting of other herbicides and herbicide safeners, and at least one component selected from the group consisting of surfactants, solid diluents and liquid diluents.

14. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) herbicides selected from the group consisting of: mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oxaziclomefone, pelargonic acid, and pyributicarb, (b16) herbicide safeners, and salts of compounds of (b1) through (b16).

15. A method for controlling the growth of undesired vegetation comprising contacting the vegetation or its environment with a herbicidally effective amount of a compound of claim 1.

* * * * *